US012180285B2

United States Patent
Spriggs et al.

(10) Patent No.: US 12,180,285 B2
(45) Date of Patent: Dec. 31, 2024

(54) ANTIBODIES TO GALECTIN-3 AND METHODS OF USE THEREOF

(71) Applicant: MEMORIAL SLOAN KETTERING CANCER CENTER, New York, NY (US)

(72) Inventors: David Spriggs, New York, NY (US); Dharmarao Thapi, New York, NY (US); Marina Stasenko, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 1012 days.

(21) Appl. No.: 16/966,438

(22) PCT Filed: Feb. 1, 2019

(86) PCT No.: PCT/US2019/016430
§ 371 (c)(1),
(2) Date: Jul. 30, 2020

(87) PCT Pub. No.: WO2019/152895
PCT Pub. Date: Aug. 8, 2019

(65) Prior Publication Data
US 2021/0032350 A1 Feb. 4, 2021

Related U.S. Application Data

(60) Provisional application No. 62/625,166, filed on Feb. 1, 2018.

(51) Int. Cl.
*C07K 16/28* (2006.01)
*A61K 35/17* (2015.01)
(Continued)

(52) U.S. Cl.
CPC .......... *C07K 16/2851* (2013.01); *A61K 35/17* (2013.01); *A61K 47/6849* (2017.08);
(Continued)

(58) Field of Classification Search
CPC ............ C07K 16/2851; C07K 14/7056; C07K 16/2809; C07K 2317/24; C07K 2317/31;
(Continued)

(56) References Cited

U.S. PATENT DOCUMENTS

| 8,765,797 B2 | 7/2014 | Mehta et al. | |
| 2005/0032673 A1* | 2/2005 | John | C07K 14/4726 424/130.1 |
| 2017/0355756 A1* | 12/2017 | Julien | C07K 16/18 |

FOREIGN PATENT DOCUMENTS

| CN | 107383192 B | 11/2017 |
| WO | WO-2004/091634 A1 | 10/2004 |

(Continued)

OTHER PUBLICATIONS

Strome et al., "A mechanistic perspective of monoclonal antibodies in cancer therapy beyong target-related effects", 2007, The Oncologist; 12:1084-95. (Year: 2007).*

(Continued)

*Primary Examiner* — Aurora M Fontainhas
*Assistant Examiner* — Selam Berhane
(74) *Attorney, Agent, or Firm* — Foley & Lardner LLP

(57) ABSTRACT

Provided herein are compositions, methods, and uses involving antibodies that immunospecifically bind the Galactin-3 (LGALS3) carbohydrate binding domain (CBD). Also provided herein are uses and methods for managing, treating, or preventing disorders, such as cancer.

20 Claims, 35 Drawing Sheets

Specification includes a Sequence Listing.

Role of LGALS3 linking cancer mucin to signaling molecules (EGFR and IntegrinB)

Inhibition of LGALS3 by antibodies (in red) with loss of TKI and Integrin Signals

(51) Int. Cl.
  A61K 39/00    (2006.01)
  A61K 47/68    (2017.01)
  A61P 35/04    (2006.01)
  C07K 14/705   (2006.01)

(52) U.S. Cl.
  CPC .......... *A61K 47/6851* (2017.08); *A61P 35/04* (2018.01); *C07K 14/7056* (2013.01); *C07K 16/2809* (2013.01); *A61K 2039/505* (2013.01); *C07K 2317/24* (2013.01); *C07K 2317/31* (2013.01); *C07K 2317/52* (2013.01); *C07K 2317/565* (2013.01); *C07K 2317/622* (2013.01); *C07K 2317/73* (2013.01); *C07K 2317/76* (2013.01); *C07K 2319/30* (2013.01); *C07K 2319/33* (2013.01)

(58) Field of Classification Search
  CPC .......... C07K 2317/52; C07K 2317/565; C07K 2317/622; C07K 2317/73; C07K 2317/76; C07K 2319/30; C07K 2319/33; A61K 47/6851; A61K 47/6849; A61K 35/17; A61K 2039/505; A61P 35/04
  See application file for complete search history.

(56) References Cited

FOREIGN PATENT DOCUMENTS

| WO | WO-2008068048 A2 * | 6/2008 | .............. A61P 31/10 |
| WO | WO-2014/089267 A1 | 6/2014 | |
| WO | WO-2016/149368 A1 | 9/2016 | |
| WO | WO-2019/068863 A1 | 4/2019 | |

OTHER PUBLICATIONS

Brand et al., "Prospect for Anti-HER2 Receptor Therapy in Breast Cancer", 2006, Anticancer Res.; 26(1B):463-70. (Year: 2006).*

Chen et al., Enhancement and destruction of antibody function by somatic mutation: unequal occurrence is controlled by V gene combinatorial associations. EMBO J. Jun. 15, 1995;14(12):2784-94. (Year: 1995).*

Edwards et al., The remarkable flexibility of the human antibody repertoire; isolation of over one thousand different antibodies to a single protein, BLyS. J Mol Biol. Nov. 14, 2003;334(1): 103-18. (Year: 2003).*

Kussie, Paul H., "A Single Engineered Amino Acid Substitution Changes Antibody Fine Specificity", 1994, Journal of Immunology 152(1): pp. 146-152. (Year: 1994).*

Fukaya et al: "Identification of galectin-3-binding protein as a factor secreted by tumor cells that stimulates interleukin-6 expression in the bone marrow stroma", Journal of Biological Chemistry, American Society for Biochemistry and Molecular Biology, US, vol. 283, No. 27, Jul. 4, 2008 (Jul. 4, 2008), pp. 18573-18581.

International Search Report and Written Opinion, PCT/US2019/016430, Memorial Sloan Kettering Cancer Center (Jul. 3, 2019).

* cited by examiner

Fig. 1A
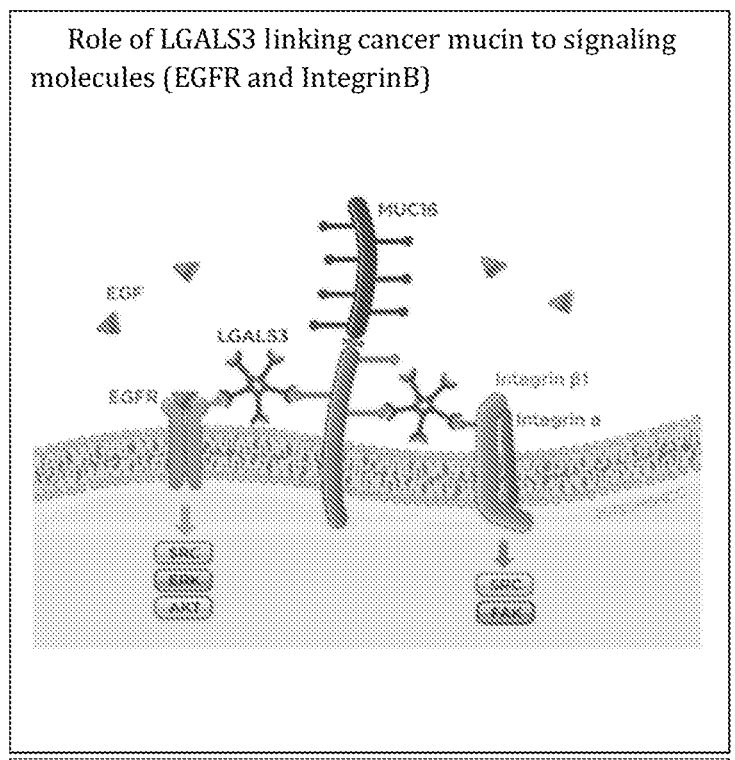
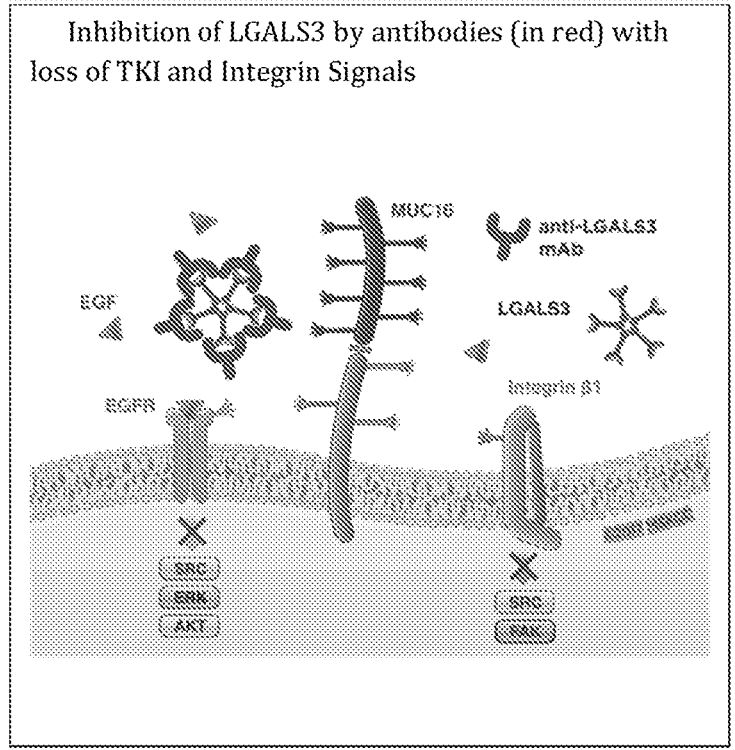
Fig. 1B

FIG. 3

Known *In Vitro* / *In Vivo* Experimental Functions of Galectin 3

| GAL3 Function | Description of GAL3 effect | Potential Blocking Ab effect | References |
|---|---|---|---|
| Immune function | -CD8 T-cell Suppression via LAG3<br>-Decrease monocyte migration and enhance apoptosis<br>-Promotes T-cell Apoptosis<br>-Suppressed TCR activation infiltrating tumor | T cell activation<br>Monocyte activation<br>Decreased T cell apoptosis<br>Rescues T cell suppression | Kouo, T., *et al.*, Cancer Immunol Res, 2015. 3(4): 412-23<br>Paclik, D., *et al.*, Cell Immunol, 2011. 271(1): 97-103<br>Guha, P., *et al.*, *Proc Natl Acad Sci U S A*, 2013. 110(13): 5052-7<br>Chen, H.Y., *et al.*, *Proc Natl Acad Sci U S A*, 2009. 106(34): 14496-501 |
| Thrombosis | GAL3 promotes venous thrombosis | Decreased thrombosis | DeRoo, E.P., *et al.*, Blood, 2015. 125(11): 1813-21 |
| Metastasis promotion | GAL3 promotes bone metastasis<br><br>GAL3 promotes metastasis by microenvironment changes | Decrease metastasis<br><br>Decrease metastasis | Nakajima, K., *et al.*, *Cancer Metastasis Rev*, 2016. 35(2): 333-46<br>Ruvolo, P.P., *Biochim Biophys Acta*, 2016. 1863(3): p. 427-37 |
| Cardiac | Elevated in heart failure / fibrosis | Less CHF /fibrosis | Lala, R.I., *et al.*, *Acta Cardiol*, 2015. 70(3): 323-31 |
| Renal | GAL3 Increased in lupus GN, fibrosis and loss of GFR | Decreased inflammation in renal disease | Chen, S.C. and P.L. Kuo, *Int J Mol Sci*, 2016. 17(4): 565 |
| Pulmonary | GAL3 increased in pulmonary fibrosis syndromes | Decreased fibrosis | Nishi, Y., *et al.*, *Allergol Int*, 2007. 56(1): 57-65 |
| Infection control | Promotion of neutrophil activation | Decrease local neutrophil recruitment | Wright, R.D., *et al.*, *J Leukoc Biol*, 2017. 101(3): 717-726 |
| Endocrine | GAL3 loss exacerbates hyperglycemia in K/O mice on high fat diet | Hyperglycemia | Darrow, A.L. and R.V. Shohet, *Cardiovasc Diabetol*, 2015. 14: 73 |
| Angiogenesis | GAL3 promotes angiogenesis via stabilized VEGFR2<br>GAL3 promotes drug resistance and angiogenesis in ovarian ca | Decreased angiogenesis<br>Decreased drug resistance | Jia, W., *et al.*, *Am J Pathol*, 2013. 182(5): 1821-31<br>Mirandola, L., *et al.*, *Gynecol Oncol*, 2014. 135(3): 573-9;<br>Ebrahim, A.H., *et al.*, *Ann Transl Med*, 2014. 2(9): 88;<br>Mirandola, L., *et al.*, *Int Rev Immunol*, 2014. 33(5): p. 417-27; Pena, C., *et al.*, *Ann Transl Med*, 2014. 2(9): 87 |

Galectin-3 Carbohydrate Binding Domain

GNDVAFHF NPRFNENNRR VIVCNTKLDN NWGREERQSV FPFESG
                    160        170        180        190

| Totals | N | Total | CBD-3 | LGALS3 | GAL1 CBD | GAL1 | GAL7 | GAL9 | GAL3-N |
|---|---|---|---|---|---|---|---|---|---|
| Group A | | | | | | | | | |
| IgG1 | 7 | | + | + | - | - | - | - | - |
| IgG2a | 1 | | + | + | - | - | - | - | - |
| IgG2b | 3 | | + | + | - | - | - | - | - |
| | | 11 | | | | | | | |
| Group B | | | | | | | | | |
| IgG1 | 5 | | + | - | - | - | - | - | - |
| IgG2a | 4 | | + | - | - | - | - | - | - |
| IgG2b | 2 | | + | - | - | - | - | - | - |
| | | 11 | | | | | | | |
| Group C | | | | | | | | | |
| IgG1 | 3 | | | | | | | | |
| | | 3 | - | + | - | - | - | - | - |
| Group D | | | | | | | | | |
| IgG1 | 0 | | | | | | | | |
| IgG2a | 2 | | + | + | + | + | - | - | - |
| IgG2b | 1 | | + | + | + | + | - | - | - |
| | | 3 | | | | | | | |
| Group E | | | | | | | | | |
| IgG1 | 0 | | | | | | | | |
| IgG2a | 1 | 1 | + | - | + | + | - | - | - |
| IgG2b | 0 | | | | | | | | |
| | | 1 | | | | | | | |
| Group F | | | | | | | | | |
| IgG1 | 0 | | | | | | | | |
| IgG2a | 0 | | | | | | | | |
| IgG2b | 1 | | + | + | + | - | - | - | - |
| | | 1 | | | | | | | |
| Group G | 0 | 0 | | | | | | | |

FIG. 12A

14D11.2D2 ("14D11") Heavy Chain:

Nucleic Acid

CAGGTGCAGCTGAAGGAGTCAGGACCTGGCCTGGTGGCGCCCTCACAGAGCC
TGTCCATCACATGCACCATCTCAGGGTTCTCATTAAGTAGTTATGGTGTACATTG
GGTTCGCCAGCCTCCAGGAAAGGGTCTGGAGTGGCTGGTAGTGATATGGAGT
GATGGAAGCACAACCTATAATTCAACTCTCAAATCCAGACTGAGCATCAGCAAG
GACAACTCCAAGAGCCAAGTTTTCTTAAAAATGAACAGTCTCCAAACTGATGAC
ACAGCCATGTACTACTGTGCCAGACATATTAGTAACTACGGAACTATGGACTAC
TGGGGTCAAGGAACCTCAGTCACCGTCTCC (SEQ ID NO: 23)

Amino Acid

QVQLKESGPGLVAPSQSLSITCTISGFSLSSYGVHWVRQPPGKGLEWLVVIWSDG
STTYNSTLKSRLSISKDNSKSQVFLKMNSLQTDDTAMYYCARHISNYGTMDYWGQ
GTSVTVS(SEQ ID NO: 24)

| | CDR-1 | CDR-2 | CDR-3 |
|---|---|---|---|
| Kabat | SYGVH (SEQ ID NO: 5) | VIWSDGSTTYNSTLKS (SEQ ID NO: 6) | HISNYGTMDY (SEQ ID NO: 7) |
| Chothia | GFSLSSY (SEQ ID NO: 11) | WSDGS (SEQ ID NO: 12) | HISNYGTMDY (SEQ ID NO: 13) |
| IMGT | GFSLSSYG (SEQ ID NO: 17) | IWSDGST (SEQ ID NO: 18) | ARHISNYGTMDY (SEQ ID NO: 19) |

FIG. 12B

14D11.2D2 ("14D11") Light Chain:

Nucleic Acid:

GATATCCAGATGACACAGACTACATCCTCCCTGTCTGCCTCTCTGGGAGACAGA
GTCACCATCAGTTGCAGGGCAAGTCAGGACATTAGGAATTATTTAAACTGGTAT
CAGCAGAAACCAGATGGATCTATTAAACTCCTGATCTACTACACATCAAGATTAC
ACTCAGGAGTCCCATCAAGGTTCAGTGGCAGTGGGTCTGGAACAGATTATTCTC
TCACCATTAGGAACCTGGAGCAAGAAGATATTGCCACTTACTTTTGCCAACACT
TTAATACGCTTCCTCCGACGTTCGGTGGAGGCACCAAGCTGGAAATCAAA (SEQ
ID NO: 25)

Amino Acid

DIQMTQTTSSLSASLGDRVTISCRASQDIRNYLNWYQQKPDGSIKLLIYYTSRLHSG
VPSRFSGSGSGTDYSLTIRNLEQEDIATYFCQHFNTLPPTFGGGTKLEIK(SEQ ID
NO: 26)

|  | CDR-1 | CDR-2 | CDR-3 |
|---|---|---|---|
| Kabat | RASQDIRNYLN (SEQ ID NO: 8) | YTSRLHS (SEQ ID NO: 9) | QHFNTLPPT (SEQ ID NO: 10) |
| Chothia | RASQDIRNYLN (SEQ ID NO: 14) | YTSRLHS (SEQ ID NO: 15) | QHFNTLPPT (SEQ ID NO: 16) |
| IMGT | QDIRNY (SEQ ID NO: 20) | YTS (SEQ ID NO: 21) | QHFNTLPPT (SEQ ID NO: 22) |

| S.No | Isotype | mAb | HEAVY CHAIN - Kabat | | | LIGHT CHAIN - Kabat | | |
|---|---|---|---|---|---|---|---|---|
| | | | CDR1 | CDR2 | CDR3 | CDR1 | CDR2 | CDR3 |
| 1 | IgG1 lambda | 3G10.D11 | SYGMS (SEQ ID NO: 33) | TISSGGSYTYYPDSVKG (SEQ ID NO: 34) | YDGYFVGFTY (SEQ ID NO: 35) | n.d. | n.d. | n.d. |
| 2 | IgG1 lambda | 11D1.A12 | SYGMS (SEQ ID NO: 36) | TISSGGSYTYYPDSVKG (SEQ ID NO: 37) | LGSRYDYYGMDY (SEQ ID NO: 38) | n.d. | n.d. | n.d. |
| 3 | IgG1 lambda | 11E12.EE4 | TYAMH (SEQ ID NO: 299) | YINPSSGYIEYNQKFKD (SEQ ID NO: 300) | HWGAY (SEQ ID NO: 301) | KASENVGTYLS (SEQ ID NO: 72) | GTSNRFT (SEQ ID NO: 73) | GQTLKYPHT (SEQ ID NO: 74) |
| 4 | IgG2b kappa | 5G2.A6 | SHVMY (SEQ ID NO: 39) | AIYPGNSDTTYNQKFKG (SEQ ID NO: 40) | NYVWYFDV (SEQ ID NO: 41) | KSSQSLLDSDGKTYLN (SEQ ID NO: 75) | LVSKVDS (SEQ ID NO: 76) | WQGTHFPFT (SEQ ID NO: 77) |
| 5 | IgG2b kappa | 4B10.B12 | SHVMY (SEQ ID NO: 42) | AIYPGNSDTTYNQKFKG (SEQ ID NO: 43) | NYVWYFDV (SEQ ID NO: 44) | KSSQSLLDSDGKTYLN (SEQ ID NO: 78) | LVSKVDS (SEQ ID NO: 79) | WQGTHFPFT (SEQ ID NO: 80) |
| 6 | IgG2a lambda | 21A12.A6 | SFAMS (SEQ ID NO: 45) | TISTGGSYTYYLDSGKG (SEQ ID NO: 46) | RAGTGRLPAMFAY (SEQ ID NO: 47) | n.d. | n.d. | n.d. |
| 7 | IgG1 lambda | 1D1.A12 | SYGMS (SEQ ID NO: 48) | TISSGGNYIYYPDSVKG (SEQ ID NO: 49) | YDGYFVGFTY (SEQ ID NO: 50) | RASENIYSYLA (SEQ ID NO: 81) | NAKTLAE (SEQ ID NO: 82) | QHHYGTPWT (SEQ ID NO: 83) |
| 8a | IgG1 lambda | 7A2.A7a | SYGMS (SEQ ID NO: 51) | TISSGGSYTYYPDSVKG (SEQ ID NO: 52) | YDGYFVGFTY (SEQ ID NO: 53) | RASQSIGNNLH (SEQ ID NO: 84) | YASQSIS (SEQ ID NO: 85) | QQTNIWPYT (SEQ ID NO: 86) |
| 8b | IgG1 lambda | 7A2.A7b | SYGMS (SEQ ID NO: 51) | TISSGGSYTYYPDSVKG (SEQ ID NO: 52) | YDGYFVGFTY (SEQ ID NO: 53) | RSSTGAVITSNYAN (SEQ ID NO: 87) | GTNNRAP (SEQ ID NO: 88) | ALRYSNHW (SEQ ID NO: 89) |
| 9 | IgG2a kappa | 5G4.A3 | SYGMS (SEQ ID NO: 54) | TISSGGSYTYYPDSVKG (SEQ ID NO: 55) | QTVGYFDY (SEQ ID NO: 56) | TASSSVSSSYLH (SEQ ID NO: 90) | STSNLAS (SEQ ID NO: 91) | HQYHRSPPIT (SEQ ID NO: 92) |
| 10 | IgG2b kappa | 1E4.E11 | RSWMY (SEQ ID NO: 57) | AIYPGNSDTTYNQKFKG (SEQ ID NO: 58) | NSGAMDS (SEQ ID NO: 59) | KSRQSLLDSDGKTYLN (SEQ ID NO: 93) | LVSKLDS (SEQ ID NO: 94) | WQGTHFPWT (SEQ ID NO: 95) |
| 11a | IgG2a lambda | 12A11.A7 | SYGMS (SEQ ID NO: 60) | TISSGGSYIFYPDSVKG (SEQ ID NO: 61) | YDGYFVGFTY (SEQ ID NO: 62) | RASENIYSY1A (SEQ ID NO: 96) | NAKTLAE (SEQ ID NO: 97) | QHHYGTPWT (SEQ ID NO: 98) |
| 11b | IgG2a lambda | 12A11.A7 | SYGMS (SEQ ID NO: 60) | TISSGGSYIFYPDSVKG (SEQ ID NO: 61) | YDGYFVGFTY (SEQ ID NO: 62) | RSSTGAVTTSNYAN (SEQ ID NO: 99) | GTNNRAP (SEQ ID NO: 100) | VLRYSNHW (SEQ ID NO: 101) |
| 12a | IgG2b lambda | 15D12.A7a | DYVIH (SEQ ID NO: 63) | TIDTSDSYTTYNQKFKD (SEQ ID NO: 64) | LLRLRYFEY (SEQ ID NO: 65) | RSSTGAVTTSNYAN (SEQ ID NO: 102) | DTNNRAP (SEQ ID NO: 103) | ALWYNNHSWV (SEQ ID NO: 104) |
| 12b | IgG2b lambda | 15D12.A7b | DYYIH (SEQ ID NO: 66) | RINPNNGDSAYNQNFKD (SEQ ID NO: 67) | RQIHYYGMDF (SEQ ID NO: 68) | RSSTGAVTTSNYAN (SEQ ID NO: 102) | DTNNRAP (SEQ ID NO: 103) | ALWYNNHSWV (SEQ ID NO: 104) |
| 12c | IgG2b lambda | 15D12.A7c | SDYTWN (SEQ ID NO: 69) | YISYSGSTSYNPSLKS (SEQ ID NO: 70) | GSGYSLYTMDY (SEQ ID NO: 71) | RSSTGAVTTSNYAN (SEQ ID NO: 102) | DTNNRAP (SEQ ID NO: 103) | ALWYNNHSWV (SEQ ID NO: 104) | n.d. = not determined

FIG. 13A

| S.No | Isotype | mAb | HEAVY CHAIN - Chothia | | | LIGHT CHAIN - Chothia | | |
|---|---|---|---|---|---|---|---|---|
| | | | CDR1 | CDR2 | CDR3 | CDR1 | CDR2 | CDR3 |
| 1 | IgG1 lambda | 3G10.D11 | GFTFSSY (SEQ ID NO: 105) | SSGGSY (SEQ ID NO: 106) | YDGYFVGFTY (SEQ ID NO: 107) | n.d. | n.d. | n.d. |
| 2 | IgG1 lambda | 11D1.A12 | GFTFSSY (SEQ ID NO: 108) | SSGGSY (SEQ ID NO: 109) | LGSRYDYYGMDY (SEQ ID NO: 110) | n.d. | n.d. | n.d. |
| 3 | IgG1 lambda | 11E12.E4 | GYTFTTY (SEQ ID NO: 302) | NPSSGY (SEQ ID NO: 303) | HWGAY (SEQ ID NO: 304) | KASENVGTYLS (SEQ ID NO: 111) | GTSNRFT (SEQ ID NO: 112) | GQTLKYPHT (SEQ ID NO: 113) |
| 4 | IgG2b kappa | 5G2.A6 | GYTFTSH (SEQ ID NO: 114) | YPGNSD (SEQ ID NO: 115) | NYVWYFDV (SEQ ID NO: 116) | KSSQSLLDSDGKTYLN (SEQ ID NO: 117) | LVSKVDS (SEQ ID NO: 118) | WQGTHFPFT (SEQ ID NO: 119) |
| 5 | IgG2b kappa | 4B10.B12 | GYTFTSH (SEQ ID NO: 120) | YPGNSD (SEQ ID NO: 121) | NYVWYFDV (SEQ ID NO: 122) | KSSQSLLDSDGKTYLN (SEQ ID NO: 123) | LVSKVDS (SEQ ID NO: 124) | WQGTHFPFT (SEQ ID NO: 125) |
| 6 | IgG2a lambda | 21A12.A6 | GFTFSSP (SEQ ID NO: 126) | STGGSY (SEQ ID NO: 127) | RAGTGRLPAWFAY (SEQ ID NO: 128) | n.d. | n.d. | n.d. |
| 7 | IgG1 lambda | 1D1.A12 | GFTFSSY (SEQ ID NO: 129) | SSGGNY (SEQ ID NO: 130) | YDGYFVGFTY (SEQ ID NO: 131) | RASENIYSYLA (SEQ ID NO: 132) | NAKTLAE (SEQ ID NO: 133) | QHHYGTPWT (SEQ ID NO: 134) |
| 8a | IgG1 lambda | 7A2.A7 | GFTFSSY (SEQ ID NO: 135) | SSGGSY (SEQ ID NO: 136) | YDGYFVGFTY (SEQ ID NO: 137) | GFTFSSY (SEQ ID NO: 138) | SSGGSY (SEQ ID NO: 139) | YDGYFVGFTY (SEQ ID NO: 140) |
| 8b | IgG1 lambda | 7A2.A7 | GFTFSSY (SEQ ID NO: 135) | SSGGSY (SEQ ID NO: 136) | YDGYFVGFTY (SEQ ID NO: 137) | RSSTGAVTTSNYAN (SEQ ID NO: 141) | GTNNRAP (SEQ ID NO: 142) | ALRYSNHW (SEQ ID NO: 143) |
| 9 | IgG2a kappa | 5G4.A3 | GFTFSSY (SEQ ID NO: 144) | SSGGSY (SEQ ID NO: 145) | QTVGYFDY (SEQ ID NO: 146) | TASSSVSSSYLH (SEQ ID NO: 147) | STSNLAS (SEQ ID NO: 148) | HQYHRSPPIT (SEQ ID NO: 149) |
| 10 | IgG2b kappa | 1E4.E11 | GYTFTRS (SEQ ID NO: 150) | YPGNSD (SEQ ID NO: 151) | NSGAMDS (SEQ ID NO: 152) | KSRQSLLDSDGKTYLN (SEQ ID NO: 153) | LVSKLDS (SEQ ID NO: 154) | WQGTHFPWT (SEQ ID NO: 155) |
| 11a | IgG2a lambda | 12A11.A7a | GFTFSSY (SEQ ID NO: 156) | SSGGSY (SEQ ID NO: 157) | YDGYFVGFTY (SEQ ID NO: 158) | RASENIYSYLA (SEQ ID NO: 159) | NAKTLAE (SEQ ID NO: 160) | QHHYGTPWT (SEQ ID NO: 161) |
| 11b | IgG2a lambda | 12A11.A7b | GFTFSSY (SEQ ID NO: 156) | SSGGSY (SEQ ID NO: 157) | YDGYFVGFTY (SEQ ID NO: 158) | RSSTGAVTTSNYAN (SEQ ID NO: 162) | GTNNRAP (SEQ ID NO: 163) | VLRYSNHW (SEQ ID NO: 164) |
| 12a | IgG2b lambda | 15D12.A7a | GYTFSDY (SEQ ID NO: 165) | DTSDSY (SEQ ID NO: 166) | LLRLRYFEY (SEQ ID NO: 167) | RSSTGAVTTSNYAN (SEQ ID NO: 168) | DTNNRAP (SEQ ID NO: 169) | ALWYNNHSWV (SEQ ID NO: 170) |
| 12b | IgG2b lambda | 15D12.A7b | GYSFTDYY (SEQ ID NO: 171) | NPNNGD (SEQ ID NO: 172) | RQIHYYGMDF (SEQ ID NO: 173) | RSSTGAVTTSNYAN (SEQ ID NO: 168) | DTNNRAP (SEQ ID NO: 169) | ALWYNNHSWV (SEQ ID NO: 170) |
| 12c | IgG2b lambda | 15D12.A7c | GYSITSDY (SEQ ID NO: 174) | SYSGS (SEQ ID NO: 175) | GSGYSLYTMDY (SEQ ID NO: 176) | RSSTGAVTTSNYAN (SEQ ID NO: 168) | DTNNRAP (SEQ ID NO: 169) | ALWYNNHSWV (SEQ ID NO: 170) | n.d. = not determined

| | | | HEAVY CHAIN - IMGT | | | LIGHT CHAIN - IMGT | | |
|---|---|---|---|---|---|---|---|---|
| S.No | isotype | mAb | CDR1 | CDR2 | CDR3 | CDR1 | CDR2 | CDR3 |
| 1 | IgG1 lambda | 3G10.D11 | GFTFSSYG (SEQ ID NO: 177) | ISSGGSYT (SEQ ID NO: 178) | ANYDGYFVGFTY (SEQ ID NO: 179) | n.d. | | |
| 2 | IgG1 lambda | 11D1.A12 | GFTFSSYG (SEQ ID NO: 180) | ISSGGSYT (SEQ ID NO: 181) | ARLGSRYDYYGMDY (SEQ ID NO: 182) | n.d. | n.d. | n.d. |
| 3 | IgG1 lambda | 11E12.E1/E4 | GYTFTTYA (SEQ ID NO: 305) | INPSSGYI (SEQ ID NO: 306) | ARHWGAY (SEQ ID NO: 307) | ENVGTY (SEQ ID NO: 183) | GTS (SEQ ID NO:184) | GQTLKYPHT (SEQ ID NO: 185) |
| 4 | IgG2b kappa | 5G2.A6 | GYTFTSHW (SEQ ID NO: 186) | YPGNSDT (SEQ ID NO: 187) | NSNYVWYFDV (SEQ ID NO: 188) | QSLLDSDGKTY (SEQ ID NO: 189) | LVS (SEQ ID NO: 190) | WQGTHFPFT (SEQ ID NO: 191) |
| 5 | IgG2b kappa | 4810.B12 | GYTFTSHW (SEQ ID NO: 192) | YPGNSDT (SEQ ID NO: 193) | NSNYVWYFDV (SEQ ID NO: 194) | QSLLDSDGKTY (SEQ ID NO: 195) | LVS (SEQ ID NO: 196) | WQGTHFPFT (SEQ ID NO: 197) |
| 6 | IgG2a lambda | 21A12.A6 | GFTFSSPA (SEQ ID NO: 198) | ISTGGSYT (SEQ ID NO: 199) | VSRAGTGRLPAWFAY (SEQ ID NO: 200) | n.d. | | |
| 7 | IgG1 lambda | 1D1.A12 | GFTFSSYG (SEQ ID NO: 201) | ISSGGNYI (SEQ ID NO: 202) | ANYDGYFVGFTY (SEQ ID NO: 203) | ENIYSY (SEQ ID NO: 204) | NAK (SEQ ID NO: 205) | QHHYGTPWT (SEQ ID NO: 206) |
| 8a | IgG1 lambda | 7A2.A7a | GFTFSSYG (SEQ ID NO: 207) | ISSGGSYT (SEQ ID NO: 208) | ANYDGYFVGFTY (SEQ ID NO: 209) | QSIGNN (SEQ ID NO: 210) | YAS (SEQ ID NO: 211) | QQTNIWPYT (SEQ ID NO: 212) |
| 8b | IgG1 lambda | 7A2.A7b | GFTFSSYG (SEQ ID NO: 207) | ISSGGSYT (SEQ ID NO: 208) | ANYDGYFVGFTY (SEQ ID NO: 209) | TGAVTTSNY (SEQ ID NO: 213) | GTN (SEQ ID NO: 214) | ALRYSNHW (SEQ ID NO: 215) |
| 9 | IgG2a kappa | 5G4.A3 | GFTFSSYG (SEQ ID NO: 216) | ISSGGSYT (SEQ ID NO: 217) | ARQTVGYFDY (SEQ ID NO: 218) | SSVSSSY (SEQ ID NO: 219) | STS (SEQ ID NO: 220) | HQYHRSPPIT (SEQ ID NO: 221) |
| 10 | IgG2b kappa | 1E4.E11 | GYTFTRSW (SEQ ID NO:222) | YPGNSDT (SEQ ID NO: 223) | NTNSGAMDS (SEQ ID NO: 224) | QSLLDSDGKTY (SEQ ID NO: 225) | LVS (SEQ ID NO: 226) | WQGTHFPWT (SEQ ID NO: 227) |
| 11a | IgG2a lambda | 12A11.A7a | GFTFSSYG (SEQ ID NO: 228) | ISSGGSYI (SEQ ID NO: 229) | ANYDGYFVGFTY (SEQ ID NO: 230) | ENIYSY (SEQ ID NO: 231) | NAK (SEQ ID NO: 232) | QHHYGTPWT (SEQ ID NO: 233) |
| 11b | IgG2a lambda | 12A11.A7b | GFTFSSYG (SEQ ID NO: 228) | ISSGGSYI (SEQ ID NO: 229) | ANYDGYFVGFTY (SEQ ID NO: 230) | TGAVTTSNY (SEQ ID NO: 234) | GTN (SEQ ID NO: 235) | VLRYSNHW (SEQ ID NO: 236) |
| 12a | IgG2b lambda | 15D12.A7a | GYTFSDYW (SEQ ID NO: 237) | IDTSDSYT (SEQ ID NO: 238) | ATLLRLRYYFEY (SEQ ID NO: 239) | TGAVTTSNY (SEQ ID NO: 240) | DTN (SEQ ID NO: 241) | ALWYNNHSWV (SEQ ID NO: 242) |
| 12b | IgG2b lambda | 15D12.A7b | GYSFTDYY (SEQ ID NO: 243) | INPNNGDS (SEQ ID NO: 244) | ARRQIHYYGMDF (SEQ ID NO: 245) | TGAVTTSNY (SEQ ID NO: 240) | DTN (SEQ ID NO: 241) | ALWYNNHSWV (SEQ ID NO: 242) |
| 12c | IgG2b lambda | 15D12.A7c | GYSITSDYT (SEQ ID NO: 246) | ISYSGST (SEQ ID NO: 247) | ARGSGYSLYTMDY (SEQ ID NO: 248) | TGAVTTSNY (SEQ ID NO: 240) | DTN (SEQ ID NO: 241) | ALWYNNHSWV (SEQ ID NO: 242) | n.d. = not determined

FIG. 13D

3G10.D11 Heavy Chain (DNA)

GAGGTGCAGCTGGTGGAGTCTGGGGGAGACTTAGTGAAGCCTGGAGGGTCCCTGAAACTCTCC
TGTGCAGCCTCTGGATTCACTTTCAGTAGCTATGGCATGTCTTGGGTTCGCCAGACTCCAGACAA
GAGGCTGGAGTGGGTCGCAACCATTAGTAGTGGTGGTAGTTACACCTACTATCCAGACAGTGTG
AAGGGGCGATTCACCATCTCCAGAGACAATGCCAAGAACACCCTGTACCTGCAAATGAGTAGTCT
GAAGTCTGAGGACACAGCCATGTATTCCTGTGCAAACTATGATGGTTACTTCGTCGGGTTTACTT
ACTGGGGCCAAGGGACTCTGGTCACTGTCTCTGCA (SEQ ID NO: 249)

3G10.D11 Heavy Chain (AA)

EVQLVESGGDLVKPGGSLKLSCAASGFTFSSYGMSWVRQTPDKRLEWVATISSGGSYTYYPDSVKGR
FTISRDNAKNTLYLQMSSLKSEDTAMYSCANYDGYFVGFTYWGQGTLVTVSA (SEQ ID NO: 250)

FIG. 13E

11D1.A12 Heavy Chain (DNA)

GAGGTGCAGCTGGTGGAGTCTGGGGGAGACTTAGTGAAGCCTGGAGGGTCCCTGAAACTCTCC
TGTGCAGCCTCTGGATTCACTTTCAGTAGCTATGGCATGTCTTGGGTTCGCCAGACTCCAGACAA
GAGGCTGGAGTGGGTCGCAACCATTAGTAGTGGTGGTAGTTACACCTACTATCCAGACAGTGTG
AAGGGGCGATTCACCATCTCCAGAGACAATGCCAAGAACACCCTGTACCTGCAAATGAGCAGTC
TGAAGTCTGAGGACACAGCCATGTATTACTGTGCAAGACTCGGTAGTAGGTACGATTACTATGGT
ATGGACTACTGGGGTCAAGGAACCTCAGTCACCGTCTCCTCA (SEQ ID NO: 251)

11D1.A12 Heavy Chain (AA)

EVQLVESGGDLVKPGGSLKLSCAASGFTFSSYGMSWVRQTPDKRLEWVATISSGGSYTYYPDSVKGR
FTISRDNAKNTLYLQMSSLKSEDTAMYYCARLGSRYDYYGMDYWGQGTSVTVSS (SEQ ID NO: 252)

FIG. 13F

11E12.E4 Heavy Chain (DNA)
CAGGTCCAGCTGCAGCAGTCTGCAGCTGAACTGGCAAGACCTGGGGCCTCAGTGAAGATGTCCT
GCAAGGCTTCTGGCTACACCTTTACTACCTACGCGATGCACTGGTTAAAACAGAGGCCTGGACAG
GGTCTGGAATGGCTTGGATACATTAATCCTAGCAGTGGATACATTGAATATAATCAGAAGTTCAAG
GACAAGACCACATTGACTGCAGACAAATCTTCCAGCACAGCCTACATGCAACTGAGCAGCCTGAC
ATCTGAGGACTCTGCGGTCTATTACTGTGCAAGACACTGGGGTGCTTACTGGGGCCAAGGGACT
CTGGTCACTGTTTCTGCA (SEQ ID NO: 253)

11E12.E4 Heavy Chain (AA)
QVQLQQSAAELARPGASVKMSCKASGYTFTTYAMHWLKQRPGQGLEWLGYINPSSGYIEYNQKFKD
KTTLTADKSSSTAYMQLSSLTSEDSAVYYCARHWGAYWGQGTLVTVSA (SEQ ID NO: 254)

11E12.E4 Light Chain (DNA)
GACATTGTGATGACCCAGTCTCAAAAATTCATGTCCACATCAGTAGGAGACAGGGTCAGCGTCAC
CTGCAAGGCCAGTCAGAGTGTGGGTACTAATGTAGCCTGGTATCAACAGAAACCAGGACAATCTC
CTAAAGCACTGATTTACTCGGCATCTTATCGATACAGTGGAGTCCCTGATCGCTTCACAGGCCGT
GGATCTGGGACAGATTTCACTCTCACCATCACCAGTGTGCAGTCTGAAGACTTGGCAAAGTATGT
CTGTCAGCAATATTTCAACTATCCGCTCACGTTCGGTGCTGGGACCAAGCTGGAGCTGAAAC
(SEQ ID NO: 255)

11E12.E4 Light Chain (AA)
DIVMTQSQKFMSTSVGDRVSVTCKASQSVGTNVAWYQQKPGQSPKALIYSASYRYSGVPDRFTGRG
SGTDFTLTITSVQSEDLAKYVCQQYFNYPLTFGAGTKLELK (SEQ ID NO: 256)

FIG. 13G

5G2.A6 Heavy Chain (DNA)
GAGGTTCAGCTCCAGCAGTCTGGGACTGTAGTGGCAAGGCCTGGGGCTTCAGTGAAGATGTCCT
GCAAGGCTTCTGGCTACACCTTTACCAGCCACTGGATGTACTGGGTAAAACAGAGGCCTGGACAG
GGTCTGGAATGGATTGGCGCTATTTATCCTGGAAATAGTGATACTACCTACAACCAGAAGTTCAAG
GGCAAGGCCAAACTGACTGCAGTCACATCCACCAGCACTGCCTACATGGAGCTCAGCAGCCTGA
CAAATGAGGACTCTGCGGTCTATTACTGTAACAGTAACTACGTCTGGTACTTCGATGTCTGGGGC
GCAGGGACCACGGTCGCCGTCTCCTCA (SEQ ID NO: 257)

5G2.A6HeavyChain(AA)
EVQLQQSGTVVARPGASVKMSCKASGYTFTSHWMYWVKQRPGQGLEWIGAIYPGNSDTTYNQKFK
GKAKLTAVTSTSTAYMELSSLTNEDSAVYYCNSNYVWYFDVWGAGTTVAVSS (SEQ ID NO:258)

5G2.A6LightChain(DNA)
GATGTTGTGATGACCCAGACTCCACTCACTTTGTCGGTTACCTTTGGACAACCAGCCGCCATCTCT
TGCAAGTCAAGTCAGAGCCTCTTAGATAGTGATGGAAAGACATATTTGAATTGGTTGTCACAGAGG
CCAGGCCAGTCTCCAAAGCGCCTCATCTATCTGGTGTCTAAAGTGGACTCTGGAGTCCCTGACAG
GTTCACTGGCAGTGGATCAGGGACAGATTTCACACTGAAAATCAGCAGAGTGGAGGCTGAGGATT
TGGGAGTTTATTATTGCTGGCAAGGTACGCATTTTCCATTCACATTCGGCTCGGGGACAAAGTTG
GAAATAAAAC (SEQ ID NO:259)

5G2.A6LightChain(AA)
DVVMTQTPLTLSVTFGQPAAISCKSSQSLLDSDGKTYLNWLSQRPGQSPKRLIYLVSKVDSGVPDRFT
GSGSGTDFTLKISRVEAEDLGVYYCWQGTHFPFTFGSGTKLEIK (SEQ ID NO:260)

FIG.13H

4B10.B12HeavyChain(DNA)
GAGGTTCAGCTCCAGCAGTCTGGGACTGTAGTGGCAAGGCCTGGGGCTTCAGTGAAGATGTCCT
GCAAGGCTTCTGGCTACACCTTTACCAGCCACTGGATGTACTGGGTAAAACAGAGGCCTGGACAG
GGTCTGGAATGGATTGGCGCTATTTATCCTGGAAATAGTGATACTACCTACAACCAGAAGTTCAAG
GGCAAGGCCAAACTGACTGCAGTCACATCCACCAGCACTGCCTACATGGAGCTCAGCAGCCTGA
CAAATGAGGACTCTGCGGTCTATTACTGTAACAGTAACTACGTCTGGTACTTCGATGTCTGGGGC
GCAGGGACCACGGTCGCCGTCTCCTCA (SEQ ID NO:261)

4B10.B12HeavyChain(AA)
EVQLQQSGTVVARPGASVKMSCKASGYTFTSHWMYWVKQRPGQGLEWIGAIYPGNSDTTYNQKFK
GKAKLTAVTSTSTAYMELSSLTNEDSAVYYCNSNYVWYFDVWGAGTTVAVSS (SEQ ID NO:262)

4B10.B12LightChain(DNA)
GATGTTGTGATGACCCAGACTCCACTCACTTTGTCGGTTACCTTTGGACAACCAGCCGCCATCTCT
TGCAAGTCAAGTCAGAGCCTCTTAGATAGTGATGGAAAGACATATTTGAATTGGTTGTCACAGAGG
CCAGGCCAGTCTCCAAAGCGCCTCATCTATCTGGTGTCTAAAGTGGACTCTGGAGTCCCTGACAG
GTTCACTGGCAGTGGATCAGGGACAGATTTCACACTGAAAATCAGCAGAGTGGAGGCTGAGGATT
TGGGAGTTTATTATTGCTGGCAAGGTACGCATTTTCCATTCACATTCGGCTCGGGGACAAAGTTG
GAAATAAAAC (SEQ ID NO:263)

4B10.B12LightChain(AA)
DVVMTQTPLTLSVTFGQPAAISCKSSQSLLDSDGKTYLNWLSQRPGQSPKRLIYLVSKVDSGVPDRFT
GSGSGTDFTLKISRVEAEDLGVYYCWQGTHFPFTFGSGTKLEIK (SEQ ID NO:264)

FIG.13I

21A12.A6HeavyChain(DNA)
GAAGTGCTGTTGGTGGAGTCTGGGGGAGGCTTTGTGAGGCCTGGAGGGTCCCTAAAACTCTCCT
GTATAGCCTCTGGATTCACTTTCAGTAGTTTTGCCATGTCTTGGGTTCGCCAGACTCCGGAGAAGA
GGCTGGAGTGGGTCGCAACCATTAGTACCGGTGGTTCTTACACCTACTATTTAGACAGTGGGAAG
GGGCGATTCACCATCTCCAGAGACAATGCCAAGAACACCCTGTACCTGCAAATGACCAGTCTGAG
GTCTGAGGACACGGCCATGTATTACTGTGTAAGTCGAGCTGGGACGGGACGCCTCCCGGCCTGG
TTTGCTTACTGGGGCCAAGGGACTCTGGTCACTGTCTCTGCA (SEQ ID NO:265)

21A12.A6HeavyChain(AA)
EVLLVESGGGFVRPGGSLKLSCIASGFTFSSFAMSWVRQTPEKRLEWVATISTGGSYTYYLDSGKGR
FTISRDNAKNTLYLQMTSLRSEDTAMYYCVSRAGTGRLPAWFAYWGQGTLVTVSA (SEQ ID NO:266)

FIG.13J

1D1.A12HeavyChain(DNA)
GAGGTGCAGCTGGTGGAGTCTGGGGGAGACTTAGTGAAGCCTGGAGGGTCCCTGAAACTCTCCT
GTGCAGCCTCTGGATTCACTTTCAGTAGCTATGGCATGTCTTGGGTTCGCCAGACTCCAGACAAG
AGGCTGGAGTGGGTCGCAACCATTAGCAGTGGTGGTAATTATATCTATTATCCAGACAGTGTGAA
GGGGCGATTCACCATCTCCAGAGACAATGCCAAGAACACCCTGTACCTGCAAATGAGCAGTCTGA
GGTCTGAGGACACAGCCATGTATTACTGTGCAAACTATGATGGTTACTTCGTCGGCTTTACTTACT
GGGGCCAAGGGACTCTGGTCACTGTCTCTGCA (SEQ ID NO:267)

1D1.A12HeavyChain(AA)
EVQLVESGGDLVKPGGSLKLSCAASGFTFSSYGMSWVRQTPDKRLEWVATISSGGNYIYYPDSVKGR
FTISRDNAKNTLYLQMSSLRSEDTAMYYCANYDGYFVGFTYWGQGTLVTVSA (SEQ ID NO:268)

1D1.A12LightChain(DNA)
GACATCCAGATGACTCAGTCTCCAGCCTCCCTATCTGCATCTGTGGGAGAAACTGTCACCATCAC
ATGTCGAGCAAGTGAGAATATTTACAGTTATTTAGCATGGTATCAGCAGAAACAGGGAAAATCTCC
TCAGCTCCTGGTCAGAAATGCAAAAACCTTAGCAGAAGGTGTGTCATCAAGATTCAGTGGCAGTG
GATCAGGCACACAGTTTTCTCTGAAGATCAACAGCCTGCAGCCTGAAGATTTTGGGAGTTATTACT
GTCAACATCATTATGGTACTCCGTGGACGTTCGGTGGAGGCACCAAGCTGGAAATCAAAC (SEQ
ID NO:269)

1D1.A12LightChain(AA)
DIQMTQSPASLSASVGETVTITCRASENIYSYLAWYQQKQGKSPQLLVRNAKTLAEGVSSRFSGSGSG
TQFSLKINSLQPEDFGSYYCQHHYGTPWTFGGGTKLEIK (SEQ ID NO:270)

FIG.13K

7A2.A7HeavyChain(DNA)
GAGGTGCAGCTGGTGGAGTCTGGGGGAGACTTAGTGAAGCCTGGAGGGTCCCTGAAACTCTCCT
GTGCAGCCTCTGGATTCACTTTCAGTAGCTATGGCATGTCTTGGGTTCGCCAGACTCCAGACAAG
AGGCTGGAGTGGGTCGCAACCATTAGTAGTGGTGGTAGTTACACCTACTATCCAGACAGTGTGAA
GGGGCGATTCACCATCTCCAGAGACAATGCCAAGAACACCCTGTACCTGCAAATGAGTAGTCTGA
AGTCTGAGGACACAGCCATGTATTCCTGTGCAAACTATGATGGTTACTTCGTCGGGTTTACTTACT
GGGGCCAAGGGACTCTGGTCACTGTCTCTGCA (SEQ ID NO:271)

7A2.A7HeavyChain(AA)
EVQLVESGGDLVKPGGSLKLSCAASGFTFSSYGMSWVRQTPDKRLEWVATISSGGSYTYYPDSVKG
RFTISRDNAKNTLYLQMSSLKSEDTAMYSCANYDGYFVGFTYWGQGTLVTVSA (SEQ ID NO:272)

7A2.A7aLightChain1(DNA)
GATATTGTGCTAACTCAGTCTCCAGCCACCCTGTCTGTGACTCCAGGAGATAGCGTCAGTCTTTC
CTGCAGGGCCAGCCAAAGTATTGGCAACAACCTACACTGGTATCAACAGAAATCACATGAGTCTC
CAAGGCTTCTCATCAAGTATGCTTCCCAGTCCATCTCTGGGATCCCCTCCAGGTTCAGTGGCAGT
GGATCAGGGACAGATTTCACTCTCATTATCAATAGTGTGGAGACTGAAGATTTTGGAATGTATTTC
TGTCAACAGACTAACATCTGGCCGTACACGTTCGGAGGGGGGACCAAGCTGGAGCTGAAAC
(SEQ ID NO:273)

7A2.A7aLightChain1(AA)
DIVLTQSPATLSVTPGDSVSLSCRASQSIGNNLHWYQQKSHESPRLLIKYASQSISGIPSRFSGSGSGT
DFTLIINSVETEDFGMYFCQQTNIWPYTFGGGTKLELK (SEQ ID NO:274)

7A2.A7bLightChain2(DNA)
CAGGCTGTTGTGACTCAGGAATCTGCACTCACCACATCACCTGGTGAAACAGTCACACTCACTTG
TCGCTCAAGTACTGGGGCTGTTACAACTAGTAACTATGCCAACTGGGTCCAAGAAAAACCAGCAT
TTATTCACTGGTCTAATAGGTGGTACCAACAACCGAGCTCCAGGTGTTCCTGCCAGATTCTCAGG
CTCCCTGATTGGAGACAAGGCTGCCCTCACCATCACAGGGGCACAGACTGAGGATGAGCATATAT
TTCTGTGCTCTACGGTACAGCAACCATTGGGTGTTCGGTGGAGGAACCAAACTGACTGTCCTAG
(SEQ ID NO:275)

7A2.A7bLightChain2(AA)
QAVVTQESALTTSPGETVTLTCRSSTGAVTTSNYANWVQEKPDHLFTGLIGGTNNRAPGVPARFSGS
LIGDKAALTITGAQTEDEAIYFCALRYSNHWVFGGGTKLTVL (SEQ ID NO:276)

FIG.13L

5G4.A3HeavyChain(DNA)
GAGGTGCAGCTGGTGGAGTCTGGGGGAGACTTAGTGAAGCCTGGAGGGTCCCTGAAACTCTCCT
GTGCAGCCTCTGGATTCACTTTCAGTAGCTATGGCATGTCTTGGATTCGCCAGACTCCAGACAAG
AGGCTGGAGTGGGTCGCAACCATTAGTAGTGGTGGTAGTTACACCTACTATCCAGACAGTGTGAA
GGGGCGATTCACCATCTCCAGAGACAATGCCAAGAACACCCTGTACCTGCAAATGAGCAGTCTGA
AGTCTGAAGACACAGCCATGTATTACTGTGCAAGACAAACGGTAGGATACTTTGACTACTGGGGC
CAAGGCACCACTCTCACAGTCTCCTCA (SEQ ID NO:277)

5G4.A3HeavyChain(AA)
EVQLVESGGDLVKPGGSLKLSCAASGFTFSSYGMSWIRQTPDKRLEWVATISSGGSYTYYPDSVKGR
FTISRDNAKNTLYLQMSSLKSEDTAMYYCARQTVGYFDYWGQGTTLTVSS (SEQ ID NO:278)

5G4.A3LightChain(DNA)
CAAATTGTTCTCACCCAGTCTCCAGCAATCATGTCTCCATCTCTAGGGGAACGGGTCACCATGAC
CTGCACTGCCAGCTCAAGTGTAAGTTCCAGTTACTTGCACTGGTACCAGCAGAAGTCAGGATCCT
CCCCCAAACTCTGGATTTATAGCACATCCAACCTGGCTTCTGGAGTCCCAGCTCGCTTCAGTGGC
AGGGGGTCTGGGACCTCTTACTCTCTCACAATCAGCAGCATGGAGGCTGAAGATGCTGCCACTTA
TTACTGCCACCAGTATCATCGTTCCCCACCCATCACGTTCGGTGCTGGGACCAAGCTGGAGCTGA
AAC (SEQ ID NO:279)

5G4.A3LightChain(AA)
QIVLTQSPAIMSPSLGERVTMTCTASSSVSSSYLHWYQQKSGSSPKLWIYSTSNLASGVPARFSGRGS
GTSYSLTISSMEAEDAATYYCHQYHRSPPITFGAGTKLELK (SEQ ID NO:280)

FIG.13M

1E4.E11HeavyChain(DNA)
GAGATTCGGCTCCAACAGTCTGGAAGTATGCTGGCAAGGCCTGGGGCTTCAGTGAAGATGTCCT
GCAAGGCTTCTGGCTACACCTTTACCAGGTCCTGGATGTACTGGATGAAACAGAGGCCTGGACAG
GGTCTGGAATGGATTGGCGCTATTTATCCTGGAAACAGTGATACAACCTACAACCAGAAGTTCAA
GGGCAAGGCCAAACTGACTGCAGTCACTTCCACCAACACTGCCTACATGGAGCTCAACAGCCTGA
CAAATGAGGACTCTGCGGTCTATTATTGTAATACTAACTCGGGGGCTATGGACTCCTGGGGTCAA
GGAGCCTCACTCACCGTCTCCTCA (SEQ ID NO:281)

1E4.E11HeavyChain(AA)
EIRLQQSGSMLARPGASVKMSCKASGYTFTRSWMYWMKQRPGQGLEWIGAIYPGNSDTTYNQKFKG
KAKLTAVTSTNTAYMELNSLTNEDSAVYYCNTNSGAMDSWGQGASLTVSS (SEQ ID NO:282)

1E4.E11LightChain(DNA)
GATGTTGTGATGACCCAGAGTCCACTCACTTTGTCGGTTACCATTGGACAGCCAGCCTCCTTCTCT
TGCAAGTCAAGGCAGAGCCTCTTAGATAGTGATGGAAAGACATATTTGAATTGGTTGTTGCAGAG
GCCAGGCCAGTCTCCAAAGCGCCTAATCTATCTGGTGTCTAAACTGGACTCTGGAGTCCCTGACA
GGTTCACTGGCAGTGGATCAGGGACAGATTTCACACTGACAATCAGCAGAGTGGAGGCTGAGGA
TTTGGGAGTTTATTATTGCTGGCAAGGTACACATTTTCCGTGGACGTTCGGTGGAGGCACCAAGC
TGGAAATCAAAC (SEQ ID NO:283)

1E4.E11LightChain(AA)
DVVMTQSPLTLSVTIGQPASFSCKSRQSLLDSDGKTYLNWLLQRPGQSPKRLIYLVSKLDSGVPDRFT
GSGSGTDFTLTISRVEAEDLGVYYCWQGTHFPWTFGGGTKLEIK (SEQ ID NO:284)

FIG.13N

12A11.A7HeavyChain(DNA)
GAGGTGCAGCTGGTGGAGTCTGGGGGAGACTTAGTGAAGCCTGGAGGGTCCCTGAAACTCTCCT
GTGCAGCCTCTGGATTCACTTTCAGTAGCTATGGCATGTCTTGGGTTCGCCAGACTCCAGACAAG
AGGCTGGAGTGGGTCGCAACCATTAGCAGTGGTGGTAGTTATATCTTTTATCCAGACAGTGTGAA
GGGGCGATTCACCATCTCCAGAGACAATGCCAAGAACACCCTGTACCTGCAAATGAGCAGTCTGA
GGTCTGAGGACACAGCCATGTATTACTGTGCAAACTATGATGGTTACTTCGTCGGATTTACTTACT
GGGGCCAAGGGACTCTGGTCACTGTCTCTGCA (SEQ ID NO:285)

12A11.A7HeavyChain(AA)
EVQLVESGGDLVKPGGSLKLSCAASGFTFSSYGMSWVRQTPDKRLEWVATISSGGSYIFYPDSVKGR
FTISRDNAKNTLYLQMSSLRSEDTAMYYCANYDGYFVGFTYWGQGTLVTVSA (SEQ ID NO:286)

12A11.A7aLightChain1(DNA)
GACATCCAGATGACTCAGTCTCCAGCCTCCCTATCTGCATCTGTGGGAGAAACTGTCACCATCAC
ATGTCGAGCAAGTGAGAATATTTACAGTTATTTAGCATGGTATCAGCAGAAACAGGGAAAATCTCC
TCAGCTCCTGGTCAGAAATGCAAAAACCTTAGCAGAAGGTGTGTCATCAAGATTCAGTGGCAGTG
GATCAGGCACACAGTTTTCTCTGAAGATCAACAGCCTGCAGCCTGAAGATTTGGGAGTTATTACT
GTCAACATCATTATGGTACTCCGTGGACGTTCGGTGGAGGCACCAAGCTGGAAATCAAAC (SEQ
ID NO:287)

12A11.A7aLightChain1(AA)
DIQMTQSPASLSASVGETVTITCRASENIYSYLAWYQQKQGKSPQLLVRNAKTLAEGVSSRFSGSGSG
TQFSLKINSLQPEDFGSYYCQHHYGTPWTFGGGTKLEIK (SEQ ID NO:288)

12A11.A7bLightChain2(DNA)
CAGGCTGTTGTGACTCAGGAATCTGCACTCACCACATCACCTGGTGAAACAGTCACACTCACTTG
TCGCTCAAGTACTGGGGCTGTTACAACTAGTAACTATGCCAACTGGGTCCAAGAAAAACCAGCAT
TTATTCACTGGTCTAATAGGTGGTACCAACAACCGAGCTCCAGGTGTTCCTGCCAGATTCTCAGG
CTCCCTGATTGGAGACAAGGCTGCCCTCACCATCACAGGGGCACAGACTGAGGATGAGCATATAT
TTCTGTGTTCTACGGTACAGCAACCATTGGGTGTTCGGTGGAGGAACCAAACTGACTGTCCTAG
(SEQ ID NO:289)

12A11.A7bLightChain2(AA)
QAVVTQESALTTSPGETVTLTCRSSTGAVTTSNYANWVQEKPDHLFTGLIGGTNNRAPGVPARFSGS
LIGDKAALTITGAQTEDEAIYFCVLRYSNHWVFGGGTKLTVL (SEQ ID NO:290)

FIG.13O

15D12.A7aHeavyChain1(DNA)
CAGGTCCAACTGCGACAACCTGGGGCTGAGCTTGTGATGCCTGGGGCTTCAGTGAAGATGTCGT
GCAAGACTTCTGGCTACACATTCAGTGACTACTGGATACATTGGGTGAAACAGAGGCCTGGACAA
GGCCTTGAATGGATCGGAACAATTGATACTTCTGATAGTTATACTACCTACAATCAAAAGTTCAAG
GACAAGGCCACGTTGACTGTCGACGAATCTTCCAATACAGCCTTCATGCATCTCAGCAGCCTGAC
ATCTGAGGACTCTGCGGTCTATTATTGTGCAACATTACTTCGGCTACGTTACTACTTTGAATATTGG
GGCCAGGGCACCACTCTCACAGTCTCCTCA (SEQ ID NO:291)

15D12.A7aHeavyChain1(AA)
QVQLRQPGAELVMPGASVKMSCKTSGYTFSDYWIHWVKQRPGQGLEWIGTIDTSDSYTTYNQKFKD
KATLTVDESSNTAFMHLSSLTSEDSAVYYCATLLRLRYYFEYWGQGTTLTVSS (SEQ ID NO:292)

15D12.A7bHeavyChain2(DNA)
GAGGTCCAACTGCAACAGTCTGGACCTGAGTTGGTGAAGCCTGGGGCTTCAGTGAAGATATCCT
GCAAGGCTTCTGGTTACTCATTCACTGACTACTACATACACTGGGTGAAACAAAGCCATGTAAAGA
GCCTTGAATGGATTGGACGTATTAATCCTAACAATGGTGATTCTGCCTACAACCAGAATTTCAAGG
ACAAGGCCAGTTTGACTGTAAATGAGTCCTCCACCACAGCCTATATGGAACTCCACAGCCTGACA
TCTGAGGACTCTGCAGTCTATTACTGTGCAAGACGCCAAATTCACTACTATGGTATGGACTTCTGG
GGTCAAGGAACCTCAGTCACCGTCTCCTCA (SEQ ID NO:293)

15D12.A7bHeavyChain2(AA)
EVQLQQSGPELVKPGASVKISCKASGYSFTDYYIHWVKQSHVKSLEWIGRINPNNGDSAYNQNFKDK
ASLTVNESSTTAYMELHSLTSEDSAVYYCARRQIHYYGMDFWGQGTSVTVSS (SEQ ID NO:294)

15D12.A7cHeavyChain3(DNA)
TCTGATGTGCAGCTTCAGGAGTCGGGACCTGGCCTGGTGAAACCTTCTCAGTCTCTGTCCCTCAC
CTGCACTGTCACTGGCTACTCAATCACCAGTGATTATACCTGGAACTGGATCCGGCAGTTTCCAG
GAAACAAACTGGAGTGGATGGGCTACATAAGCTACAGTGGCAGCACCAGCTACAACCCATCTCTC
AAAAGTCGAATCTCTATCACTCGAGACACATCCAAGAACCAGTTCTTCGTGCAGTTGAATTCTGTG
ACTACTGAGGACACAGCCACATATTACTGTCAAGGGGGAGTGGTTATAGTCTCTATACTATGGA
CTACTGGGGTCAAGGAACCTCAGTCACCGTCTCCTCA (SEQ ID NO:295)

15D12.A7cHeavyChain3(AA)
SDVQLQESGPGLVKPSQSLSLTCTVTGYSITSDYTWNWIRQFPGNKLEWMGYISYSGSTSYNPSLKS
RISITRDTSKNQFFVQLNSVTTEDTATYYCARGSGYSLYTMDYWGQGTSVTVSS (SEQ ID NO:296)

15D12.A7LightChain(DNA)
CAGGCTGTTGTGACTCAGGAATCTGCACTCACCACATCACCTGGTGAAACAGTCACACTCACTTG
TCGCTCAAGTACTGGGGCTGTTACAACTAGTAACTATGCCAACTGGGTCCAAGAAAAACCAGCAT
TTATTCACTGGTCTAGTGGGTGATACCAACAACCGAGCTCCAGGTGTTCCTGCCAGATTCTCAGG
CTCCCTGATTGGAGACAAGGCTGCCCTCACCATCACAGGGGCACAGACTGAGGACGAGCATATA
TTTCTGTGCTCTATGGTACAACAACCATAGCTGGGTGTTCGGTGGAGGAACCAAGCTGGAAATCA
ATC (SEQ ID NO:297)

15D12.A7LightChain(AA)
QAVVTQESALTTSPGETVTLTCRSSTGAVTTSNYANWVQEKPDHLFTGLVGDTNNRAPGVPARFSGS
LIGDKAALTITGAQTEDEAIYFCALWYNNHSWVFGGGTKLEIN (SEQ ID NO:298)

FIG.15

GenBank™ accession number NM_002306.3 Homo sapiens galectin 3 (LG ALS3)
GAGTATTTGAGGCTCGGAGCCACCGCCCCGCCGGCGCCCGCAGCACCTCCTC
GCCAGCAGCCGTCCGGAGCCAGCCAACGAGCGGAAAATGGCAGACAATTTTTC
GCTCCATGATGCGTTATCTGGGTCTGGAAACCCAAACCCTCAAGGATGGCCTGG
CGCATGGGGGAACCAGCCTGCTGGGCAGGGGGCTACCCAGGGGCTTCCTAT
CCTGGGGCCTACCCCGGGCAGGCACCCCAGGGGCTTATCCTGGACAGGCAC
CTCCAGGCGCCTACCTGGAGCACCTGGAGCTTATCCCGGAGCACCTGCACCT
GGAGTCTACCCAGGGCCACCCAGCGGCCCTGGGGCCTACCCATCTTCTGGACA
GCCAAGTGCCACCGGAGCCTACCCTGCCACTGGCCCCTATGGCGCCCCTGCTG
GGCCACTGATTGTGCCTTATAACCTGCCTTTGCCTGGGGGAGTGGTGCCTCGC
ATGCTGATAACAATTCTGGGCACGGTGAAGCCCAATGCAAACAGAATTGCTTTA
GATTTCCAAAGAGGGAATGATGTTGCCTTCCACTTTAACCCACGCTTCAATGAGA
ACAACAGGAGAGTCATTGTTTGCAATACAAAGCTGGATAATAACTGGGGAAGGG
AAGAAAGACAGTCGGTTTTCCCATTTGAAAGTGGGAAACCATTCAAAATACAAGT
ACTGGTTGAACCTGACCACTTCAAGGTTGCAGTGAATGATGCTCACTTGTTGCA
GTACAATCATCGGGTTAAAAAACTCAATGAAATCAGCAAACTGGGAATTTCTGGT
GACATAGACCTCACCAGTGCTTCATATACCATGATATAATCTGAAAGGGGCAGAT
TAAAAAAAAAAAAGAATCTAAACCTTACATGTGTAAAGGTTTCATGTTCACTGTG
AGTGAAAATTTTTACATTCATCAATATCCCTCTTGTAAGTCATCTACTTAATAAATA
TTACAGTGAATTACCTGTCTCAATATGTCAAAAAAAA AAAAAAAA
(SEQIDNO:3)

GenBank™ accession number NP_002297.2 galectin-3 isoform1 [Homosapiens]
MADNFSLHDALSGSGNPNPQGWPGAWGNQPAGAGGYPGASYPGA
YPGQAPPGAYPGQAPPGAYPGAPGAYPGAPAPGVYPGPPSGPGAYPSSGQPSA
TGAYPATGPYGAPAGPLIVPYNLPLGGVVPRMLITILGTVKPNANRIALDFQRGND
VAFHFNPRFNENNRRVIVCNTKLDNNWGREERQSVFPFESGKPFKIQVLVEPDHFK
VAVNDAHLLQYNHRVKKLNEISKLGISGDIDLTSASYTMI
(SEQIDNO:4)

SEQUENCE LISTING

<160> NUMBER OF SEQ ID NOS: 309

<210> SEQ ID NO 1
<211> LENGTH: 250
<212> TYPE: PRT
<213> ORGANISM: Homo sapiens

<400> SEQUENCE: 1

Met Ala Asp Asn Phe Ser Leu His Asp Ala Leu Ser Gly Ser Gly Asn
1               5                   10                  15

Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr Pro
    50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Thr Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Asn Thr Lys Leu Asp Asn Asn Trp Gly Arg Glu Glu Arg Gln Ser
1               5                   10                  15

Val Phe Pro Phe Glu Ser Gly
            20

<210> SEQ ID NO 3
<211> LENGTH: 1017
<212> TYPE: DNA

<213> ORGANISM: Homo sapiens

<400> SEQUENCE: 3

```
gagtatttga ggctcggagc caccgccccg ccggcgcccg cagcacctcc tcgccagcag      60
ccgtccggag ccagccaacg agcggaaaat ggcagacaat ttttcgctcc atgatgcgtt     120
atctgggtct ggaaacccaa accctcaagg atggcctggc catgggggga accagcctgc     180
tggggcaggg ggctacccag gggcttccta tcctggggcc tacccgggc aggcaccccc      240
aggggcttat cctggacagg cacctccagg cgcctaccct ggagcacctg agcttatcc      300
cggagcacct gcacctggag tctacccagg gccacccagc ggccctgggg cctacccatc     360
ttctggacag ccaagtgcca ccggagccta ccctgccact ggcccctatg gcgcccctgc     420
tgggccactg attgtgcctt ataacctgcc tttgcctggg ggagtggtgc ctcgcatgct     480
gataacaatt ctgggcacgg tgaagcccaa tgcaaacaga attgctttag atttccaaag     540
agggaatgat gttgccttcc actttaaccc acgcttcaat gagaacaaca ggagagtcat     600
tgtttgcaat acaaagctgg ataataactg gggaagggaa gaaagacagt cggttttccc     660
atttgaaagt gggaaaccat tcaaaataca agtactggtt gaacctgacc acttcaaggt     720
tgcagtgaat gatgctcact tgttgcagta caatcatcgg gttaaaaaac tcaatgaaat     780
cagcaaactg ggaatttctg gtgacataga cctcaccagt gcttcatata ccatgatata     840
atctgaaagg ggcagattaa aaaaaaaaaa agaatctaaa ccttacatgt gtaaaggttt     900
catgttcact gtgagtgaaa attttttacat tcatcaatat ccctcttgta agtcatctac     960
ttaataaata ttacagtgaa ttacctgtct caatatgtca aaaaaaaaaa aaaaaaa      1017
```

<210> SEQ ID NO 4
<211> LENGTH: 250
<212> TYPE: PRT
<213> ORGANISM: Homo sapiens

<400> SEQUENCE: 4

```
Met Ala Asp Asn Phe Ser Leu His Asp Ala Leu Ser Gly Ser Gly Asn
1               5                   10                  15

Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr Pro
    50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Thr Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175
```

```
Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250
```

```
<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Tyr Gly Val His
1               5

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Ile Trp Ser Asp Gly Ser Thr Thr Tyr Asn Ser Thr Leu Lys Ser
1               5                   10                  15

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Ile Ser Asn Tyr Gly Thr Met Asp Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Ser Gln Asp Ile Arg Asn Tyr Leu Asn
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 9

Tyr Thr Ser Arg Leu His Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln His Phe Asn Thr Leu Pro Pro Thr
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Phe Ser Leu Ser Ser Tyr
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Ser Asp Gly Ser
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

His Ile Ser Asn Tyr Gly Thr Met Asp Tyr
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ala Ser Gln Asp Ile Arg Asn Tyr Leu Asn
1               5                   10

<210> SEQ ID NO 15
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Thr Ser Arg Leu His Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln His Phe Asn Thr Leu Pro Pro Thr
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Phe Ser Leu Ser Ser Tyr Gly
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Trp Ser Asp Gly Ser Thr
1               5

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Arg His Ile Ser Asn Tyr Gly Thr Met Asp Tyr
1               5                   10

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Asp Ile Arg Asn Tyr
```

<210> SEQ ID NO 21
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Tyr Thr Ser
1

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln His Phe Asn Thr Leu Pro Pro Thr
1               5

<210> SEQ ID NO 23
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
caggtgcagc tgaaggagtc aggacctggc ctggtggcgc cctcacagag cctgtccatc      60
acatgcacca tctcagggtt ctcattaagt agttatggtg tacattgggt tcgccagcct     120
ccaggaaagg gtctggagtg gctggtagtg atatggagtg atggaagcac aacctataat     180
tcaactctca aatccagact gagcatcagc aaggacaact ccaagagcca gttttcttta     240
aaaatgaaca gtctccaaac tgatgacaca gccatgtact actgtgccag acatattagt     300
aactacggaa ctatggacta ctggggtcaa ggaacctcag tcaccgtctc c              351

<210> SEQ ID NO 24
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Ser Ser Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Thr Thr Tyr Asn Ser Thr Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
            85                  90                  95

Arg His Ile Ser Asn Tyr Gly Thr Met Asp Tyr Trp Gly Gln Gly Thr
            100                 105                 110

Ser Val Thr Val Ser
        115

<210> SEQ ID NO 25
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gatatccaga tgacacagac tacatcctcc ctgtctgcct ctctgggaga cagagtcacc    60
atcagttgca gggcaagtca ggacattagg aattatttaa actggtatca gcagaaacca   120
gatggatcta ttaaactcct gatctactac acatcaagat acactcagg agtcccatca    180 aggttcagtg cagtgggtc tggaacagat tattctctca ccattaggaa cctggagcaa    240
gaagatattg ccacttactt ttgccaacac tttaatacgc ttcctccgac gttcggtgga   300
ggcaccaagc tggaaatcaa a                                             321

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Asp Gly Ser Ile Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Arg Asn Leu Glu Gln
65                  70                  75                  80

Glu Asp Ile Ala Thr Tyr Phe Cys Gln His Phe Asn Thr Leu Pro Pro
                85                  90                  95

Thr Phe Gly Gly Gly Thr Lys Leu Glu Ile Lys
            100                 105

<210> SEQ ID NO 27
<211> LENGTH: 128
<212> TYPE: PRT
<213> ORGANISM: Homo sapiens

<400> SEQUENCE: 27

Pro Tyr Asn Leu Pro Leu Pro Gly Gly Val Val Pro Arg Met Leu Ile
1               5                   10                  15

Thr Ile Leu Gly Thr Val Lys Pro Asn Ala Asn Arg Ile Ala Leu Asp
            20                  25                  30

Phe Gln Arg Gly Asn Asp Val Ala Phe His Phe Asn Pro Arg Phe Asn

```
                35                  40                  45
Glu Asn Asn Arg Arg Val Ile Val Cys Asn Thr Lys Leu Asp Asn Asn
         50                  55                  60

Trp Gly Arg Glu Glu Arg Gln Ser Val Phe Pro Phe Glu Ser Gly Lys
 65                  70                  75                  80

Pro Phe Lys Ile Gln Val Leu Val Glu Pro Asp His Phe Lys Val Ala
                 85                  90                  95

Val Asn Asp Ala His Leu Leu Gln Tyr Asn His Arg Val Lys Lys Leu
            100                 105                 110

Asn Glu Ile Ser Lys Leu Gly Ile Ser Gly Asp Ile Asp Leu Thr Ser
        115                 120                 125

<210> SEQ ID NO 28
<211> LENGTH: 384
<212> TYPE: DNA
<213> ORGANISM: Homo sapiens

<400> SEQUENCE: 28
ccttataacc tgcctttgcc tgggggagtg gtgcctcgca tgctgataac aattctgggc    60
acggtgaagc ccaatgcaaa cagaattgct ttagatttcc aaagagggaa tgatgttgcc   120
ttccacttta acccacgctt caatgagaac aacaggagag tcattgtttg caatacaaag   180
ctggataata actggggaag gaagaaaga cagtcggttt tcccatttga agtgggaaa    240 ccattcaaaa tacaagtact ggttgaacct gaccacttca aggttgcagt gaatgatgct   300
cacttgttgc agtacaatca tcgggttaaa aaactcaatg aaatcagcaa actgggaatt   360
tctggtgaca tagacctcac cagt                                          384

<210> SEQ ID NO 29
<211> LENGTH: 812
<212> TYPE: DNA
<213> ORGANISM: Homo sapiens

<400> SEQUENCE: 29
ccggagccag ccaacgagcg gaaaatggca gacaattttt cgctccatga tgcgttatct    60
gggtctggaa acccaaaccc tcaaggatgg cctggcgcat gggggaacca gcctgctggg   120
gcagggggct acccaggggc ttcctatcct ggggcctacc ccgggcaggc accccagggg   180
gcttatcctg gacaggcacc tccaggcgcc taccctggag cacctggagc ttatcccgga   240
gcacctgcac ctggagtcta cccagggcca cccagcggcc ctgggccta cccatcttct    300 ggacagccaa gtgccaccgg agcctaccct gccactggcc cctatggcgc ccctgctggg   360
ccactgattg tgccttataa cctgcctttg cctgggggag tggtgcctcg catgctgata   420
acaattctgg gcacggtgaa gcccaatgca aacagaattg ctttagattt ccaaagaggg   480
aatgatgttg ccttccactt taacccacgc ttcaatgaga caacaggag agtcattgtt    540 tgcaatacaa agctggataa aactggggga agggaagaaa gacagtcggt tttcccattt   600
gaaagtggga aaccattcaa aatacaagta ctggttgaac ctgaccactt caaggttgca   660
gtgaatgatg ctcacttgtt gcagtacaat catcgggtta aaaaactcaa tgaaatcagc   720
aaactgggaa tttctggtga catagacctc accagtgctt catataccat gatataatct   780
gaaaggggca gattaaaaaa aaaaaaaaaa aa                                 812

<210> SEQ ID NO 30
<211> LENGTH: 4194
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 30

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgatatcggc catggttaga tctgacaaaa     660
ctcacacatg cccaccgtgc ccagcacctg aactcctggg gggaccgtca gtcttcctct     720
tccccccaaa acccaaggac accctcatga tctcccggac ccctgaggtc acatgcgtgg     780
tggtggacgt gagccacgaa gaccctgagg tcaagttcaa ctggtacgtg gacggcgtgg     840
aggtgcataa tgccaagaca aagccgcggg aggagcagta caacagcacg taccgtgtgg     900
tcagcgtcct caccgtcctg caccaggact ggctgaatgg caaggagtac aagtgcaagg     960
tctccaacaa agccctccca gcccccatcg agaaaaccat ctccaaagcc aaagggcagc    1020
cccgagaacc acaggtgtac accctgcccc catcccggga ggagatgacc aagaaccagg    1080
tcagcctgac ctgcctggtc aaaggcttct atcccagcga catcgccgtg gagtgggaga    1140
gcaatgggca gccggagaac aactacaaga ccacgcctcc cgtgctggac tccgacggct    1200
ccttcttcct ctacagcaag ctcaccgtgg acaagagcag gtggcagcag gggaacgtct    1260
tctcatgctc cgtgatgcac gaggctctgc acaaccacta cacgcagaag agcctctccc    1320
tgtctccggg taaatgagtg ctagctggcc agacatgata agatacattg atgagtttgg    1380
acaaaccaca actagaatgc agtgaaaaaa atgctttatt tgtgaaattt gtgatgctat    1440
tgctttattt gtaaccatta taagctgcaa taaacaagtt aacaacaaca attgcattca    1500
ttttatgttt caggttcagg gggaggtgtg ggaggttttt taaagcaagt aaaacctcta    1560
caaatgtggt atggaattaa ttctaaaata cagcatagca aactttaac ctccaaatca     1620 agcctctact tgaatccttt tctgagggat gaataaggca taggcatcag ggctgttgc     1680 caatgtgcat tagctgtttg cagcctcacc ttctttcatg gagtttaaga tatagtgtat    1740
tttcccaagg tttgaactag ctcttcattt ctttatgttt taaatgcact gacctcccac    1800
attccctttt tagtaaaata ttcagaaata atttaaatac atcattgcaa tgaaaataaa    1860
tgttttttat taggcagaat ccagatgctc aaggcccttc ataatatccc ccagtttagt    1920
agttggactt agggaacaaa ggaaccttta atagaaattg gacagcaaga aagcgagctt    1980
ctagcttatc ctcagtcctg ctcctctgcc acaaagtgca cgcagttgcc ggccgggtcg    2040
cgcagggcga actcccgccc ccacggctgc tcgccgatct cggtcatggc cggcccggag    2100
gcgtcccgga agttcgtgga cacgacctcc gaccactcgg cgtacagctc gtccaggccg    2160
```

| | | | | |
|---|---|---|---|---|
| cgcacccaca | cccaggccag | ggtgttgtcc | ggcaccacct | ggtcctggac cgcgctgatg | 2220 |
| aacagggtca | cgtcgtcccg | gaccacaccg | gcgaagtcgt | cctccacgaa gtcccgggag | 2280 |
| aacccgagcc | ggtcggtcca | gaactcgacc | gctccggcga | cgtcgcgcgc ggtgagcacc | 2340 |
| ggaacggcac | tggtcaactt | ggccatgatg | gctcctcctg | tcaggagagg aaagagaaga | 2400 |
| aggttagtac | aattgctata | gtgagttgta | ttatactatg | cagatatact atgccaatga | 2460 |
| ttaattgtca | aactagggct | gcaggggttca | tagtgccact | tttcctgcac tgccccatct | 2520 |
| cctgcccacc | ctttcccagg | catagacagt | cagtgactta | ccaaactcac aggagggaga | 2580 |
| aggcagaagc | ttgagacaga | cccgcgggac | cgccgaactg | cgaggggacg tggctagggc | 2640 |
| ggcttctttt | atggtgcgcc | ggccctcgga | ggcagggcgc | tcggggaggc ctagcggcca | 2700 |
| atctgcggtg | gcaggaggcg | gggccgaagg | ccgtgcctga | ccaatccgga gcacatagga | 2760 |
| gtctcagccc | cccgccccaa | agcaagggga | agtcacgcgc | ctgtagcgcc agcgtgttgt | 2820 |
| gaaatggggg | cttgggggggg | ttggggccct | gactagtcaa | aacaaactcc cattgacgtc | 2880 |
| aatgggggtgg | agacttggaa | atccccgtga | gtcaaaccgc | tatccacgcc cattgatgta | 2940 |
| ctgccaaaac | cgcatcatca | tggtaatagc | gatgactaat | acgtagatgt actgccaagt | 3000 |
| aggaaagtcc | cataaggtca | tgtactgggc | ataatgccag | gcgggccatt taccgtcatt | 3060 |
| gacgtcaata | gggggcgtac | ttggcatatg | atacacttga | tgtactgcca agtgggcagt | 3120 |
| ttaccgtaaa | tactccaccc | attgacgtca | atggaaagtc | cctattggcg ttactatggg | 3180 |
| aacatacgtc | attattgacg | tcaatgggcg | ggggtcgttg | ggcggtcagc caggcgggcc | 3240 |
| atttaccgta | agttatgtaa | cgcctgcagg | ttaattaaga | acatgtgagc aaaaggccag | 3300 |
| caaaaggcca | ggaaccgtaa | aaaggccgcg | ttgctggcgt | ttttccatag gctccgcccc | 3360 |
| cctgacgagc | atcacaaaaa | tcgacgctca | agtcagaggt | ggcgaaaccc gacaggacta | 3420 |
| taaagatacc | aggcgtttcc | ccctggaagc | tccctcgtgc | gctctcctgt tccgaccctg | 3480 |
| ccgcttaccg | gatacctgtc | cgcctttctc | ccttcgggaa | gcgtggcgct ttctcatagc | 3540 |
| tcacgctgta | ggtatctcag | ttcggtgtag | gtcgttcgct | ccaagctggg ctgtgtgcac | 3600 |
| gaaccccccg | ttcagcccga | ccgctgcgcc | ttatccggta | actatcgtct tgagtccaac | 3660 |
| ccggtaagac | acgacttatc | gccactggca | gcagccactg | gtaacaggat tagcagagcg | 3720 |
| aggtatgtag | gcggtgctac | agagttcttg | aagtggtggc | ctaactacgg ctacactaga | 3780 |
| agaacagtat | ttggtatctg | cgctctgctg | aagccagtta | ccttcggaaa aagagttggt | 3840 |
| agctcttgat | ccggcaaaca | aaccaccgct | ggtagcggtg | gtttttttgt ttgcaagcag | 3900 |
| cagattacgc | gcagaaaaaa | aggatctcaa | gaagatcctt | tgatcttttc tacggggtct | 3960 |
| gacgctcagt | ggaacgaaaa | ctcacgttaa | gggattttgg | tcatggctag ttaattaaca | 4020 |
| tttaaatcag | cggccgcaat | aaaatatctt | tattttcatt | acatctgtgt gttggttttt | 4080 |
| tgtgtgaatc | gtaactaaca | tacgctctcc | atcaaaacaa | aacgaaacaa aacaaactag | 4140 |
| caaaataggc | tgtccccagt | gcaagtgcag | gtgccagaac | atttctctat cgaa | 4194 |

<210> SEQ ID NO 31
<211> LENGTH: 379
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 31

```
Met Tyr Arg Met Gln Leu Leu Ser Cys Ile Ala Leu Ser Leu Ala Leu
1               5                   10                  15

Val Thr Asn Ser Pro Tyr Asn Leu Pro Leu Pro Gly Gly Val Val Pro
            20                  25                  30

Arg Met Leu Ile Thr Ile Leu Gly Thr Val Lys Pro Asn Ala Asn Arg
        35                  40                  45

Ile Ala Leu Asp Phe Gln Arg Gly Asn Asp Val Ala Phe His Phe Asn
    50                  55                  60

Pro Arg Phe Asn Glu Asn Asn Arg Arg Val Ile Val Cys Asn Thr Lys
65                  70                  75                  80

Leu Asp Asn Asn Trp Gly Arg Glu Glu Arg Gln Ser Val Phe Pro Phe
                85                  90                  95

Glu Ser Gly Lys Pro Phe Lys Ile Gln Val Leu Val Glu Pro Asp His
            100                 105                 110

Phe Lys Val Ala Val Asn Asp Ala His Leu Leu Gln Tyr Asn His Arg
        115                 120                 125

Val Lys Lys Leu Asn Glu Ile Ser Lys Leu Gly Ile Ser Gly Asp Ile
    130                 135                 140

Asp Leu Thr Ser Met Val Arg Ser Asp Lys Thr His Thr Cys Pro Pro
145                 150                 155                 160

Cys Pro Ala Pro Glu Leu Leu Gly Gly Pro Ser Val Phe Leu Phe Pro
                165                 170                 175

Pro Lys Pro Lys Asp Thr Leu Met Ile Ser Arg Thr Pro Glu Val Thr
            180                 185                 190

Cys Val Val Val Asp Val Ser His Glu Asp Pro Glu Val Lys Phe Asn
        195                 200                 205

Trp Tyr Val Asp Gly Val Glu Val His Asn Ala Lys Thr Lys Pro Arg
    210                 215                 220

Glu Glu Gln Tyr Asn Ser Thr Tyr Arg Val Val Ser Val Leu Thr Val
225                 230                 235                 240

Leu His Gln Asp Trp Leu Asn Gly Lys Glu Tyr Lys Cys Lys Val Ser
                245                 250                 255

Asn Lys Ala Leu Pro Ala Pro Ile Glu Lys Thr Ile Ser Lys Ala Lys
            260                 265                 270

Gly Gln Pro Arg Glu Pro Gln Val Tyr Thr Leu Pro Pro Ser Arg Glu
        275                 280                 285

Glu Met Thr Lys Asn Gln Val Ser Leu Thr Cys Leu Val Lys Gly Phe
    290                 295                 300

Tyr Pro Ser Asp Ile Ala Val Glu Trp Glu Ser Asn Gly Gln Pro Glu
305                 310                 315                 320

Asn Asn Tyr Lys Thr Thr Pro Pro Val Leu Asp Ser Asp Gly Ser Phe
                325                 330                 335

Phe Leu Tyr Ser Lys Leu Thr Val Asp Lys Ser Arg Trp Gln Gln Gly
            340                 345                 350

Asn Val Phe Ser Cys Ser Val Met His Glu Ala Leu His Asn His Tyr
        355                 360                 365

Thr Gln Lys Ser Leu Ser Leu Ser Pro Gly Lys
    370                 375

<210> SEQ ID NO 32
<211> LENGTH: 44
<212> TYPE: PRT
<213> ORGANISM: Homo sapiens

<400> SEQUENCE: 32
```

```
Gly Asn Asp Val Ala Phe His Phe Asn Pro Arg Phe Asn Glu Asn Asn
1               5                   10                  15

Arg Arg Val Ile Val Cys Asn Thr Lys Leu Asp Asn Asn Trp Gly Arg
            20                  25                  30

Glu Glu Arg Gln Ser Val Phe Pro Phe Glu Ser Gly
        35                  40
```

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Ser Tyr Gly Met Ser
1               5
```

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

```
Thr Ile Ser Ser Gly Gly Ser Tyr Thr Tyr Tyr Pro Asp Ser Val Lys
1               5                   10                  15

Gly
```

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Tyr Asp Gly Tyr Phe Val Gly Phe Thr Tyr
1               5                   10
```

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Ser Tyr Gly Met Ser
1               5
```

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Thr Ile Ser Ser Gly Gly Ser Tyr Thr Tyr Tyr Pro Asp Ser Val Lys
1               5                   10                  15

Gly

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Gly Ser Arg Tyr Asp Tyr Tyr Gly Met Asp Tyr
1               5                   10

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ser His Trp Met Tyr
1               5

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Ile Tyr Pro Gly Asn Ser Asp Thr Thr Tyr Asn Gln Lys Phe Lys
1               5                   10                  15

Gly

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asn Tyr Val Trp Tyr Phe Asp Val
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser His Trp Met Tyr
1               5

<210> SEQ ID NO 43
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Ile Tyr Pro Gly Asn Ser Asp Thr Thr Tyr Asn Gln Lys Phe Lys
1               5                   10                  15

Gly

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asn Tyr Val Trp Tyr Phe Asp Val
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Phe Ala Met Ser
1               5

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Ile Ser Thr Gly Gly Ser Tyr Thr Tyr Tyr Leu Asp Ser Gly Lys
1               5                   10                  15

Gly

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ala Gly Thr Gly Arg Leu Pro Ala Trp Phe Ala Tyr
1               5                   10

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                        peptide

<400> SEQUENCE: 48

Ser Tyr Gly Met Ser
1               5

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Ile Ser Ser Gly Gly Asn Tyr Ile Tyr Tyr Pro Asp Ser Val Lys
1               5                   10                  15

Gly

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Tyr Asp Gly Tyr Phe Val Gly Phe Thr Tyr
1               5                   10

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Tyr Gly Met Ser
1               5

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Ile Ser Ser Gly Gly Ser Tyr Thr Tyr Tyr Pro Asp Ser Val Lys
1               5                   10                  15

Gly

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Tyr Asp Gly Tyr Phe Val Gly Phe Thr Tyr
```

```
<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Tyr Gly Met Ser
1               5

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Ile Ser Ser Gly Gly Ser Tyr Thr Tyr Tyr Pro Asp Ser Val Lys
1               5                  10                  15

Gly

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Thr Val Gly Tyr Phe Asp Tyr
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ser Trp Met Tyr
1               5

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Ile Tyr Pro Gly Asn Ser Asp Thr Thr Tyr Asn Gln Lys Phe Lys
1               5                  10                  15

Gly

<210> SEQ ID NO 59
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asn Ser Gly Ala Met Asp Ser
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ser Tyr Gly Met Ser
1               5

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Ile Ser Ser Gly Gly Ser Tyr Ile Phe Tyr Pro Asp Ser Val Lys
1               5                   10                  15

Gly

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Tyr Asp Gly Tyr Phe Val Gly Phe Thr Tyr
1               5                   10

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Tyr Trp Ile His
1               5

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64
```

```
Thr Ile Asp Thr Ser Asp Ser Tyr Thr Tyr Asn Gln Lys Phe Lys
1               5                   10                  15
Asp

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Leu Arg Leu Arg Tyr Tyr Phe Glu Tyr
1               5                   10

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Tyr Tyr Ile His
1               5

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Ile Asn Pro Asn Asn Gly Asp Ser Ala Tyr Asn Gln Asn Phe Lys
1               5                   10                  15
Asp

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Gln Ile His Tyr Tyr Gly Met Asp Phe
1               5                   10

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Asp Tyr Thr Trp Asn
1               5
```

```
<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Tyr Ile Ser Tyr Ser Gly Ser Thr Ser Tyr Asn Pro Ser Leu Lys Ser
1               5                  10                  15

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ser Gly Tyr Ser Leu Tyr Thr Met Asp Tyr
1               5                  10

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Ala Ser Glu Asn Val Gly Thr Tyr Leu Ser
1               5                  10

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Thr Ser Asn Arg Phe Thr
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Gln Thr Leu Lys Tyr Pro His Thr
1               5

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75
```

```
Lys Ser Ser Gln Ser Leu Leu Asp Ser Asp Gly Lys Thr Tyr Leu Asn
1               5                   10                  15

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Val Ser Lys Val Asp Ser
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Trp Gln Gly Thr His Phe Pro Phe Thr
1               5

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys Ser Ser Gln Ser Leu Leu Asp Ser Asp Gly Lys Thr Tyr Leu Asn
1               5                   10                  15

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Val Ser Lys Val Asp Ser
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Trp Gln Gly Thr His Phe Pro Phe Thr
1               5

<210> SEQ ID NO 81
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 81

Arg Ala Ser Glu Asn Ile Tyr Ser Tyr Leu Ala
1               5                   10

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asn Ala Lys Thr Leu Ala Glu
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln His His Tyr Gly Thr Pro Trp Thr
1               5

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Ala Ser Gln Ser Ile Gly Asn Asn Leu His
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Tyr Ala Ser Gln Ser Ile Ser
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Gln Thr Asn Ile Trp Pro Tyr Thr
1               5
```

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Ser Ser Thr Gly Ala Val Ile Thr Ser Asn Tyr Ala Asn
1               5                   10

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Thr Asn Asn Arg Ala Pro
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Leu Arg Tyr Ser Asn His Trp Val
1               5

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Thr Ala Ser Ser Ser Val Ser Ser Ser Tyr Leu His
1               5                   10

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ser Thr Ser Asn Leu Ala Ser
1               5

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 92

His Gln Tyr His Arg Ser Pro Pro Ile Thr
1               5                   10

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Ser Arg Gln Ser Leu Leu Asp Ser Asp Gly Lys Thr Tyr Leu Asn
1               5                   10                  15

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Leu Val Ser Lys Leu Asp Ser
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Trp Gln Gly Thr His Phe Pro Trp Thr
1               5

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Ala Ser Glu Asn Ile Tyr Ser Tyr Leu Ala
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asn Ala Lys Thr Leu Ala Glu
1               5

<210> SEQ ID NO 98
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 98

Gln His His Tyr Gly Thr Pro Trp Thr
1               5

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Ser Ser Thr Gly Ala Val Thr Thr Ser Asn Tyr Ala Asn
1               5                   10

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Thr Asn Asn Arg Ala Pro
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Val Leu Arg Tyr Ser Asn His Trp Val
1               5

<210> SEQ ID NO 102
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Ser Ser Thr Gly Ala Val Thr Thr Ser Asn Tyr Ala Asn
1               5                   10

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asp Thr Asn Asn Arg Ala Pro
1               5
```

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ala Leu Trp Tyr Asn Asn His Ser Trp Val
1               5                   10

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Phe Thr Phe Ser Ser Tyr
1               5

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Ser Gly Gly Ser Tyr
1               5

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Tyr Asp Gly Tyr Phe Val Gly Phe Thr Tyr
1               5                   10

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Phe Thr Phe Ser Ser Tyr
1               5

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 109

Ser Ser Gly Gly Ser Tyr
1               5

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Leu Gly Ser Arg Tyr Asp Tyr Tyr Gly Met Asp Tyr
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Lys Ala Ser Glu Asn Val Gly Thr Tyr Leu Ser
1               5                   10

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Thr Ser Asn Arg Phe Thr
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Gln Thr Leu Lys Tyr Pro His Thr
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Tyr Thr Phe Thr Ser His
1               5

<210> SEQ ID NO 115
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Tyr Pro Gly Asn Ser Asp
1               5

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asn Tyr Val Trp Tyr Phe Asp Val
1               5

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Lys Ser Ser Gln Ser Leu Leu Asp Ser Asp Gly Lys Thr Tyr Leu Asn
1               5                   10                  15

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Leu Val Ser Lys Val Asp Ser
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Trp Gln Gly Thr His Phe Pro Phe Thr
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Tyr Thr Phe Thr Ser His
```

```
<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Tyr Pro Gly Asn Ser Asp
1               5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Asn Tyr Val Trp Tyr Phe Asp Val
1               5

<210> SEQ ID NO 123
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Lys Ser Ser Gln Ser Leu Leu Asp Ser Asp Gly Lys Thr Tyr Leu Asn
1               5                   10                  15

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Leu Val Ser Lys Val Asp Ser
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Trp Gln Gly Thr His Phe Pro Phe Thr
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 126

Gly Phe Thr Phe Ser Ser Pro
1               5

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ser Thr Gly Gly Ser Tyr
1               5

<210> SEQ ID NO 128
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Arg Ala Gly Thr Gly Arg Leu Pro Ala Trp Phe Ala Tyr
1               5                   10

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Phe Thr Phe Ser Ser Tyr
1               5

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ser Ser Gly Gly Asn Tyr
1               5

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Tyr Asp Gly Tyr Phe Val Gly Phe Thr Tyr
1               5                   10

<210> SEQ ID NO 132
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Arg Ala Ser Glu Asn Ile Tyr Ser Tyr Leu Ala
1               5                   10

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asn Ala Lys Thr Leu Ala Glu
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gln His His Tyr Gly Thr Pro Trp Thr
1               5

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Phe Thr Phe Ser Ser Tyr
1               5

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ser Ser Gly Gly Ser Tyr
1               5

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137
```

Tyr Asp Gly Tyr Phe Val Gly Phe Thr Tyr
1               5                   10

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Phe Thr Phe Ser Ser Tyr
1               5

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ser Ser Gly Gly Ser Tyr
1               5

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Tyr Asp Gly Tyr Phe Val Gly Phe Thr Tyr
1               5                   10

<210> SEQ ID NO 141
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Arg Ser Ser Thr Gly Ala Val Thr Thr Ser Asn Tyr Ala Asn
1               5                   10

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Thr Asn Asn Arg Ala Pro
1               5

<210> SEQ ID NO 143
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 143

Ala Leu Arg Tyr Ser Asn His Trp Val
1               5

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Phe Thr Phe Ser Ser Tyr
1               5

<210> SEQ ID NO 145
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Ser Gly Gly Ser Tyr
1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gln Thr Val Gly Tyr Phe Asp Tyr
1               5

<210> SEQ ID NO 147
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Thr Ala Ser Ser Ser Val Ser Ser Ser Tyr Leu His
1               5                   10

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Thr Ser Asn Leu Ala Ser
1               5
```

```
<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

His Gln Tyr His Arg Ser Pro Pro Ile Thr
1               5                   10

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Tyr Thr Phe Thr Arg Ser
1               5

<210> SEQ ID NO 151
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Tyr Pro Gly Asn Ser Asp
1               5

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asn Ser Gly Ala Met Asp Ser
1               5

<210> SEQ ID NO 153
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Lys Ser Arg Gln Ser Leu Leu Asp Ser Asp Gly Lys Thr Tyr Leu Asn
1               5                   10                  15

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154
```

```
Leu Val Ser Lys Leu Asp Ser
1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Trp Gln Gly Thr His Phe Pro Trp Thr
1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Phe Thr Phe Ser Ser Tyr
1               5

<210> SEQ ID NO 157
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ser Ser Gly Gly Ser Tyr
1               5

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Tyr Asp Gly Tyr Phe Val Gly Phe Thr Tyr
1               5                   10

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Arg Ala Ser Glu Asn Ile Tyr Ser Tyr Leu Ala
1               5                   10

<210> SEQ ID NO 160
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 160

Asn Ala Lys Thr Leu Ala Glu
1               5

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gln His His Tyr Gly Thr Pro Trp Thr
1               5

<210> SEQ ID NO 162
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Arg Ser Ser Thr Gly Ala Val Thr Thr Ser Asn Tyr Ala Asn
1               5                   10

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Thr Asn Asn Arg Ala Pro
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Val Leu Arg Tyr Ser Asn His Trp Val
1               5

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gly Tyr Thr Phe Ser Asp Tyr
1               5
```

<210> SEQ ID NO 166
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Asp Thr Ser Asp Ser Tyr
1               5

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Leu Leu Arg Leu Arg Tyr Tyr Phe Glu Tyr
1               5                   10

<210> SEQ ID NO 168
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Arg Ser Ser Thr Gly Ala Val Thr Thr Ser Asn Tyr Ala Asn
1               5                   10

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Asp Thr Asn Asn Arg Ala Pro
1               5

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ala Leu Trp Tyr Asn Asn His Ser Trp Val
1               5                   10

<210> SEQ ID NO 171
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 171

Gly Tyr Ser Phe Thr Asp Tyr Tyr
1               5

<210> SEQ ID NO 172
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Asn Pro Asn Asn Gly Asp
1               5

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Arg Gln Ile His Tyr Tyr Gly Met Asp Phe
1               5                   10

<210> SEQ ID NO 174
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Tyr Ser Ile Thr Ser Asp Tyr
1               5

<210> SEQ ID NO 175
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Tyr Ser Gly Ser
1               5

<210> SEQ ID NO 176
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Ser Gly Tyr Ser Leu Tyr Thr Met Asp Tyr
1               5                   10

<210> SEQ ID NO 177
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 177

Gly Phe Thr Phe Ser Ser Tyr Gly
1               5

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ile Ser Ser Gly Gly Ser Tyr Thr
1               5

<210> SEQ ID NO 179
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ala Asn Tyr Asp Gly Tyr Phe Val Gly Phe Thr Tyr
1               5                   10

<210> SEQ ID NO 180
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Phe Thr Phe Ser Ser Tyr Gly
1               5

<210> SEQ ID NO 181
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ile Ser Ser Gly Gly Ser Tyr Thr
1               5

<210> SEQ ID NO 182
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ala Arg Leu Gly Ser Arg Tyr Asp Tyr Tyr Gly Met Asp Tyr
1               5                   10
```

<210> SEQ ID NO 183
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Glu Asn Val Gly Thr Tyr
1               5

<210> SEQ ID NO 184
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gly Thr Ser
1

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Gln Thr Leu Lys Tyr Pro His Thr
1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gly Tyr Thr Phe Thr Ser His Trp
1               5

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ile Tyr Pro Gly Asn Ser Asp Thr
1               5

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Asn Ser Asn Tyr Val Trp Tyr Phe Asp Val
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gln Ser Leu Leu Asp Ser Asp Gly Lys Thr Tyr
1               5                   10

<210> SEQ ID NO 190
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Leu Val Ser
1

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Trp Gln Gly Thr His Phe Pro Phe Thr
1               5

<210> SEQ ID NO 192
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Tyr Thr Phe Thr Ser His Trp
1               5

<210> SEQ ID NO 193
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ile Tyr Pro Gly Asn Ser Asp Thr
1               5

<210> SEQ ID NO 194
<211> LENGTH: 10

```
-continued

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Asn Ser Asn Tyr Val Trp Tyr Phe Asp Val
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gln Ser Leu Leu Asp Ser Asp Gly Lys Thr Tyr
1               5                   10

<210> SEQ ID NO 196
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Leu Val Ser
1

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Trp Gln Gly Thr His Phe Pro Phe Thr
1               5

<210> SEQ ID NO 198
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gly Phe Thr Phe Ser Ser Pro Ala
1               5

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ile Ser Thr Gly Gly Ser Tyr Thr
```

```
<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Val Ser Arg Ala Gly Thr Gly Arg Leu Pro Ala Trp Phe Ala Tyr
1               5                   10                  15

<210> SEQ ID NO 201
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Phe Thr Phe Ser Ser Tyr Gly
1               5

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ile Ser Ser Gly Gly Asn Tyr Ile
1               5

<210> SEQ ID NO 203
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ala Asn Tyr Asp Gly Tyr Phe Val Gly Phe Thr Tyr
1               5                   10

<210> SEQ ID NO 204
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Glu Asn Ile Tyr Ser Tyr
1               5

<210> SEQ ID NO 205
<211> LENGTH: 3
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 205

Asn Ala Lys
1

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gln His His Tyr Gly Thr Pro Trp Thr
1               5

<210> SEQ ID NO 207
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gly Phe Thr Phe Ser Ser Tyr Gly
1               5

<210> SEQ ID NO 208
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ile Ser Ser Gly Gly Ser Tyr Thr
1               5

<210> SEQ ID NO 209
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ala Asn Tyr Asp Gly Tyr Phe Val Gly Phe Thr Tyr
1               5                   10

<210> SEQ ID NO 210
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gln Ser Ile Gly Asn Asn
1               5

<210> SEQ ID NO 211

```
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Tyr Ala Ser
1

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gln Gln Thr Asn Ile Trp Pro Tyr Thr
1               5

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Thr Gly Ala Val Thr Thr Ser Asn Tyr
1               5

<210> SEQ ID NO 214
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Thr Asn
1

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ala Leu Arg Tyr Ser Asn His Trp Val
1               5

<210> SEQ ID NO 216
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216
```

```
Gly Phe Thr Phe Ser Ser Tyr Gly
1               5
```

<210> SEQ ID NO 217
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

```
Ile Ser Ser Gly Gly Ser Tyr Thr
1               5
```

<210> SEQ ID NO 218
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

```
Ala Arg Gln Thr Val Gly Tyr Phe Asp Tyr
1               5                   10
```

<210> SEQ ID NO 219
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

```
Ser Ser Val Ser Ser Ser Tyr
1               5
```

<210> SEQ ID NO 220
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

```
Ser Thr Ser
1
```

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

```
His Gln Tyr His Arg Ser Pro Pro Ile Thr
1               5                   10
```

<210> SEQ ID NO 222
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 222

Gly Tyr Thr Phe Thr Arg Ser Trp
1               5

<210> SEQ ID NO 223
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ile Tyr Pro Gly Asn Ser Asp Thr
1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Asn Thr Asn Ser Gly Ala Met Asp Ser
1               5

<210> SEQ ID NO 225
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gln Ser Leu Leu Asp Ser Asp Gly Lys Thr Tyr
1               5                   10

<210> SEQ ID NO 226
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Leu Val Ser
1

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Trp Gln Gly Thr His Phe Pro Trp Thr
1               5
```

```
<210> SEQ ID NO 228
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gly Phe Thr Phe Ser Ser Tyr Gly
1               5

<210> SEQ ID NO 229
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ile Ser Ser Gly Gly Ser Tyr Ile
1               5

<210> SEQ ID NO 230
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ala Asn Tyr Asp Gly Tyr Phe Val Gly Phe Thr Tyr
1               5                   10

<210> SEQ ID NO 231
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Glu Asn Ile Tyr Ser Tyr
1               5

<210> SEQ ID NO 232
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Asn Ala Lys
1

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233
```

```
Gln His His Tyr Gly Thr Pro Trp Thr
1               5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Thr Gly Ala Val Thr Thr Ser Asn Tyr
1               5

<210> SEQ ID NO 235
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gly Thr Asn
1

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Val Leu Arg Tyr Ser Asn His Trp Val
1               5

<210> SEQ ID NO 237
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gly Tyr Thr Phe Ser Asp Tyr Trp
1               5

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ile Asp Thr Ser Asp Ser Tyr Thr
1               5

<210> SEQ ID NO 239
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 239

Ala Thr Leu Leu Arg Leu Arg Tyr Tyr Phe Glu Tyr
1               5                   10

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Thr Gly Ala Val Thr Thr Ser Asn Tyr
1               5

<210> SEQ ID NO 241
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Asp Thr Asn
1

<210> SEQ ID NO 242
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ala Leu Trp Tyr Asn Asn His Ser Trp Val
1               5                   10

<210> SEQ ID NO 243
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Gly Tyr Ser Phe Thr Asp Tyr Tyr
1               5

<210> SEQ ID NO 244
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ile Asn Pro Asn Asn Gly Asp Ser
1               5
```

<210> SEQ ID NO 245
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ala Arg Arg Gln Ile His Tyr Tyr Gly Met Asp Phe
1               5                   10

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Tyr Ser Ile Thr Ser Asp Tyr Thr
1               5

<210> SEQ ID NO 247
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Ile Ser Tyr Ser Gly Ser Thr
1               5

<210> SEQ ID NO 248
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ala Arg Gly Ser Gly Tyr Ser Leu Tyr Thr Met Asp Tyr
1               5                   10

<210> SEQ ID NO 249
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 249
gaggtgcagc tggtggagtc tgggggagac ttagtgaagc ctggagggtc cctgaaactc      60
tcctgtgcag cctctggatt cactttcagt agctatggca tgtcttgggt tcgccagact     120
ccagacaaga ggctggagtg gtcgcaacc attagtagtg gtggtagtta cacctactat     180
ccagacagtg tgaaggggcg attcaccatc tccagagaca atgccaagaa caccctgtac     240
ctgcaaatga gtagtctgaa gtctgaggac acagccatgt attcctgtgc aaactatgat     300
ggttacttcg tcgggtttac ttactggggc caaggggactc tggtcactgt ctctgca     357

<210> SEQ ID NO 250
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Ser Cys
                85                  90                  95

Ala Asn Tyr Asp Gly Tyr Phe Val Gly Phe Thr Tyr Trp Gly Gln Gly
            100                 105                 110

Thr Leu Val Thr Val Ser Ala
        115

<210> SEQ ID NO 251
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 251
gaggtgcagc tggtggagtc tgggggagac ttagtgaagc ctggagggtc cctgaaactc      60
tcctgtgcag cctctggatt cactttcagt agctatggca tgtcttgggt tcgccagact     120
ccagacaaga ggctggagtg ggtcgcaacc attagtagtg gtggtagtta cacctactat     180
ccagacagtg tgaaggggcg attcaccatc tccagagaca tgccaagaa caccctgtac      240 ctgcaaatga gcagtctgaa gtctgaggac acagccatgt attactgtgc aagactcggt     300
agtaggtacg attactatgg tatggactac tggggtcaag gaacctcagt caccgtctcc     360
tca                                                                    363

<210> SEQ ID NO 252
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

-continued

```
Ala Thr Ile Ser Ser Gly Gly Ser Tyr Thr Tyr Tyr Pro Asp Ser Val
        50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                85                  90                  95

Ala Arg Leu Gly Ser Arg Tyr Asp Tyr Gly Met Asp Tyr Trp Gly
            100                 105                 110

Gln Gly Thr Ser Val Thr Val Ser Ser
            115                 120
```

<210> SEQ ID NO 253
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 253

```
caggtccagc tgcagcagtc tgcagctgaa ctggcaagac ctggggcctc agtgaagatg      60
tcctgcaagg cttctggcta cacctttact acctacgcga tgcactggtt aaaacagagg     120
cctggacagg gtctggaatg gcttggatac attaatccta gcagtggata cattgaatat     180
aatcagaagt tcaaggacaa gaccacattg actgcagaca atcttccag cacagcctac     240 atgcaactga gcagcctgac atctgaggac tctgcggtct attactgtgc aagacactgg     300
ggtgcttact ggggccaagg gactctggtc actgtttctg ca                        342
```

<210> SEQ ID NO 254
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

```
Gln Val Gln Leu Gln Gln Ser Ala Ala Glu Leu Ala Arg Pro Gly Ala
 1               5                  10                  15

Ser Val Lys Met Ser Cys Lys Ala Ser Gly Tyr Thr Phe Thr Thr Tyr
            20                  25                  30

Ala Met His Trp Leu Lys Gln Arg Pro Gly Gln Gly Leu Glu Trp Leu
        35                  40                  45

Gly Tyr Ile Asn Pro Ser Ser Gly Tyr Ile Glu Tyr Asn Gln Lys Phe
    50                  55                  60

Lys Asp Lys Thr Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg His Trp Gly Ala Tyr Trp Gly Gln Gly Thr Leu Val Thr Val
            100                 105                 110

Ser Ala
```

<210> SEQ ID NO 255
<211> LENGTH: 322
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 255

```
gacattgtga tgacccagtc tcaaaaattc atgtccacat cagtaggaga cagggtcagc    60
gtcacctgca aggccagtca gagtgtgggt actaatgtag cctggtatca acagaaacca   120
ggacaatctc ctaaagcact gatttactcg gcatcttatc gatacagtgg agtccctgat   180
cgcttcacag gccgtggatc tgggacagat ttcactctca ccatcaccag tgtgcagtct   240
gaagacttgg caaagtatgt ctgtcagcaa tatttcaact atccgctcac gttcggtgct   300
gggaccaagc tggagctgaa ac                                             322
```

<210> SEQ ID NO 256
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 256

```
Asp Ile Val Met Thr Gln Ser Gln Lys Phe Met Ser Thr Ser Val Gly
1               5                   10                  15
Asp Arg Val Ser Val Thr Cys Lys Ala Ser Gln Ser Val Gly Thr Asn
            20                  25                  30
Val Ala Trp Tyr Gln Gln Lys Pro Gly Gln Ser Pro Lys Ala Leu Ile
        35                  40                  45
Tyr Ser Ala Ser Tyr Arg Tyr Ser Gly Val Pro Asp Arg Phe Thr Gly
    50                  55                  60
Arg Gly Ser Gly Thr Asp Phe Thr Leu Thr Ile Thr Ser Val Gln Ser
65                  70                  75                  80
Glu Asp Leu Ala Lys Tyr Val Cys Gln Gln Tyr Phe Asn Tyr Pro Leu
                85                  90                  95
Thr Phe Gly Ala Gly Thr Lys Leu Glu Leu Lys
            100                 105
```

<210> SEQ ID NO 257
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 257

```
gaggttcagc tccagcagtc tgggactgta gtggcaaggc ctggggcttc agtgaagatg    60
tcctgcaagg cttctggcta cacctttacc agccactgga tgtactgggt aaaacagagg   120
cctggacagg gtctggaatg gattggcgct atttatcctg gaaatagtga tactacctac   180
aaccagaagt tcaagggcaa ggccaaactg actgcagtca catccaccag cactgcctac   240
atggagctca gcagcctgac aaatgaggac tctgcggtct attactgtaa cagtaactac   300
gtctggtact cgatgtctg gggcgcaggg accacggtcg ccgtctcctc a             351
```

<210> SEQ ID NO 258
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 258

Glu Val Gln Leu Gln Gln Ser Gly Thr Val Ala Arg Pro Gly Ala
1               5                   10                  15

Ser Val Lys Met Ser Cys Lys Ala Ser Gly Tyr Thr Phe Thr Ser His
            20                  25                  30

Trp Met Tyr Trp Val Lys Gln Arg Pro Gly Gln Gly Leu Glu Trp Ile
        35                  40                  45

Gly Ala Ile Tyr Pro Gly Asn Ser Asp Thr Thr Tyr Asn Gln Lys Phe
    50                  55                  60

Lys Gly Lys Ala Lys Leu Thr Ala Val Thr Ser Thr Ser Thr Ala Tyr
65                  70                  75                  80

Met Glu Leu Ser Ser Leu Thr Asn Glu Asp Ser Ala Val Tyr Tyr Cys
                85                  90                  95

Asn Ser Asn Tyr Val Trp Tyr Phe Asp Val Trp Gly Ala Gly Thr Thr
                100                 105                 110

Val Ala Val Ser Ser
            115

<210> SEQ ID NO 259
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 259
gatgttgtga tgacccagac tccactcact ttgtcggtta cctttggaca accagccgcc     60
atctcttgca agtcaagtca gagcctctta gatagtgatg gaaagacata tttgaattgg    120
ttgtcacaga ggccaggcca gtctccaaag cgcctcatct atctggtgtc taaagtggac    180
tctggagtcc ctgacaggtt cactggcagt ggatcaggga cagatttcac actgaaaatc    240
agcagagtgg aggctgagga tttgggagtt tattattgct ggcaaggtac gcattttcca    300
ttcacattcg gctcggggac aaagttggaa ataaaac                             337

<210> SEQ ID NO 260
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Asp Val Val Met Thr Gln Thr Pro Leu Thr Leu Ser Val Thr Phe Gly
1               5                   10                  15

Gln Pro Ala Ala Ile Ser Cys Lys Ser Ser Gln Ser Leu Leu Asp Ser
            20                  25                  30

Asp Gly Lys Thr Tyr Leu Asn Trp Leu Ser Gln Arg Pro Gly Gln Ser
        35                  40                  45

Pro Lys Arg Leu Ile Tyr Leu Val Ser Lys Val Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

```
Thr His Phe Pro Phe Thr Phe Gly Ser Gly Thr Lys Leu Glu Ile Lys
            100                 105                 110
```

<210> SEQ ID NO 261
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 261

```
gaggttcagc tccagcagtc tgggactgta gtggcaaggc ctggggcttc agtgaagatg    60
tcctgcaagg cttctggcta cacctttacc agccactgga tgtactgggt aaaacagagg   120
cctggacagg gtctggaatg gattggcgct atttatcctg gaaatagtga tactacctac   180
aaccagaagt tcaagggcaa ggccaaactg actgcagtca catccaccag cactgcctac   240
atggagctca gcagcctgac aaatgaggac tctgcggtct attactgtaa cagtaactac   300
gtctggtact tcgatgtctg gggcgcaggg accacggtcg ccgtctcctc a            351
```

<210> SEQ ID NO 262
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

```
Glu Val Gln Leu Gln Gln Ser Gly Thr Val Val Ala Arg Pro Gly Ala
1               5                   10                  15

Ser Val Lys Met Ser Cys Lys Ala Ser Gly Tyr Thr Phe Thr Ser His
            20                  25                  30

Trp Met Tyr Trp Val Lys Gln Arg Pro Gly Gln Gly Leu Glu Trp Ile
        35                  40                  45

Gly Ala Ile Tyr Pro Gly Asn Ser Asp Thr Thr Tyr Asn Gln Lys Phe
    50                  55                  60

Lys Gly Lys Ala Lys Leu Thr Ala Val Thr Ser Thr Ser Thr Ala Tyr
65                  70                  75                  80

Met Glu Leu Ser Ser Leu Thr Asn Glu Asp Ser Ala Val Tyr Tyr Cys
                85                  90                  95

Asn Ser Asn Tyr Val Trp Tyr Phe Asp Val Trp Gly Ala Gly Thr Thr
            100                 105                 110

Val Ala Val Ser Ser
        115
```

<210> SEQ ID NO 263
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 263

```
gatgttgtga tgacccagac tccactcact ttgtcggtta cctttggaca accagccgcc    60
atctcttgca gtcaagtca gagcctctta gatagtgatg gaaagacata tttgaattgg   120
ttgtcacaga ggccaggcca gtctccaaag cgcctcatct atctggtgtc taaagtggac   180
```

```
tctggagtcc ctgacaggtt cactggcagt ggatcaggga cagatttcac actgaaaatc    240
agcagagtgg aggctgagga tttgggagtt tattattgct ggcaaggtac gcattttcca    300
ttcacattcg gctcggggac aaagttggaa ataaaac                             337
```

<210> SEQ ID NO 264
<211> LENGTH: 112
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 264

```
Asp Val Val Met Thr Gln Thr Pro Leu Thr Leu Ser Val Thr Phe Gly
1               5                   10                  15

Gln Pro Ala Ala Ile Ser Cys Lys Ser Gln Ser Leu Leu Asp Ser
            20                  25                  30

Asp Gly Lys Thr Tyr Leu Asn Trp Leu Ser Gln Arg Pro Gly Gln Ser
        35                  40                  45

Pro Lys Arg Leu Ile Tyr Leu Val Ser Lys Val Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Phe Thr Phe Gly Ser Gly Thr Lys Leu Glu Ile Lys
                100                 105                 110
```

<210> SEQ ID NO 265
<211> LENGTH: 366
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 265

```
gaagtgctgt tggtggagtc tgggggaggc tttgtgaggc ctggagggtc cctaaaactc    60
tcctgtatag cctctggatt cactttcagt agttttgcca tgtcttgggt tcgccagact   120
ccggagaaga ggctggagtg ggtcgcaacc attagtaccg gtggttctta cacctactat   180
ttagacagtg gaaggggcg attcaccatc tccagagaca atgccaagaa caccctgtac   240
ctgcaaatga ccagtctgag gtctgaggac acggccatgt attactgtgt aagtcgagct   300
gggacgggac gcctcccggc ctggtttgct tactggggcc aagggactct ggtcactgtc   360
tctgca                                                               366
```

<210> SEQ ID NO 266
<211> LENGTH: 122
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 266

```
Glu Val Leu Leu Val Glu Ser Gly Gly Gly Phe Val Arg Pro Gly Gly
1               5                   10                  15

Ser Leu Lys Leu Ser Cys Ile Ala Ser Gly Phe Thr Phe Ser Ser Phe
            20                  25                  30
```

Ala Met Ser Trp Val Arg Gln Thr Pro Glu Lys Arg Leu Glu Trp Val
         35                  40                  45

Ala Thr Ile Ser Thr Gly Gly Ser Tyr Thr Tyr Tyr Leu Asp Ser Gly
     50                  55                  60

Lys Gly Arg Phe Thr Ile Ser Arg Asp Asn Ala Lys Asn Thr Leu Tyr
 65                  70                  75                  80

Leu Gln Met Thr Ser Leu Arg Ser Glu Asp Thr Ala Met Tyr Tyr Cys
             85                  90                  95

Val Ser Arg Ala Gly Thr Gly Arg Leu Pro Ala Trp Phe Ala Tyr Trp
            100                 105                 110

Gly Gln Gly Thr Leu Val Thr Val Ser Ala
            115                 120

<210> SEQ ID NO 267
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 267
gaggtgcagc tggtggagtc tgggggagac ttagtgaagc ctggagggtc cctgaaactc        60
tcctgtgcag cctctggatt cactttcagt agctatggca tgtcttgggt tcgccagact       120
ccagacaaga ggctggagtg ggtcgcaacc attagcagtg gtggtaatta tatctattat       180
ccagacagtg tgaaggggcg attcaccatc tccagagaca tgccaagaa cacccctgtac       240 ctgcaaatga gcagtctgag gtctgaggac acagccatgt attactgtgc aaactatgat       300
ggttacttcg tcggctttac ttactggggc caagggactc tggtcactgt ctctgca         357

<210> SEQ ID NO 268
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Glu Val Gln Leu Val Glu Ser Gly Gly Asp Leu Val Lys Pro Gly Gly
  1               5                  10                  15

Ser Leu Lys Leu Ser Cys Ala Ala Ser Gly Phe Thr Phe Ser Ser Tyr
             20                  25                  30

Gly Met Ser Trp Val Arg Gln Thr Pro Asp Lys Arg Leu Glu Trp Val
         35                  40                  45

Ala Thr Ile Ser Ser Gly Gly Asn Tyr Ile Tyr Tyr Pro Asp Ser Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Met Tyr Tyr Cys
             85                  90                  95

Ala Asn Tyr Asp Gly Tyr Phe Val Gly Phe Thr Tyr Trp Gly Gln Gly
            100                 105                 110

Thr Leu Val Thr Val Ser Ala
        115

<210> SEQ ID NO 269

<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 269
gacatccaga tgactcagtc tccagcctcc ctatctgcat ctgtgggaga aactgtcacc      60
atcacatgtc gagcaagtga gaatatttac agttatttag catggtatca gcagaaacag     120
ggaaaatctc ctcagctcct ggtcagaaat gcaaaaacct agcagaagg tgtgtcatca     180 agattcagtg gcagtggatc aggcacacag ttttctctga agatcaacag cctgcagcct    240
gaagattttg ggagttatta ctgtcaacat cattatggta ctccgtggac gttcggtgga    300
ggcaccaagc tggaaatcaa ac                                             322

<210> SEQ ID NO 270
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Arg Asn Ala Lys Thr Leu Ala Glu Gly Val Ser Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Trp
                85                  90                  95

Thr Phe Gly Gly Gly Thr Lys Leu Glu Ile Lys
            100                 105

<210> SEQ ID NO 271
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 271
gaggtgcagc tggtggagtc tgggggagac ttagtgaagc ctggagggtc cctgaaactc      60
tcctgtgcag cctctggatt cactttcagt agctatggca tgtcttgggt tcgccagact     120
ccagacaaga ggctggagtg gtcgcaacc attagtagtg gtggtagtta cacctactat     180
ccagacagtg tgaaggggcg attcaccatc tccagagaca atgccaagaa caccctgtac    240
ctgcaaatga gtagtctgaa gtctgaggac acagccatgt attcctgtgc aaactatgat    300
ggttacttcg tcgggtttac ttactggggc caaggactc tggtcactgt ctctgca       357

<210> SEQ ID NO 272
<211> LENGTH: 119

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Glu Val Gln Leu Val Glu Ser Gly Gly Asp Leu Val Lys Pro Gly Gly
 1               5                  10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Ser Cys
                85                  90                  95

Ala Asn Tyr Asp Gly Tyr Phe Val Gly Phe Thr Tyr Trp Gly Gln Gly
            100                 105                 110

Thr Leu Val Thr Val Ser Ala
        115

<210> SEQ ID NO 273
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 273
gatattgtgc taactcagtc tccagccacc ctgtctgtga ctccaggaga tagcgtcagt     60
ctttcctgca gggccagcca agtattggc aacaacctac actggtatca acagaaatca    120
catgagtctc caaggcttct catcaagtat gcttcccagt ccatctctgg atccccctcc    180
aggttcagtg gcagtggatc aggacagat ttcactctca ttatcaatag tgtggagact    240
gaagattttg gaatgtattt ctgtcaacag actaacatct ggccgtacac gttcggaggg    300
gggaccaagc tggagctgaa ac                                             322

<210> SEQ ID NO 274
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Asp Ile Val Leu Thr Gln Ser Pro Ala Thr Leu Ser Val Thr Pro Gly
 1               5                  10                  15

Asp Ser Val Ser Leu Ser Cys Arg Ala Ser Gln Ser Ile Gly Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ile Ile Asn Ser Val Glu Thr

```
                 65                  70                  75                  80
Glu Asp Phe Gly Met Tyr Phe Cys Gln Gln Thr Asn Ile Trp Pro Tyr
                            85                  90                  95

Thr Phe Gly Gly Gly Thr Lys Leu Glu Leu Lys
                100                 105
```

<210> SEQ ID NO 275
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 275

```
caggctgttg tgactcagga atctgcactc accacatcac ctggtgaaac agtcacactc      60
acttgtcgct caagtactgg ggctgttaca actagtaact atgccaactg ggtccaagaa     120
aaaccagcat ttattcactg gtctaatagg tggtaccaac aaccgagctc aggtgttcc      180 tgccagattc tcaggctccc tgattggaga caaggctgcc ctcaccatca gggggcaca      240 gactgaggat gagcatatat ttctgtgctc tacggtacag caaccattgg gtgttcggtg     300
gaggaaccaa actgactgtc ctag                                            324
```

<210> SEQ ID NO 276
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Arg Tyr Ser Asn
                85                  90                  95

His Trp Val Phe Gly Gly Gly Thr Lys Leu Thr Val Leu
                100                 105
```

<210> SEQ ID NO 277
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 277

```
gaggtgcagc tggtggagtc tgggggagac ttagtgaagc ctggagggtc cctgaaactc      60
tcctgtgcag cctctggatt cactttcagt agctatggca tgtcttggat cgccagact     120 ccagacaaga ggctggagtg ggtcgcaacc attagtagtg gtggtagtta cacctactat     180
```

```
ccagacagtg tgaaggggcg attcaccatc tccagagaca atgccaagaa caccctgtac    240
ctgcaaatga gcagtctgaa gtctgaagac acagccatgt attactgtgc aagacaaacg    300
gtaggatact ttgactactg gggccaaggc accactctca cagtctcctc a             351
```

<210> SEQ ID NO 278
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

```
Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Ile Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Gln Thr Val Gly Tyr Phe Asp Tyr Trp Gly Gln Gly Thr Thr
            100                 105                 110

Leu Thr Val Ser Ser
        115
```

<210> SEQ ID NO 279
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 279

```
caaattgttc tcacccagtc tccagcaatc atgtctccat ctctagggga acgggtcacc    60
atgacctgca ctgccagctc aagtgtaagt tccagttact tgcactggta ccagcagaag    120
tcaggatcct cccccaaact ctggatttat agcacatcca acctggcttc tggagtccca    180
gctcgcttca gtggcagggg gtctgggacc tcttactctc tcacaatcag cagcatggag    240
gctgaagatg ctgccactta ttactgccac cagtatcatc gttccccacc catcacgttc    300
ggtgctggga ccaagctgga gctgaaac                                       328
```

<210> SEQ ID NO 280
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

```
Gln Ile Val Leu Thr Gln Ser Pro Ala Ile Met Ser Pro Ser Leu Gly
1               5                   10                  15
```

-continued

```
Glu Arg Val Thr Met Thr Cys Thr Ala Ser Ser Val Ser Ser
         20                  25                  30

Tyr Leu His Trp Tyr Gln Gln Lys Ser Gly Ser Ser Pro Lys Leu Trp
         35                  40                  45

Ile Tyr Ser Thr Ser Asn Leu Ala Ser Gly Val Pro Ala Arg Phe Ser
 50                      55                  60

Gly Arg Gly Ser Gly Thr Ser Tyr Ser Leu Thr Ile Ser Ser Met Glu
 65                  70                  75                  80

Ala Glu Asp Ala Ala Thr Tyr Tyr Cys His Gln Tyr His Arg Ser Pro
                 85                  90                  95

Pro Ile Thr Phe Gly Ala Gly Thr Lys Leu Glu Leu Lys
             100                 105
```

<210> SEQ ID NO 281
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281

```
gagattcggc tccaacagtc tggaagtatg ctggcaaggc ctggggcttc agtgaagatg      60
tcctgcaagg cttctggcta cacctttacc aggtcctgga tgtactggat gaaacagagg     120
cctggacagg gtctggaatg gattggcgct atttatcctg gaaacagtga taacctac       180
aaccagaagt tcaagggcaa ggccaaactg actgcagtca cttccaccaa cactgcctac     240
atggagctca acagcctgac aaatgaggac tctgcggtct attattgtaa tactaactcg     300
ggggctatgg actcctgggg tcaaggagcc tcactcaccg tctcctca                 348
```

<210> SEQ ID NO 282
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

```
Glu Ile Arg Leu Gln Gln Ser Gly Ser Met Leu Ala Arg Pro Gly Ala
 1               5                  10                  15

Ser Val Lys Met Ser Cys Lys Ala Ser Gly Tyr Thr Phe Thr Arg Ser
                 20                  25                  30

Trp Met Tyr Trp Met Lys Gln Arg Pro Gly Gln Gly Leu Glu Trp Ile
             35                  40                  45

Gly Ala Ile Tyr Pro Gly Asn Ser Asp Thr Thr Tyr Asn Gln Lys Phe
 50                  55                  60

Lys Gly Lys Ala Lys Leu Thr Ala Val Thr Ser Thr Asn Thr Ala Tyr
 65                  70                  75                  80

Met Glu Leu Asn Ser Leu Thr Asn Glu Asp Ser Ala Val Tyr Tyr Cys
                 85                  90                  95

Asn Thr Asn Ser Gly Ala Met Asp Ser Trp Gly Gln Gly Ala Ser Leu
             100                 105                 110

Thr Val Ser Ser
             115
```

<210> SEQ ID NO 283
<211> LENGTH: 337

<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 283
gatgttgtga tgacccagag tccactcact ttgtcggtta ccattggaca gccagcctcc    60
ttctcttgca agtcaaggca gagcctctta gatagtgatg aaagacata tttgaattgg    120 ttgttgcaga ggccaggcca gtctccaaag cgcctaatct atctggtgtc taaactggac    180
tctggagtcc ctgacaggtt cactggcagt ggatcaggga cagatttcac actgacaatc    240
agcagagtgg aggctgagga tttgggagtt tattattgct ggcaaggtac acattttccg    300
tggacgttcg gtggaggcac caagctggaa atcaaac                             337

<210> SEQ ID NO 284
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 284

Asp Val Val Met Thr Gln Ser Pro Leu Thr Leu Ser Val Thr Ile Gly
1               5                  10                  15

Gln Pro Ala Ser Phe Ser Cys Lys Ser Arg Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Thr Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

<210> SEQ ID NO 285
<211> LENGTH: 357
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 285
gaggtgcagc tggtggagtc tgggggagac ttagtgaagc ctggagggtc cctgaaactc    60
tcctgtgcag cctctggatt cactttcagt agctatggca tgtcttgggt tcgccagact    120
ccagacaaga ggctggagtg ggtcgcaacc attagcagtg gtggtagtta tatctttat    180 ccagacagtg tgaaggggcg attcaccatc tccagagaca atgccaagaa caccctgtac    240
ctgcaaatga gcagtctgag gtctgaggac acagccatgt attactgtgc aaaactatgat    300 ggttacttcg tcggatttac ttactggggc caagggactc tggtcactgt ctctgca       357

<210> SEQ ID NO 286
<211> LENGTH: 119
<212> TYPE: PRT

<213> ORGANISM: Artificial Sequence
<220> FEATURE:
<223> OTHER INFORMATION: Description of Artificial Sequence: Synthetic
    polypeptide

<400> SEQUENCE: 286

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Ile Phe Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Asn Tyr Asp Gly Tyr Phe Val Gly Phe Thr Tyr Trp Gly Gln Gly
            100                 105                 110

Thr Leu Val Thr Val Ser Ala
        115

<210> SEQ ID NO 287
<211> LENGTH: 322
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 287
gacatccaga tgactcagtc tccagcctcc ctatctgcat ctgtgggaga aactgtcacc      60
atcacatgtc gagcaagtga gaatatttac agttatttag catggtatca gcagaaacag     120
ggaaaatctc ctcagctcct ggtcagaaat gcaaaaacct tagcagaagg tgtgtcatca     180
agattcagtg gcagtggatc aggcacacag ttttctctga agatcaacag cctgcagcct     240
gaagattttg ggagttatta ctgtcaacat cattatggta ctccgtggac gttcggtgga     300
ggcaccaagc tggaaatcaa ac                                              322

<210> SEQ ID NO 288
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 288

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Arg Asn Ala Lys Thr Leu Ala Glu Gly Val Ser Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Trp
                85                  90                  95

Thr Phe Gly Gly Gly Thr Lys Leu Glu Ile Lys
            100                 105

<210> SEQ ID NO 289
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 289
caggctgttg tgactcagga atctgcactc accacatcac ctggtgaaac agtcacactc    60
acttgtcgct caagtactgg ggctgttaca actagtaact atgccaactg gtccaagaa   120 aaaccagcat ttattcactg gtctaatagg tggtaccaac aaccgagctc aggtgttcc   180 tgccagattc tcaggctccc tgattggaga caaggctgcc ctcaccatca caggggcaca   240
gactgaggat gagcatatat ttctgtgttc tacggtacag caaccattgg gtgttcggtg   300
gaggaaccaa actgactgtc ctag                                          324

<210> SEQ ID NO 290
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Arg Tyr Ser Asn
                85                  90                  95

His Trp Val Phe Gly Gly Gly Thr Lys Leu Thr Val Leu
            100                 105

<210> SEQ ID NO 291
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 291
caggtccaac tgcgacaacc tggggctgag cttgtgatgc tggggcttc agtgaagatg    60 tcgtgcaaga cttctggcta cacattcagt gactactgga cattgggt gaaacagagg    120 cctggacaag gccttgaatg gatcggaaca attgatactt ctgatagtta tactacctac   180

```
aatcaaaagt tcaaggacaa ggccacgttg actgtcgacg aatcttccaa tacagccttc    240
atgcatctca gcagcctgac atctgaggac tctgcggtct attattgtgc aacattactt    300
cggctacgtt actactttga atattggggc cagggcacca ctctcacagt ctcctca      357

<210> SEQ ID NO 292
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Gln Val Gln Leu Arg Gln Pro Gly Ala Glu Leu Val Met Pro Gly Ala
1               5                   10                  15

Ser Val Lys Met Ser Cys Lys Thr Ser Gly Tyr Thr Phe Ser Asp Tyr
            20                  25                  30

Trp Ile His Trp Val Lys Gln Arg Pro Gly Gln Gly Leu Glu Trp Ile
        35                  40                  45

Gly Thr Ile Asp Thr Ser Asp Ser Tyr Thr Thr Tyr Asn Gln Lys Phe
    50                  55                  60

Lys Asp Lys Ala Thr Leu Thr Val Asp Glu Ser Ser Asn Thr Ala Phe
65                  70                  75                  80

Met His Leu Ser Ser Leu Thr Ser Glu Asp Ser Ala Val Tyr Tyr Cys
                85                  90                  95

Ala Thr Leu Leu Arg Leu Arg Tyr Tyr Phe Glu Tyr Trp Gly Gln Gly
            100                 105                 110

Thr Thr Leu Thr Val Ser Ser
        115

<210> SEQ ID NO 293
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 293
gaggtccaac tgcaacagtc tggacctgag ttggtgaagc ctggggcttc agtgaagata    60
tcctgcaagg cttctggtta ctcattcact gactactaca tacactgggt gaaacaaagc    120
catgtaaaga gccttgaatg gattggacgt attaatccta acaatggtga ttctgcctac    180
aaccagaatt tcaaggacaa ggccagtttg actgtaaatg agtcctccac cacagcctat    240
atggaactcc acagcctgac atctgaggac tctgcagtct attactgtgc aagacgccaa    300
attcactact atggtatgga cttctggggt caaggaacct cagtcaccgt ctcctca      357

<210> SEQ ID NO 294
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
```

```
                  20                  25                  30
Tyr Ile His Trp Val Lys Gln Ser His Val Lys Ser Leu Glu Trp Ile
            35                  40                  45
Gly Arg Ile Asn Pro Asn Asn Gly Asp Ser Ala Tyr Asn Gln Asn Phe
        50                  55                  60
Lys Asp Lys Ala Ser Leu Thr Val Asn Glu Ser Ser Thr Thr Ala Tyr
65                  70                  75                  80
Met Glu Leu His Ser Leu Thr Ser Glu Asp Ser Ala Val Tyr Tyr Cys
                85                  90                  95
Ala Arg Arg Gln Ile His Tyr Tyr Gly Met Asp Phe Trp Gly Gln Gly
            100                 105                 110
Thr Ser Val Thr Val Ser Ser
        115

<210> SEQ ID NO 295
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 295
tctgatgtgc agcttcagga gtcgggacct ggcctggtga aaccttctca gtctctgtcc      60
ctcacctgca ctgtcactgg ctactcaatc accagtgatt atacctggaa ctggatccgg     120
cagtttccag gaaacaaact ggagtggatg ggctacataa gctacagtgg cagcaccagc     180
tacaacccat ctctcaaaag tcgaatctct atcactcgag acacatccaa gaaccagttc     240
ttcgtgcagt tgaattctgt gactactgag gacacagcca catattactg tgcaaggggg     300
agtggttata gtctctatac tatggactac tggggtcaag aacctcagtc accgtctcc     360 tca                                                                    363

<210> SEQ ID NO 296
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Ser Asp Val Gln Leu Gln Glu Ser Gly Pro Gly Leu Val Lys Pro Ser
1               5                   10                  15
Gln Ser Leu Ser Leu Thr Cys Thr Val Thr Gly Tyr Ser Ile Thr Ser
            20                  25                  30
Asp Tyr Thr Trp Asn Trp Ile Arg Gln Phe Pro Gly Asn Lys Leu Glu
        35                  40                  45
Trp Met Gly Tyr Ile Ser Tyr Ser Gly Ser Thr Ser Tyr Asn Pro Ser
    50                  55                  60
Leu Lys Ser Arg Ile Ser Ile Thr Arg Asp Thr Ser Lys Asn Gln Phe
65                  70                  75                  80
Phe Val Gln Leu Asn Ser Val Thr Thr Glu Asp Thr Ala Thr Tyr Tyr
                85                  90                  95
Cys Ala Arg Gly Ser Gly Tyr Ser Leu Tyr Thr Met Asp Tyr Trp Gly
            100                 105                 110
Gln Gly Thr Ser Val Thr Val Ser Ser
        115                 120
```

<210> SEQ ID NO 297
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 297
caggctgttg tgactcagga atctgcactc accacatcac ctggtgaaac agtcacactc      60
acttgtcgct caagtactgg ggctgttaca actagtaact atgccaactg ggtccaagaa     120
aaaccagcat ttattcactg gtctagtggg tgataccaac aaccgagctc caggtgttcc     180
tgccagattc tcaggctccc tgattggaga caaggctgcc ctcaccatca cagggcaca      240 gactgaggac gagcatatat ttctgtgctc tatggtacaa caaccatagc tgggtgttcg     300
gtggaggaac aagctggaa atcaatc                                          327

<210> SEQ ID NO 298
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Val Gly Asp Thr Asn Asn Arg Ala Pro Val Pro Ala Arg Phe
        50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Asn Asn
                85                  90                  95

His Ser Trp Val Phe Gly Gly Gly Thr Lys Leu Glu Ile Asn
            100                 105                 110

<210> SEQ ID NO 299
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Thr Tyr Ala Met His
1               5

<210> SEQ ID NO 300
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 300

Tyr Ile Asn Pro Ser Ser Gly Tyr Ile Glu Tyr Asn Gln Lys Phe Lys
1               5                   10                  15
Asp

<210> SEQ ID NO 301
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

His Trp Gly Ala Tyr
1               5

<210> SEQ ID NO 302
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Gly Tyr Thr Phe Thr Thr Tyr
1               5

<210> SEQ ID NO 303
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Asn Pro Ser Ser Gly Tyr
1               5

<210> SEQ ID NO 304
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

His Trp Gly Ala Tyr
1               5

<210> SEQ ID NO 305
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Gly Tyr Thr Phe Thr Thr Tyr Ala
1               5

<210> SEQ ID NO 306
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Ile Asn Pro Ser Ser Gly Tyr Ile
1               5

<210> SEQ ID NO 307
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Ala Arg His Trp Gly Ala Tyr
1               5

<210> SEQ ID NO 308
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Gly Gly Gly Gly Ser Gly Gly Gly Ser Gly Gly Gly Gly Ser
1               5                   10                  15

<210> SEQ ID NO 309
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 309

His His His His His His
1               5
```

ANTIBODIES TO GALECTIN-3 AND METHODS OF USE THEREOF

CROSS-REFERENCE TO RELATED APPLICATIONS

This application is a National Stage Application of PCT/US2019/016430, filed Feb. 1, 2019, which claims priority to U.S. Provisional Patent Application No. 62/625,166, filed Feb. 1, 2018, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Mar. 11, 2019, is named 115872-0526_SL.txt and is 122,075 bytes in size.

BACKGROUND OF THE INVENTION

Galectins are a family of small, highly conserved eukaryotic proteins which recognize specific complex sugars on glycosylated cell surface proteins. They are essential for linking cancer cells with the stromal microenvironment to modulate development, adhesion, signaling, invasions and immune system interactions. Galectins can be found in the nucleus, the cytoplasm and the pericellular space. Extracellular galectins are primarily released in exosomes and do not appear to have classic secretion from the ER or Golgi. Humans have at least 12 different galectins which are variably expressed in various tissues and stages on development. In the last decade, it has become apparent that human Galectins, particularly Galectin-3 (LGALS3), represent an important link between the microenvironment and the tumor cell. In particular, biologic functions of glycoproteins and other surface glycans are primarily dependent on the specific sugar chains attached in the Golgi leading to unique Galectin selectivity. Outside the cell, LGALS3 participates in regulation of cell membrane residence time, adhesion, migration, invasion and angiogenesis functions. Although LGALS3 binds to other natural ligands, its highest affinity ligand is the most proximal lactosamine disaccharide in poly-lactosamine chains that decorate many O- and N-Glycan species. Through binding and polymerization, LGALS3 forms a lattice and regulates the position and residence time of growth factor receptors including EGFR, PDGFR, Integrins and CTLA4, among many others. (FIG. 1). Activation of downstream signaling molecules, such as SRC, ERK, AKT, and FAK drives the production of key molecules involved in metastasis and invasion. On the surface of T-cells, CTLA4 surface concentrations are stabilized by LGALS3, leading to immunosuppression. Loss of the LGALS3 lattice inhibits multiple cancer cell and immune cell behaviors. In addition to cancer, LGALS3 excess has also been linked to renal disease, hepatic fibrosis, pulmonary fibrosis, cardiac failure and parasitic diseases (see FIG. 3).

SUMMARY OF THE INVENTION

Provided herein are compositions, methods, and uses involving antibodies that immunospecifically bind to Galectin-3 (LGALS3), and modulate expression and/or activity of LGALS3 for managing or treating LGALS-mediated disorders, such as cancer.

In certain embodiments, provided herein are antibodies or an antigen-binding fragments thereof, wherein the antibody or antigen-binding fragment thereof immunospecifically binds to a Galectin-3 (LGALS3) carbohydrate binding domain (CBD). In some embodiments, the LGALS3 CBD comprises SEQ ID NO: 27. In some embodiments, the antibody is a monoclonal antibody, a single chain antibody, or any composition comprising an antigen-binding fragment thereof.

In some embodiments, the antibody or antigen-binding fragment thereof inhibits in vitro invasion of tumor cells in a Matrigel invasion assay. In some embodiments, the tumor cells are ovarian tumor cells. In some embodiments, the antibody or antigen-binding fragment thereof inhibits binding of LGALS3 to a glycosylated cell surface protein. In some embodiments, the antibody or antigen-binding fragment thereof inhibits binding of LGALS3 to a glycosylated cell surface receptor. In some embodiments, the antibody or antigen-binding fragment thereof inhibits binding of LGALS3 to a glycosylated growth factor receptor. In some embodiments, the antibody or antigen-binding fragment thereof inhibits binding of LGALS3 to glycosylated mucin-1 (MUC1), mucin-4 (MUC4), mucin-16 (MUC16), a disialoganglioside, GD2, epidermal growth factor receptor (EGFR), platelet-derived growth factor receptor (PDGFR), insulin-like growth factor receptor (IGFR), cMET/hepatocyte growth factor receptor (HGFR), an integrin and CTLA4. In some embodiments, the glycosylated MUC16 is N-glycosylated at Asn1800 or Asn1806. In some embodiments, the antibody or antigen-binding fragment thereof inhibits growth of a tumor that expresses a glycosylated form of MUC16.

In some embodiments, the antibody or antigen-binding fragment thereof comprises a heavy chain variable region (VH), comprising (a) a VH complementarity determining region (CDR)1 comprising the amino acid sequence SYGVH (SEQ ID NO: 5); (b) a VH CDR2 comprising the amino acid sequence VIWSDGSTTYNSTLKS (SEQ ID NO: 6); and (c) a VH CDR3 comprising the amino acid sequence HISNYGTMDY (SEQ ID NO: 7). In some embodiments, the antibody or antigen-binding fragment thereof comprises a VH, comprising (a) a VH complementarity determining region (CDR)1 comprising the amino acid sequence GFSLSSY (SEQ ID NO: 11); (b) a VH CDR2 comprising the amino acid sequence WSDGS (SEQ ID NO: 12); and (c) a VH CDR3 comprising the amino acid sequence HISNYGTMDY (SEQ ID NO: 13). In some embodiments, the antibody or antigen-binding fragment thereof comprises a VH, comprising: (a) a VH complementarity determining region (CDR)1 comprising the amino acid sequence GFSLSSYG (SEQ ID NO: 17); (b) a VH CDR2 comprising the amino acid sequence IWSDGST (SEQ ID NO: 18); and (c) a VH CDR3 comprising the amino acid sequence ARHISNYGTMDY (SEQ ID NO: 19). In some embodiments, the antibody or antigen-binding fragment thereof comprises a VH comprising the amino acid sequence of QVQLKESGPGLVAPSQSLSITCTIS-GFSLSSYGVHWVRQPPGKGLEWLVVIWSDGSTTYN STLKSRLSISKDNSKSQVFLKMNSLQTDDTAMYY-CARHISNYGTMDYWGQGTSVTVS (SEQ ID NO: 24).

In some embodiments, the antibody or antigen-binding fragment thereof comprises a light chain variable region (VL), comprising (a) a VL CDR1 comprising the amino acid sequence RASQDIRNYLN (SEQ ID NO: 8); (b) a VL CDR2 comprising the amino acid sequence YTSRLHS (SEQ ID NO: 9); and (c) a VL CDR3 comprising the amino acid sequence QHFNTLPPT (SEQ ID NO: 10). In some embodiments, the antibody or antigen-binding fragment thereof comprises a VL, comprising: (a) a VL CDR1 comprising the amino acid sequence RASQDIRNYLN (SEQ ID NO: 14); (b) a VL CDR2 comprising the amino acid sequence YTSRLHS (SEQ ID NO: 15); and (c) a VL CDR3 comprising the amino acid sequence QHFNTLPPT (SEQ ID NO: 16). In some embodiments, the antibody or antigen-binding fragment thereof comprises a VL, comprising: (a) a VL CDR1 comprising the amino acid sequence QDIRNY (SEQ ID NO: 20); (b) a VL CDR2 comprising the amino acid sequence YTS (SEQ ID NO: 21); and (c) a VL CDR3 comprising the amino acid sequence QHFNTLPPT (SEQ ID NO: 22). In some embodiments, the antibody or antigen-binding fragment thereof comprises a VL comprising the amino acid sequence of DIQMTQTTSSL-SASLGDRVTISCRASQDIR-NYLNWYQQKPDGSIKLLIYYTSRLHSGVPSR FSGSGSGTDYSLTIRNLEQEDI-ATYFCQHFNTLPPTFGGGTKLEIK (SEQ ID NO: 26).

In some embodiments, the antibody or antigen-binding fragment thereof comprises a VH comprising the amino acid sequence of SEQ ID NO: 24 and a VL comprising the amino acid sequence of SEQ ID NO: 26.

In some embodiments, the antibody or antigen-binding fragment thereof comprises a heavy chain variable region (VH), comprising a VH CDR1, VH CDR2, and VH CDR3 of an antibody provided in any one of FIG. 13A, 13B, or 13C. In some embodiments, the antibody or antigen-binding fragment thereof comprises a light chain variable region (VL), comprising a VL CDR1, VL CDR2, and VL CDR3 of an antibody provided in any one of FIG. 13A, 13B, or 13C. In some embodiments, the antibody or antigen-binding fragment thereof comprises a heavy chain variable region (VH), comprising a VH CDR1, VH CDR2, and VH CDR3 and a light chain variable region (VL), comprising a VL CDR1, VL CDR2, and VL CDR3 of an antibody provided in any one of FIG. 13A, 13B, or 13C.

In some embodiments, the antibody or antigen-binding fragment thereof comprises a heavy chain and/or a light chain of an antibody provided in any one of FIG. 12A, 12B, 13D, 13E, 13F, 13G, 13H, 13I, 13J, 13K, 13L, 13M, 13N, or 13O.

In some embodiments, the antibody comprises human-derived heavy and light chain constant regions. In some embodiments, the heavy chain constant region has an isotype selected from the group consisting of gamma 1, gamma 2, gamma 3, and gamma 4. In some embodiments, the light chain constant region has an isotype selected from the group consisting of kappa and lambda. In some embodiments, the antibody or antigen-binding fragment thereof is humanized. In some embodiments, the antibody or antigen-binding fragment thereof is a humanized form of a rodent antibody. In some embodiments, the antibody is an immunoglobulin comprising two identical heavy chains and two identical light chains. In some embodiments, the immunoglobulin is an IgG.

Also provided herein, in certain embodiments, are antibody conjugates comprising an antibody or antigen-binding fragment thereof provided herein conjugated to an agent. In some embodiments, the agent is an imaging agent or a cytotoxic agent.

In some embodiments, the antibody or antigen-binding fragment thereof is a bispecific antibody. In some embodiments, the bispecific antibody immunospecifically binds CD3. In some embodiments, the bispecific antibody comprises an immunoglobulin that immunospecifically binds LGALS3, wherein the light chain of the immunoglobulin is conjugated via a peptide linker to a single chain variable fragment (scFv) that immunospecifically binds to CD3.

Also provided herein, in certain embodiments, are bispecific antibody conjugates comprising a bispecific antibody provided herein conjugated to an agent. In some embodiments, the agent is an imaging agent or a cytotoxic agent.

In some embodiments, the antigen-binding fragment thereof is a scFv. Also provided herein, in certain embodiments, are scFv conjugates comprising an scFv provided herein conjugated to an agent. In some embodiments, the agent is an imaging agent or a cytotoxic agent.

Also provided herein, in certain embodiments, are chimeric antigen receptors (CAR) comprising: the antibody or antigen-binding fragment provided herein or an scFv provided herein.

Also provided herein, in certain embodiments, are T-cells that recombinantly expresses a CAR provided herein.

Also provided herein, in certain embodiments, are polynucleotides comprising nucleic acid sequences encoding an antibody heavy chain provided herein, an antibody light chain provided herein, an scFv provided herein, and/or a CAR provided herein.

Also provided herein, in certain embodiments, are vectors comprising a polynucleotide provided herein operably linked to a promoter.

Also provided herein, in certain embodiments, are isolated cells comprising a polynucleotide provided herein or a vector provided herein.

Also provided herein, in certain embodiments, are pharmaceutical compositions comprising: a therapeutically effective amount of the antibody or antigen-binding fragment thereof provided herein, an antibody conjugate provided herein, a bispecific antibody provided herein, a bispecific antibody conjugate provided herein, an scFv provided herein, an scFv conjugate provided herein, a CAR provided herein, a polynucleotide provided herein, a vector provided herein, or a cell of provided herein; and a pharmaceutically acceptable carrier.

Also provided herein, in certain embodiments, are methods of treating cancer in a patient in need thereof, comprising administering to said patient a pharmaceutical composition provided herein. In some embodiments, said cancer is a cancer of the ovary, lung, pancreas, breast, uterine, fallopian tube, or primary peritoneum. In some embodiments, said cancer is a metastatic cancer. In some embodiments, the pharmaceutical composition inhibits metastasis in the patient. In some embodiments, the said patient is a human patient. In some embodiments, the method further comprises administering a therapeutically effective amount of an additional therapeutic agent to the patient.

Also provided herein, in certain embodiments, is an immunogenic peptide of SEQ ID NO: 2. In some embodiments, the immunogenic peptide is conjugated to an immunogenic carrier protein.

Also provided herein, in certain embodiments, are fusion protein comprising: (a) a LGALS3 protein or fragment thereof comprising a LGALS3 carbohydrate binding domain; and (b) an Fc domain. In some embodiments, the LGALS3 carbohydrate binding domain comprises domains SEQ ID NO:32. In some embodiments, the LGALS3 carbohydrate binding domain comprises amino acids 117-244 of SEQ ID NO:1. In some embodiments, the Fc domain is a human IgG1 Fc domain.

Also provided herein, in certain embodiments, are methods for generating an antibody or an antigen-binding fragment thereof that specifically binds to a LGAL3 CBD, comprising immunizing a subject with the immunogenic peptide provided herein or a fusion protein provided herein. In some embodiments, the subject is a goat, a sheep, a donkey, a chicken, a guinea pig, a rat, a rabbit, or a mouse. In some embodiments, the immunogenic peptide is conjugated to an immunogenic carrier protein. In some embodiments, the immunogenic carrier protein is keyhole limpet hemocyanin.

BRIEF DESCRIPTION OF THE DRAWINGS

FIG. 1A illustrates the structure and activity of extracellular Galectin-3 (LGALS3) which forms a pentamer to link cell surface cancer molecules, such as MUC16 in ovarian cancer, to signaling molecules via contact with signaling receptor, such as EGFR and Integrins. Activation of downstream signaling molecules, such as SRC, ERK, AKT, and FAK in turn drives the production of key molecules for metastasis and invasion. FIG. 1B illustrates how antibody inhibitors that bind to the LGALS3 carbohydrate binding domain will block activation of "outside-in" signal transduction by disrupting the LGALS3 surface complexes and destabilizing the cell surface receptors.

FIG. 3 illustrates in vitro and in vivo experimental functions of Galectin 3 and potential blocking antibody effects for treatment with the antibodies provided.

FIG. 4 illustrates the primary structure of the LGALS3 carbohydrate binding domain (CBD). The LGALS3 CBD is divided into 5 sub-domains, each binding to a single sugar residue and, conventionally labeled as A B C D and E. In the figure, the highly conserved amino acids are underlined while domains C, D and E are shown in the boxed area. This sequence was used for the murine peptide immunization. R186(*) in particular is important to the functions of LGALS3. The LGALS3 CBD sequence is highly homologous to the murine Galectin-3 but differs from GAL1, GAL7 and GAL9. While each of these family members have similar sugar binding domains, LGALS3 is the only lectin with the polymerization domain.

FIG. 5 illustrates ELISA reactivity for various Galectin family members and sequences. Abbreviations: CBD-3=Carbohydrate binding domain of Galectin-3 (human); LGALS3=human Galectin-3 whole protein; GAL1 CBD=Galectin-1 Carbohydrate Binding Domain (human). The antibodies selected were positive both whole protein (LGALS3) and the LGALS3 carbohydrate binding domain (CBD-3). Several Group D antibodies were cloned to determine the value of co-inhibition of both Galectin 1 and LGALS3 and the related in vivo toxicity profiles.

FIG. 12A illustrates 14D11.2D2 antibody Heavy Chain DNA and Amino Acid sequences and CDR sequences identified by Kabat, Chothia and IMGT numbering. The shaded region represents the highly conserved region of the heavy chain. FIG. 12B illustrates 14D11.2D2 antibody Lights Chain DNA and Amino Acid sequences and CDR sequences identified by Kabat, Chothia and IMGT numbering. The shaded region represents the highly conserved region of the light chain.

FIG. 13A-C illustrates CDR sequences of isolated LGALS3 antibodies obtained by peptide immunization as identified by Kabat (13A), Chothia (13B) and IMGT (13C) numbering.

FIG. 13D-O illustrates VH and/or VL chain sequences of the same LGALS3 antibodies. Light chain sequences for 3G10.D11, 11D1.A12, and 21A12.A6 were not obtained.

FIG. 15 illustrates exemplary nucleotide (NM_002306.3) and amino acid (NP_002297.2) sequences for human LGALS3.

DETAILED DESCRIPTION OF THE INVENTION

Figure 2A:
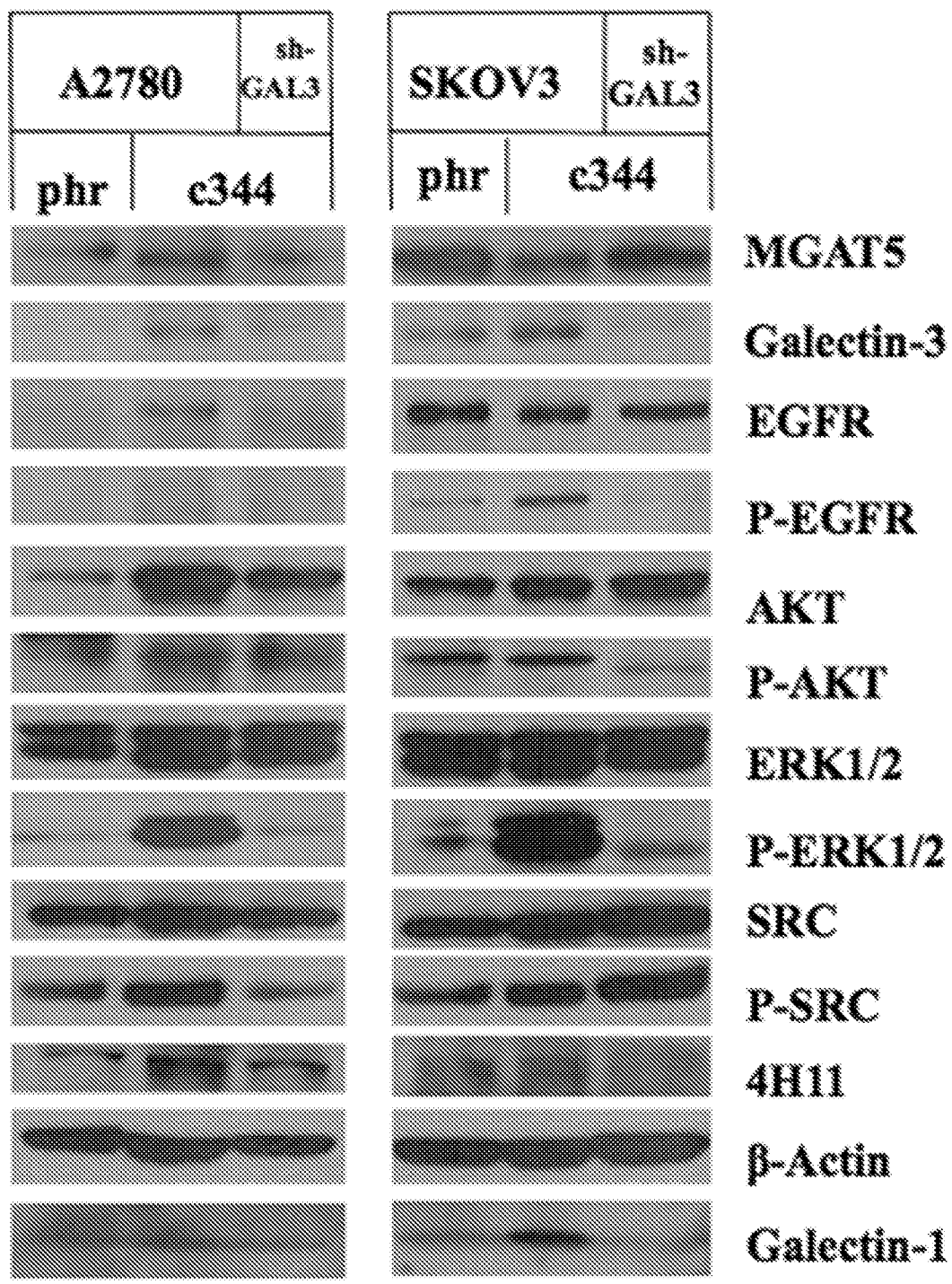
FIG. 2A illustrates LGALS3 shRNA blocking MUC16 oncogene activation, as assessed by inhibition of phosphorylation of EGFR, AKT, ERK and SRC (P-EGFR, P-AKT, P-ERK, P-SRC, respectively). Loss of LGALS3 greatly inhibits MUC16 activation (MUC16c344) of a variety of oncogenes in two ovarian models.

The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Definitions

Unless defined otherwise, all technical and scientific terms used herein have the meaning commonly understood by a person skilled in the art to which this disclosure belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise. The terminology used herein is for the purpose of describing particular embodiments only and is not intended to be limiting of the disclosure.

As used herein, the singular forms "a", "an" and "the" are intended to include the plural forms as well, unless the context clearly indicates otherwise. 00471 As used herein, the terms "about" when used to modify a numeric value or numeric range, indicate that deviations of 5% to 10% above and 5% to 10% below the value or range remain within the intended meaning of the recited value or range.

As used herein, the term "administration" of an agent to a subject includes any route of introducing or delivering the agent to a subject to perform its intended function. Administration can be carried out by any suitable route, including. but not limited to, intravenously, intramuscularly, intraperitoneally, subcutaneously, and other suitable routes as described herein. Administration includes self-administration and the administration by another.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refer to agents that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. In some embodiments, amino acids forming a polypeptide are in the D form. In some embodiments, the amino acids forming a polypeptide are in the L form. In some embodiments, a first plurality of amino acids forming a polypeptide are in the D form and a second plurality are in the L form.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter code.

The terms "polypeptide," "peptide," and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a composition known to exhibit the desired therapeutic effect) and a negative control (a subject or a sample that does not receive the therapy or receives a placebo) are typically employed.

As used herein, the term "effective amount" or "therapeutically effective amount" refers to a quantity of an agent sufficient to achieve a desired therapeutic effect. In the context of therapeutic applications, the amount of a therapeutic peptide administered to the subject can depend on the type and severity of the infection and on the characteristics of the individual, such as general health, age, sex, body weight and tolerance to drugs. It can also depend on the degree, severity and type of disease. The skilled artisan will be able to determine appropriate dosages depending on these and other factors.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression can include splicing of the mRNA in a eukaryotic cell. The expression level of a gene can be determined by measuring the amount of mRNA or protein in a cell or tissue sample. In one aspect, the expression level of a gene from one sample can be directly compared to the expression level of that gene from a control or reference sample. In another aspect, the expression level of a gene from one sample can be directly compared to the expression level of that gene from the same sample following administration of the compositions disclosed herein. The term "expression" also refers to one or more of the following events: (1) production of an RNA template from a DNA sequence (e.g., by transcription) within a cell; (2) processing of an RNA transcript (e.g., by splicing, editing, 5' cap formation, and/or 3' end formation) within a cell; (3) translation of an RNA sequence into a polypeptide or protein within a cell; (4) post-translational modification of a polypeptide or protein within a cell; (5) presentation of a polypeptide or protein on the cell surface; and (6) secretion or presentation or release of a polypeptide or protein from a cell.

The term "linker" refers to synthetic sequences (e.g., amino acid sequences) that connect or link two sequences, e.g., that link two polypeptide domains. In some embodiments, the linker contains 1, 2, 3, 4, 5, 6, 7, 8, 9, or 10 of amino acid sequences.

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments $F(ab')_2$, and Fab. $F(ab')_2$, and Fab fragments that lack the Fc fragment of intact antibody, clear more rapidly from the circulation, and may have less non-specific tissue binding of an intact antibody (Wahl et al., J. Nucl. Med. 24:316-325 (1983)). The antibodies of the invention comprise whole native antibodies, monoclonal antibodies, human antibodies, humanized antibodies, camelised antibodies, multispecific antibodies, bispecific antibodies, chimeric antibodies, Fab, Fab', single chain V region fragments (scFv), single domain antibodies (e.g., nanobodies and single domain camelid antibodies), VNAR fragments, Bi-specific T-cell engager (BiTE) antibodies, minibodies, disulfide-linked Fvs (dsFv), and anti-idiotypic (anti-Id) antibodies, intrabodies, fusion polypeptides, unconventional antibodies and antigen-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

In certain embodiments, an antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant ($C_H$) region. The heavy chain constant region is comprised of three domains, CH1, CH2 and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1 q) of the classical complement system. As used herein interchangeably, the terms "antigen-binding portion", "antigen-binding fragment", or "antigen-binding region" of an antibody, refer to the region or portion of an antibody that binds to the antigen and which confers antigen specificity to the antibody; fragments of antigen-binding proteins, for example, antibodies include one or more fragments of an antibody that retain the ability to specifically bind to an antigen (e.g., a peptide/HLA complex). It has been shown that the antigen-binding function of an antibody can be performed by fragments of a full-length antibody. Examples of antigen-binding portions encompassed within the term "antibody fragments" of an antibody include a Fab fragment, a monovalent fragment consisting of the $V_L$, $V_H$, $C_L$ and CHI domains; a $F(ab)_2$ fragment, a bivalent fragment comprising two Fab fragments linked by a disulfide bridge at the hinge region; a Fd fragment consisting of the $V_H$ and CHI domains; a Fv fragment consisting of the $V_L$ and $V_H$ domains of a single arm of an antibody; a dAb fragment (Ward et al., Nature 341: 544-546 (1989)), which consists of a $V_H$ domain; and an isolated complementarity determining region (CDR).

Antibodies and antibody fragments can be wholly or partially derived from mammals (e.g., humans, non-human primates, goats, guinea pigs, hamsters, horses, mice, rats, rabbits and sheep) or non-mammalian antibody producing animals (e.g., chickens, ducks, geese, snakes, urodele amphibians). The antibodies and antibody fragments can be produced in animals or produced outside of animals, such as from yeast or phage (e.g., as a single antibody or antibody fragment or as part of an antibody library).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules. These are known as single chain Fv (scFv); see e.g., Bird et al., Science 242:423-426 (1988); and Huston et al., Proc. Natl. Acad. Sci. 85: 5879-5883 (1988). These antibody fragments are obtained using conventional techniques known to those of ordinary skill in the art, and the fragments are screened for utility in the same manner as are intact antibodies.

An "isolated antibody" or "isolated antigen-binding protein" is one which has been identified and separated and/or recovered from a component of its natural environment. "Synthetic antibodies" or "recombinant antibodies" are generally generated using recombinant technology or using peptide synthetic techniques known to those of skill in the art.

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H$:$V_L$ heterodimer. The heavy ($V_H$) and light chains ($V_L$) are either joined directly or joined by a peptide-encoding linker (e.g., about 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain.

Despite removal of the constant regions and the introduction of a linker, scFv proteins retain the specificity of the original immunoglobulin. Single chain Fv polypeptide antibodies can be expressed from a nucleic acid comprising $V_H$- and $V_L$-encoding sequences as described by Huston, et al. (Proc. Nat. Acad. Sci. USA, 85:5879-5883 (1988)). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hybridoma (Larchmt) 27(6):455-51 (2008); Peter et al., J Cachexia Sarcopenia Muscle (2012); Shieh et al., J Imunol 183(4): 2277-85 (2009); Giomarelli et al., Thromb Haemost 97(6): 955-63 (2007); Fife eta., J Clin Invst 116(8):2252-61 (2006); Brocks et al., Immunotechnology 3(3): 173-84 (1997); Moosmayer et al., Ther Immunol 2(10):31-40 (1995) Agonistic scFvs having stimulatory activity have been described (see, e.g., Peter et al., J Biol Chem 25278(38):36740-7 (2003); Xie et al., Nat Biotech 15(8):768-71 (1997); Ledbetter et al., Crit Rev Immunol 17(5-6):427-55 (1997); Ho et al., Bio Chim Biophys Acta 1638(3):257-66 (2003)).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

As used herein, "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat system (Kabat, E. A., et al. Sequences of Proteins of Immunological Interest, Fifth Edition, U.S. Department of Health and Human Services, NIH Publication No. 91-3242(1991)).

As used herein, the term "constant region" or "constant domain" is interchangeable and has its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, an "epitope" is a term in the art and can refer to a localized region of an antigen to which an antibody can immunospecifically bind. An epitope can be, e.g., contiguous amino acids of a polypeptide (linear or contiguous epitope) or an epitope can, e.g., come together from two or more noncontiguous regions of a polypeptide or polypeptides (conformational, non-linear, discontinuous, or non-contiguous epitope).

As used herein, the term "ligand" refers to a molecule that binds to a receptor. In particular, the ligand binds a receptor on another cell, allowing for cell-to-cell recognition and/or interaction.

As used herein, the term "affinity" is meant a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes (e.g., either monovalent or multivalent). Methods for calculating the affinity of an antibody for an antigen are known in the art, comprising use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay). Nucleic acid molecules useful in the presently disclosed subject matter include any nucleic acid molecule that encodes a polypeptide or a fragment thereof. In certain embodiments, nucleic acid molecules useful in the presently disclosed subject matter include nucleic acid molecules that encode an antibody or an antigen-binding portion thereof. Such nucleic acid molecules need not be 100% identical with an endogenous nucleic acid sequence, but will typically exhibit substantial identity. Polynucleotides having "substantial homology" or "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger, Methods Enzymol. 152:399 (1987); Kimmel, A. R. Methods Enzymol. 152:507 (1987)).

As used herein, the terms "immunospecifically binds," "immunospecifically recognizes," "specifically binds," and "specifically recognizes" are analogous terms in the context of antibodies and refer to antibodies and antigen-binding fragments thereof that bind to an antigen (e.g., epitope or immune complex) via the antigen-binding sites as understood by one skilled in the art, and does not exclude cross-reactivity of the antibody or antigen-binding fragment with other antigens.

The terms "substantially homologous" or "substantially identical" mean a polypeptide or nucleic acid molecule that exhibits at least 50% or greater homology or identity to a reference amino acid sequence (for example, any one of the amino acid sequences described herein) or nucleic acid sequence (for example, any one of the nucleic acid sequences described herein). For example, such a sequence is at least about 60%, about 65%, about 70%, about 75%, about 80%, about 85%, about 90%, about 95% or about 99% homologous or identical at the amino acid level or nucleic acid to the sequence used for comparison (e.g., a wild-type, or native, sequence). In some embodiments, a substantially homologous or substantially identical polypeptide contains one or more amino acid amino acid substitutions, insertions, or deletions relative to the sequence used for comparison. In some embodiments, a substantially homologous or substantially identical polypeptide contains one or more non-natural amino acids or amino acid analogs, including, D-amino acids and retroinverso amino, to replace homologous sequences.

Sequence homology or sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. In an exemplary approach to determining the degree of identity, a BLAST program may be used, with a probability score between $e^{-3}$ and $e^{-100}$ indicating a closely related sequence.

As used herein, the term "analog" refers to a structurally related polypeptide or nucleic acid molecule having the function of a reference polypeptide or nucleic acid molecule.

As used herein, the term "a conservative sequence modification" refers to an amino acid modification that does not significantly affect or alter the binding characteristics of the presently disclosed anti-LGALS3 antibody or an antigen-binding fragment thereof comprising the amino acid sequence. Conservative modifications can include amino acid substitutions, additions and deletions. Modifications can be introduced into the human scFv of the presently disclosed anti-LGALS3 antibody or an antigen-binding fragment thereof by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (1) above) using the functional assays described herein. In certain embodiments, no more than one, no more than two, no more than three, no more than four, no more than five residues within a specified sequence or a CDR region are altered.

As used herein, the term "heterologous nucleic acid molecule or polypeptide" refers to a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

As used herein, the term "modulate" refers positively or negatively alter. Exemplary modulations include an about 1%, about 2%, about 5%, about 10%, about 25%, about 50%, about 75%, or about 100% change.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%), 1%), 0.5%), or 0.1%) of other material, e.g., cellular material, culture medium, other nucleic acid molecules, chemical precursors and/or other chemicals.

As used herein, the term "isolated cell" refers to a cell that is separated from the molecular and/or cellular components that naturally accompany the cell.

An "effective amount" (or "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease (e.g., a neoplasia), or otherwise reduce the pathological consequences of the disease (e.g., a neoplasia). The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the engineered immune cells administered.

As used herein, the term "neoplasia" refers to a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasia can affect a variety of cell types, tissues, or organs, including but not limited to an organ selected from the group consisting of bladder, colon, bone, brain, breast, cartilage, glia, esophagus, fallopian tube, gallbladder, heart, intestines, kidney, liver, lung, lymph node, nervous tissue, ovaries, pleura, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasia include cancers, such as sarcomas, carcinomas, or plasmacytomas (malignant tumor of the plasma cells).

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject" refers to any animal (e.g., a mammal), including, but not limited to, humans, non-human primates, rodents, and the like (e.g., which is to be the recipient of a particular treatment, or from whom cells are harvested).

Overview

Galectin-3 (LGALS3) is a β-galactoside-binding protein that is secreted from many cells although the protein lacks a signal sequence for transfer into the endoplasmic reticulum and Golgi compartments and entry into classical secretory pathways. LGALS3 is found in cellular and extracellular locations of the cell and has pleiotropic biological functions such as cell growth, cell adhesion and cell-cell interaction. It may exhibit anti or pro-apoptotic activity depending on its localization and post-translational modifications, such as cleavage and phosphorylation. Cleavage of galectin-3 was reported to be involved with angiogenic potential and apoptotic resistance. Phosphorylation of galectin-3 regulates its sugar-binding ability.

Figure 2B:
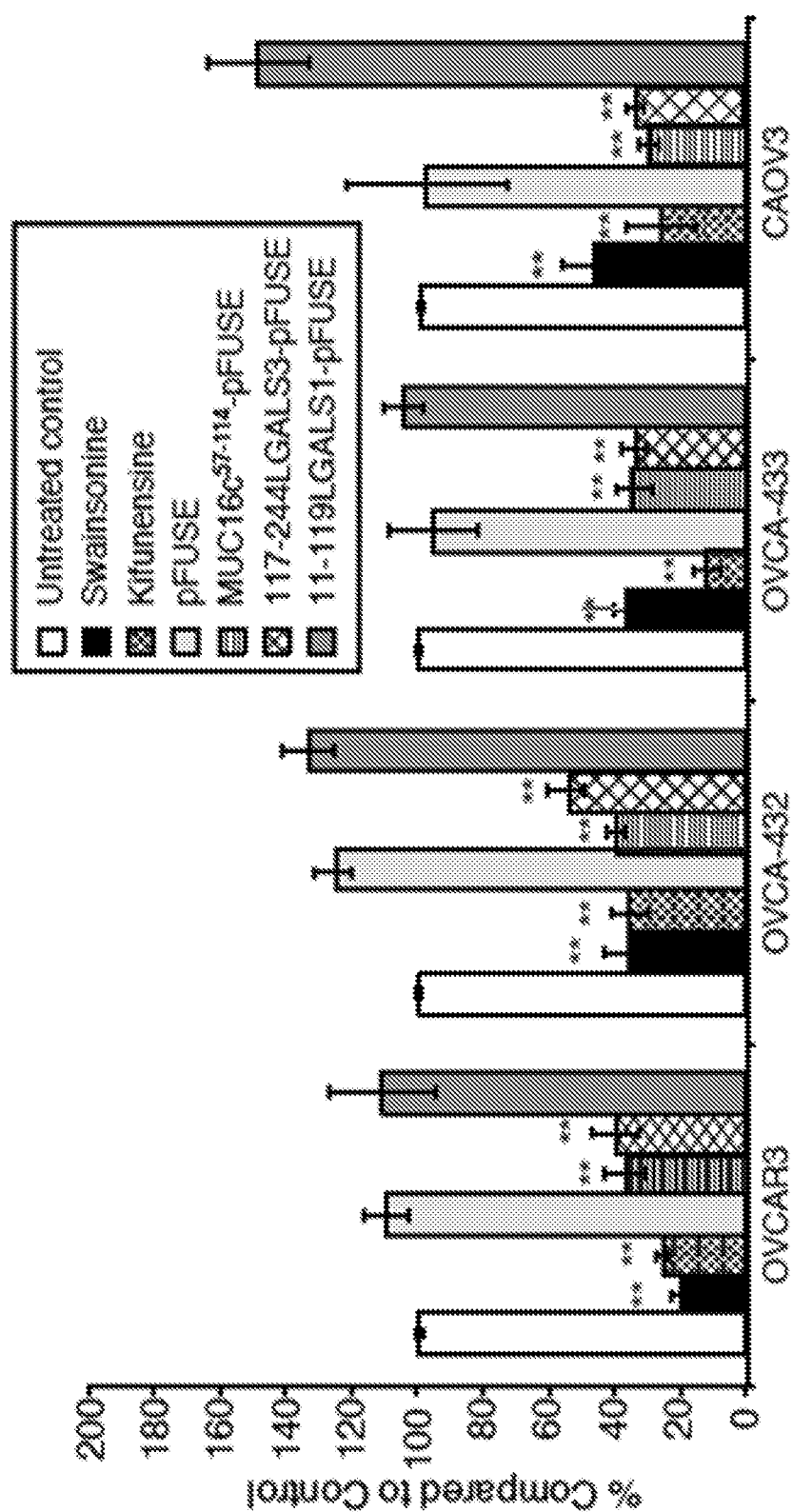
FIG. 2B illustrates competing LGALS3 but not LGAL1 (Galectin-1) blocks Matrigel invasion of ovarian cancer cell lines, OVCAR3, OVCA-432, OVCA-433 and CAOV3. The carbohydrate binding domain of LGALS3 ($^{117-244}$LGAL3-pFUSE), but not $^{11-119}$LGAL1-pFUSE block ovarian cancer cell invasion. Swainsonine and Kifunensine both block the synthesis of the LGALS3 ligand, polylactosamine.
Figure 2C:
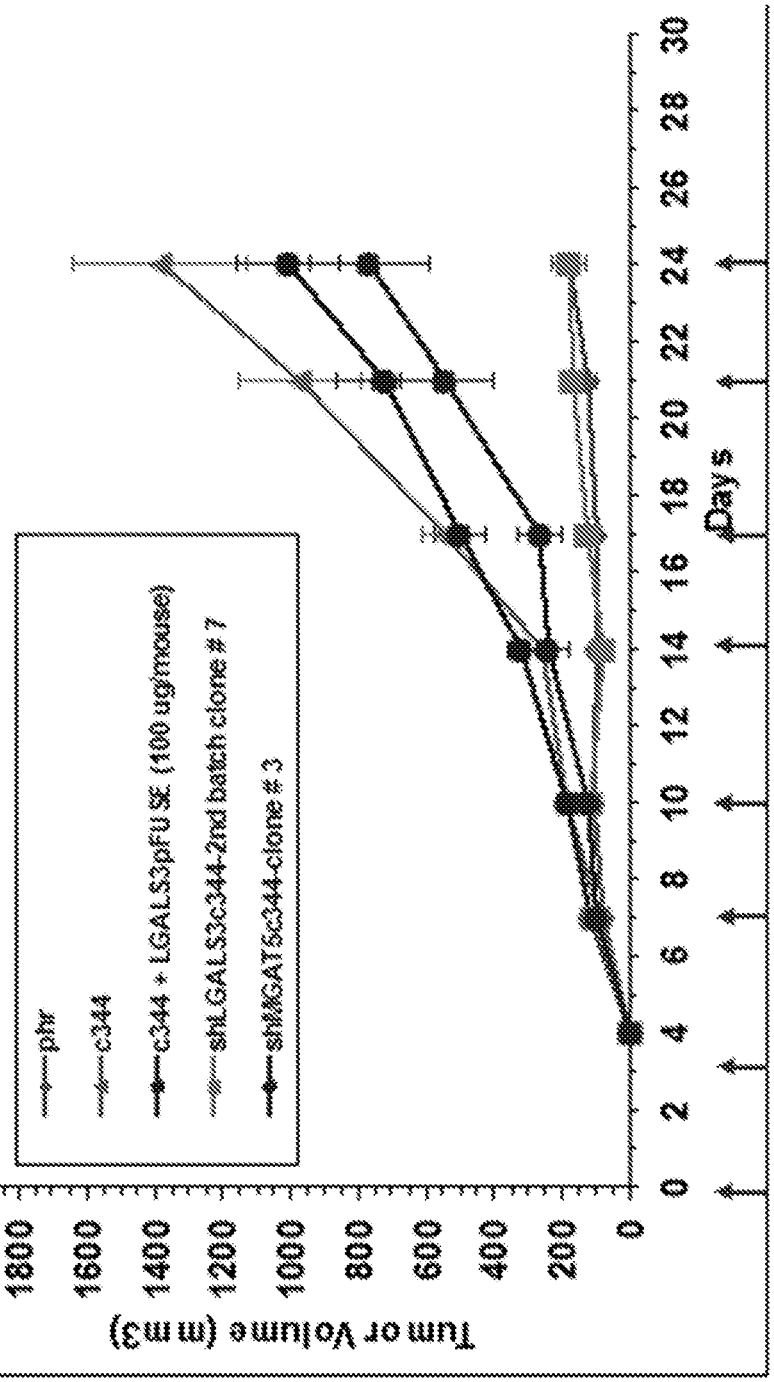
FIG. 2C illustrates inhibition of A2780 Ovarian Cancer in a tumor xenograft model by inhibitors of LGALS3 function. Loss of LGALS3 expression by shLGALS3 inhibition is highly inhibitory. Modest inhibition of tumor growth was also observed by the low affinity protodrug LGALS3-pFUSE which is a fusion protein of the unmodified carbohydrate binding domain of LGALS3 linked to an Fc backbone.
Figure 2D:
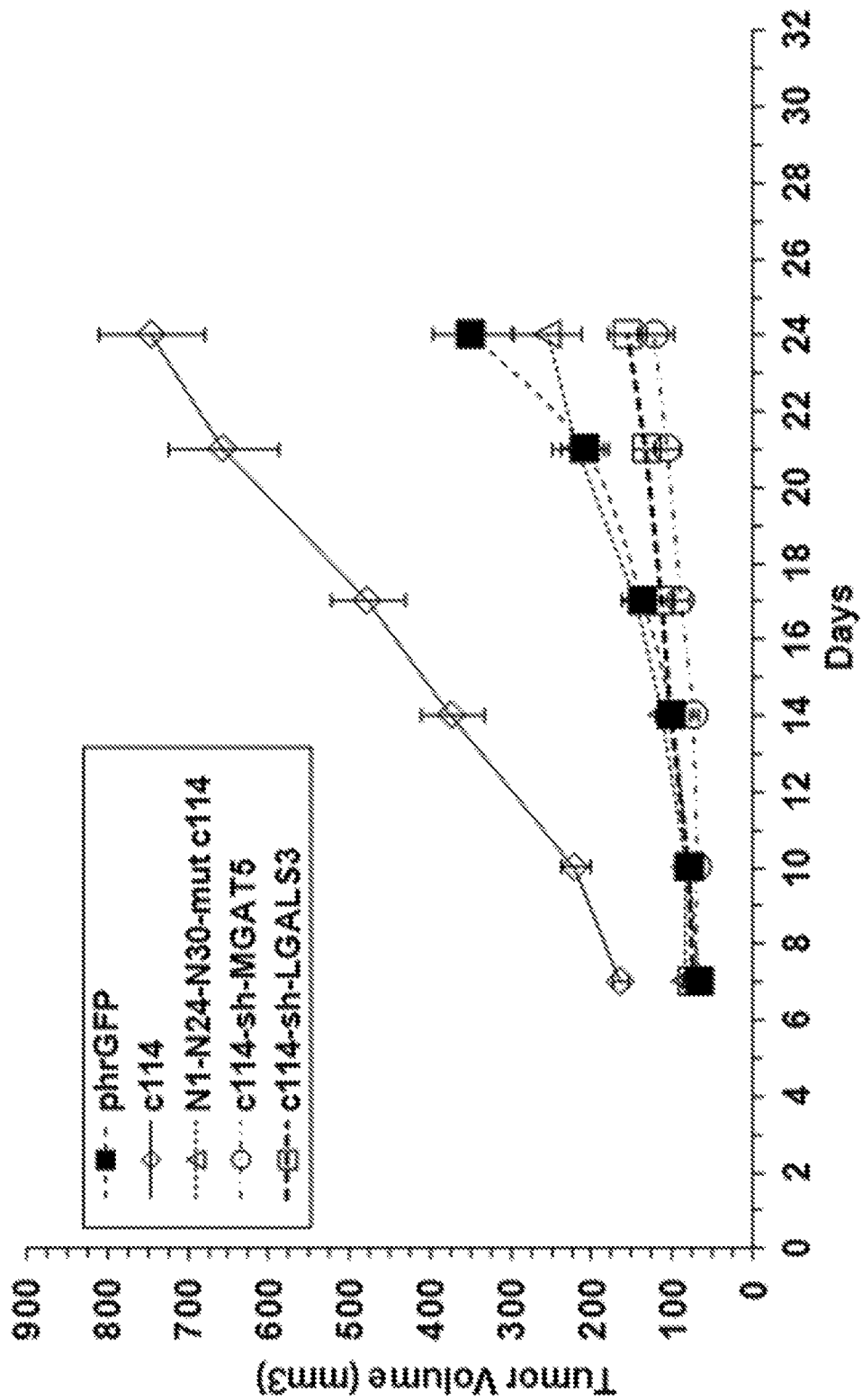
FIG. 2D illustrates antisense knockdowns of MGAT5 and LGALS3 inhibit tumor growth. In SKOV3 cells, MUC16 expression enhanced tumor growth (top line). By contrast, loss of N-glycosylation sites, or shRNA against MGAT5 or LGALS3 reduced growth back to control levels.

Preliminary studies by the inventors in ovarian cancer using an artificially synthesizes chimeric LGALS3 have established that LGALS3 plays an essential role of the growth, spread and invasive properties of ovarian cancer (Rao, et al. (2017) ACS Chem. Biol. 12 (8): 2085-2096, which is incorporated by reference in its entirety). This work utilized both knockdown shRNA suppression of LGALS3 and chimeric antibodies in which the native, low affinity LGALS3 carbohydrate binding domain replaced the antibody variable region. In knockdown experiments, it was shown that tumor expression of LGALS3 is required for the oncogene activating effects of the ovarian cancer mucin MUC16/CA125 (FIG. 2A). When LGALS3 knockdown cells were transplanted in nude mice, they had very limited growth, confirming the essential role of LGALS3 for in vivo tumor growth (FIG. 2D). It was further demonstrated that growth/invasion enhancement by LGALS3 is extracellular. In invasion studies, it was shown that Matrigel invasion of ovarian cancer cells is dependent on LGALS3. Low affinity chimeric antibodies comprising a fusion protein of the unmodified carbohydrate binding domain of LGALS3 linked to an Fc backbone, can block LGALS3 function and prevent Matrigel gel invasion while chimeric blocking antibodies for Galectin-1 were ineffective (FIG. 2B). In addition, introduction of the low affinity, chimeric anti-LGALS3 blocking antibodies reduce in vivo growth of xenografts in mice (FIG. 2C). These chimeric antibodies had no notable adverse effects on the host mice, consistent with the reported minimal effect of LGAL33 knockouts (Wright et al., (2017) J Leukoc Biol 101(3): 717-726.

Described herein is an immunization strategy to isolate inhibitory, high affinity antibodies to LGALS3. The primary sequence of the LGALS3 carbohydrate binding domain (CBD) is illustrated in FIG. 4. The box depicts C, D and E domains of the CBD, which are important for lactosamine binding. The highly conserved amino acids are underlined. R186(*) is important to the functions of GAL3. The GAL3 CBD sequence is highly homologous to the murine Galectin-3 but differs from GAL1, GAL7 and GAL9. While each of these family members have similar sugar binding domains, LGALS3 is the only lectin with the polymerization domain. As described in the examples herein, in order to generate antibodies to the LGALS3 CBD, mice were immunized with peptides and/or fusion constructs containing the LGALS3 CBD, or portions thereof. anti-LGALS3 CBD antibodies were screened against whole proteins CBD and whole proteins for GAL1, LGALS3, GAL7 and GAL9 for antibody selection. The isolated antibodies bind to native human LGALS3 and the mouse homolog Lgal3. In addition, the antibodies exhibited functional inhibition LGALS3 binding to polylactosamine on laminin. Selected antibodies were further shown to inhibit tumor cell invasion as assessed by a Matrigel gel invasion assay and increase survival in a mouse ovarian cancer xenograft model.

A variety of studies have demonstrated a role for LGALS3 in tumor biology and inflammation. A partial list of effects and the anticipated result of LGALS3 targeting are shown in FIG. 3. Many of the anticipated effects are expected beneficial in a cancer treatment. Although the effects of LGALS3 are protean, even complete loss of LGALS3 in a knockout mouse model is consistent with nearly normal development, and some immunosuppressive effects are not substantially different than TNF inhibitors. Based on these studies, the antibodies provided herein are expected to be useful therapeutics for the treatment of a LGALS3-mediated diseases and conditions, including but not limited to cancer and inflammation.

Provided are antibodies and antigen-binding fragments thereof, and polypeptides including such antibodies or fragments, such as fusion proteins, conjugates, and/or chimeric antigen receptors, as well as cells expressing the same. Among the antibodies and fragments are those that specifically bind to epitopes of a LGALS3 protein. Such antibodies are referred to herein as "anti-LGALS3 antibodies." Such epitopes are typically epitopes within or substantially within a carbohydrate binding portion (CBD) of a LGALS3 molecule. In some embodiments, the epitope is within or includes amino acid residues 117-244 of LGALS3 (SEQ ID NO:1). In some embodiments, the antibody or fragment binds to an epitope within or that includes amino acid residues 117-244 of LGALS3 (SEQ ID NO:1). In some embodiments, the epitope is within or includes amino acid residues 152-195 of LGALS3 (SEQ ID NO:1). In some embodiments, the antibody or fragment binds to an epitope within or that includes amino acid residues 152-195 of LGALS3 (SEQ ID NO:1). In some embodiments, the epitope is within or includes amino acid residues 170-186 of LGALS3 (SEQ ID NO:1). In some embodiments, the antibody or fragment binds to an epitope within or that includes amino acid residues 170-186 of LGALS3 (SEQ ID NO:1). In some embodiments, the epitope is portion of the CBD comprising the sequence CNTKLDNNWGREERQSVFPFESG (SEQ ID NO: 2). In some embodiments, the antibody or fragment binds to an epitope within or that includes CNTKLDNNWGREERQSVFPFESG (SEQ ID NO: 2). In some embodiments, the epitope is within or includes domains C, D, and E of the CBD of LGALS3. In some embodiments, the antibody or fragment binds to an epitope within or that includes amino acid residues 170-186 of LGALS3 (SEQ ID NO:1).

In some embodiments, the anti-LGALS3 antibodies and antigen-binding fragments thereof described herein inhibit laminin binding by LGALS3.

In some embodiments, the anti-LGALS3 antibodies and antigen-binding fragments thereof described herein inhibit binding of LGALS3 to lactosamine.

In some embodiments, the anti-LGALS3 antibodies and antigen-binding fragments thereof described herein inhibit or treat cancer. In some embodiments, the anti-LGALS3 antibodies and antigen-binding fragments thereof described herein inhibit invasion and growth of tumor cells. In some embodiments, the anti-LGALS3 antibodies and antigen-binding fragments thereof described herein inhibit tumor angiogenesis. In some embodiments, the anti-LGALS3 antibodies and antigen-binding fragments thereof described herein inhibit metastasis. In some embodiments, the anti-LGALS3 antibodies and antigen-binding fragments thereof described herein inhibit growth of a metastatic tumor. In some embodiments, the anti-LGALS3 antibodies and antigen-binding fragments thereof described herein inhibit activation of cancer-related signaling molecules, such as AKT or ERK.

In some embodiments, the anti-LGALS3 antibodies and antigen-binding fragments thereof described herein inhibit induction of T-cell apoptosis by LGALS3.

In some embodiments, the anti-LGALS3 antibodies and antigen-binding fragments thereof described herein inhibit immunosuppression of T-cells.

In some embodiments, the anti-LGALS3 antibodies and antigen-binding fragments thereof described herein inhibit or treat cardiovascular disease. In some embodiments, the anti-LGALS3 antibodies and antigen-binding fragments thereof described herein inhibit or treat heart failure, coronary heart disease or myocardial infarction.

In some embodiments, the anti-LGALS3 antibodies and antigen-binding fragments thereof described herein inhibit or treat pulmonary fibrosis.

In some embodiments, the anti-LGALS3 antibodies and antigen-binding fragments thereof described herein inhibit or treat renal disease. In some embodiments, the anti-LGALS3 antibodies and antigen-binding fragments thereof described herein inhibit or treat glomerulonephritis. In some embodiments, the anti-LGALS3 antibodies and antigen-binding fragments thereof described herein inhibit or treat renal cell carcinoma.

Also provided herein are polynucleotides (e.g., isolated polynucleotides) comprising nucleic acid sequences (e.g., complementary DNA (cDNA)), encoding such antibodies, and antigen-binding fragments thereof, heavy chains, or light chains. Further provided are vectors (e.g., expression vectors) and cells (e.g., isolated cells or ex vivo cells) comprising polynucleotides (e.g., isolated polynucleotides) comprising nucleic acid sequences (e.g., complementary DNA (cDNA)), encoding such antibodies, and antigen-binding fragments thereof, heavy chains, or light chains. Also provided are methods of making such antibodies, antigen-binding fragments thereof, heavy chains, light chains, vectors, and cells. In other aspects, provided herein are methods and uses for anti-LGALS3 antibodies for treating or managing certain conditions or disorders described herein, such as treating or managing cancer. Related compositions (e.g., pharmaceutical compositions), kits, and diagnostic methods are also provided.

As used herein, the term "LGALS3," "LGALS3 polypeptide," "LGALS3 peptide" "Gal-3," "Gal-3 polypeptide," or "Gal-3 peptide" are used interchangeable herein to refer to Galectin-3 and functional homologs and fragments thereof that bind to β-galactosides. GenBank™ accession number NM_002306.3 (SEQ ID NO: 3) provides an exemplary human LGALS3 nucleic acid sequence. GenBank™ accession number NP_002297.2 (SEQ ID NO: 4) provides an exemplary human LGALS3 amino acid sequence.

Anti-LGALS3 Antibodies

Anti-LGALS3 antibodies or antigen-binding fragments thereof can include, e.g., monoclonal antibodies, polyclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, single domain antibodies, monovalent antibodies, single chain antibodies or single-chain variable fragments (scFv), camelized antibodies, affibodies, and disulfide-linked Fvs (dsFv), or fragments thereof. Such antibodies can be made by methods known in the art.

A multispecific antibody or fragment thereof refers to an antibody or fragment thereof that can bind simultaneously to at least two targets that are of different structure, e.g., two different antigens, two different epitopes on the same antigen, or a hapten and an antigen or epitope. One specificity could be for, for example, a B-cell, T-cell, myeloid-, plasma-, or mast-cell antigen or epitope, such as, for example CD3. Another specificity could be to a different antigen on the same or different cell type, such as for example, LGALS3. Multispecific, multivalent antibodies are constructs that have more than one binding site, and the binding sites are of different specificity, for example, a bispecific diabody, where one binding site reacts with one antigen and the other with another antigen.

A bispecific antibody is an antibody that can bind simultaneously to two targets which are of different structure. Bispecific antibodies (bsAb) and bispecific antibody fragments (bsFab) have at least one arm that immunospecifically binds to a first target, for example, LGALS3, and at least one other arm that immunospecifically binds to a second target, such as, for example, CD3. A variety of bispecific fusion proteins can be produced using molecular engineering. In one form, the bispecific fusion protein is divalent, consisting of, for example, (i) a scFv with a single binding site for one antigen and (ii) an antibody or a Fab fragment with a single binding site for a second antigen. In another form, the bispecific fusion protein is tetravalent, consisting of, for example, an IgG with two binding sites for one antigen and two identical scFv for a second antigen. See, for example, International Publication No. WO 2011/1160119, which is incorporated by reference in its entirety herein.

Recent methods for producing bispecific monoclonal antibodies include the use of engineered recombinant monoclonal antibodies which have additional cysteine residues so that they crosslink more strongly than the more common immunoglobulin isotypes. See, e.g., FitzGerald et al., Protein Eng. 10(10): 1221-1225, 1997. Another approach is to engineer recombinant fusion proteins linking two or more different single-chain antibody or antibody fragment segments with the needed dual specificities. See, e.g., Coloma et al., Nature Biotech. 15: 159-163, 1997. A variety of bispecific fusion proteins can be produced using molecular engineering.

Bispecific fusion proteins linking two or more different single-chain antibodies or antibody fragments can be produced in similar manner. Recombinant methods can be used to produce a variety of fusion proteins. In certain aspects, a flexible linker connects an scFv (e.g., an scFv targeting CD3) to the constant region of the light chain of a monoclonal antibody (e.g., an anti-LGALS3 antibody described herein). Appropriate linker sequences necessary for the in-frame connection of the heavy chain Fc to the scFv are introduced into the VL and Vkappa domains through PCR reactions. The DNA fragment encoding the scFv is then ligated into a staging vector containing a DNA sequence encoding the CH1 domain. The resulting construct is excised and ligated into a vector containing a DNA sequence encoding the VH region of the antibody (e.g., the anti-LGALS3 antibody). The resulting vector can be used to transfect an appropriate host cell, such as a mammalian cell for the expression of the bispecific fusion protein.

The anti-LGALS3 antibodies described herein and fragments thereof in certain embodiments can also be used to prepare functional bispecific single-chain antibodies (bscAb), also called diabodies, and can be produced in mammalian cells using recombinant methods. See, e.g., Mack et al., Proc. Natl. Acad. Sci., 92: 7021-7025, 1995, incorporated herein by reference. For example, bscAb can be produced by joining two single-chain Fv fragments via a glycine-serine linker using recombinant methods. The VL and VH domains of two antibodies of interest are isolated using standard PCR methods known in the art. Bispecific single-chain antibodies and bispecific fusion proteins are included within the scope of the present invention.

In certain embodiments, anti-LGALS3 antibodies or antigen-binding fragments thereof described herein refer to scFvs. A scFv is an art-recognized term. An scFv comprises a fusion protein of the variable regions of the heavy (VH) and light (VL) chains of an immunoglobulin, wherein the fusion protein retains the same antigen specificity as the whole immunoglobulin. The VH is fused to the VL via a peptide linker. In certain embodiments, the peptide linker is between 5 and 25, 5 and 15, 10 and 20, 10 and 15, or 15 and 25 amino acid residues in length. In certain embodiments, the scFv peptide linker displays one or more characteristics suitable for a peptide linker known to one of ordinary skill in the art. In certain embodiments, the scFv peptide linker comprises amino acids that allow for scFv peptide linker solubility, such as, for example, serine and threonine. In certain embodiments, the scFv peptide linker comprises amino acids that allow for scFv peptide linker flexibility, such as, for example, glycine. In certain embodiments, the scFv peptide linker connects the N-terminus of the VH to the C-terminus of the VL. In certain embodiments, the scFv peptide linker can connect the C-terminus of the VH to the N-terminus of the VL.

In certain embodiments, anti-LGALS3 antibodies or antigen-binding fragments thereof described herein refer to chimeric antigen receptors (CARs). A CAR is an art-recognized term. A CAR can be targeted to a tumor associated antigen (e.g., LGALS3). CARs as provided herein typically are composed of a scFv derived from a LGALS3 Glycosylation Antibody, a transmembrane domain, which in some embodiments is a T cell costimulatory molecule-derived transmembrane domain (for example, a transmembrane domain derived from CD28, CD8, CD38, OX-40, or 4-1BB), and a primary signaling domain, such as the T cell receptor (TCR) zeta ($\zeta$) chain cytoplasmic signaling domain. In some embodiments, the CAR further includes one or more additional regions or domains such as one or more spacer or linker, including an extracellular spacer, such as one derived from an antibody or other cell-surface molecule, such as a spacer containing gone or more of antibody CH2, CH3, and/or hinge regions, or a spacer derived from a CD28 molecule or a CD8 molecule, or other spacer. Also provided herein are cells, such as T cells engineered to express such CARs, such as those recombinantly expressing such a CAR. A CAR-expressing T cell, upon recognition of a LGALS3 expressing tumor, preferably induces T cell activation, proliferation, and/or lysis of a cell of such a tumor.

Anti-LGALS3 antibodies can be of any type (e.g., IgG, IgE, IgM, IgD, IgA or IgY), any class (e.g., IgG1, IgG2, IgG3, IgG4, IgA1 or IgA2), or any subclass (e.g., IgG2a or IgG2b) of immunoglobulin molecule. In certain embodiments, antibodies described herein are IgG antibodies, or a class or subclass thereof. In certain embodiments, antibodies described herein are IgG1 antibodies. In certain embodiments, antibodies described herein are IgG2 antibodies. In certain embodiments, antibodies described herein are IgG2a antibodies. In certain embodiments, antibodies described herein are IgG2b antibodies. In certain embodiments, antibodies described herein are IgG3 antibodies. In certain embodiments, antibodies described herein are IgG4 antibodies. In certain embodiments, antibodies described herein are a mixture of antibody types or a mixture of subclasses. In certain embodiments, antibodies described herein are a mixture of IgG2a and IgG2b antibodies. In a specific embodiment, the antibody is a humanized form of a rodent monoclonal antibody.

Antigen binding fragments of anti-LGALS3 antibodies can be Fab fragments, F(ab')2 fragments, or a portion of anti-LGALS3 antibody which comprises the amino acid residues that confer on the anti-LGALS3 antibody its specificity for the antigen (e.g., the complementarity determining regions (CDR)). The anti-LGALS3 antibody can be derived from any animal species, such as rodents (e.g., mouse, rat or hamster) and humans.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids in a mature heavy chain and about the amino-terminal 90 to 100 amino acids in a mature light chain, which differs extensively in sequence among antibodies and is used in the binding and specificity of a particular antibody for its particular antigen. The variability in sequence is concentrated in those regions called complementarity determining regions (CDRs) while the more highly conserved regions in the variable domain are called framework regions (FR). CDRs are flanked by FRs. Generally, the spatial orientation of CDRs and FRs are as follows, in an N-terminal to C-terminal direction: FR1-CDR1-FR2-CDR2-FR3-CDR3-FR4. Without wishing to be bound by any particular mechanism or theory, it is believed that the CDRs of the light and heavy chains are primarily responsible for the interaction and specificity of the antibody with antigen. In certain embodiments, the variable region is a rodent (e.g., mouse or rat) variable region. In certain embodiments, the variable region is a human variable region. In certain embodiments, the variable region comprises rodent (e.g., mouse or rat) CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

CDRs are defined in various ways in the art, including the Kabat, Chothia, and IMGT, and Exemplary definitions. The Kabat definition is based on sequence variability (Kabat, Elvin A. et al., Sequences of Proteins of Immunological Interest. Bethesda: National Institutes of Health, 1983). With respect to the Kabat numbering system, (i) the VH CDR1 is typically present at amino acid positions 31 to 35 of the heavy chain, which can optionally include one or two additional amino acids following amino acid position 35 (referred to in the Kabat numbering scheme as 35 A and 35B); (ii) the VH CDR2 is typically present at amino acid positions 50 to 65 of the heavy chain; and (iii) the VH CDR2 is typically present at amino acid positions 95 to 102 of the heavy chain (Kabat, Elvin A. et al., Sequences of Proteins of Immunological Interest. Bethesda: National Institutes of Health, 1983). With respect to the Kabat numbering system, (i) the VL CDR1 is typically present at amino acid positions 24 to 34 of the light chain; (ii) the VL CDR2 is typically present at amino acid positions 50 to 56 of the light chain; and (iii) the VL CDR3 is typically present at amino acid positions 89 to 97 of the light chain (Kabat, Elvin A. et al., Sequences of Proteins of Immunological Interest. Bethesda: National Institutes of Health, 1983). As is well known to those of skill in the art, using the Kabat numbering system, the actual linear amino acid sequence of the antibody variable domain can contain fewer or additional amino acids due to a shortening or lengthening of a FR and/or CDR and, as such, an amino acid's Kabat number is not necessarily the same as its linear amino acid number.

The Chothia definition is based on the location of the structural loop regions (Chothia et al. (1987) *J Mol Biol* 196: 901-917; and U.S. Pat. No. 7,709,226). The term "Chothia CDRs," and like terms are recognized in the art and refer to antibody CDR sequences as determined according to the method of Chothia and Lesk (1987) *J Mol. Biol.* 196:901-917, which will be referred to herein as the "Chothia CDRs" (see also, e.g., U.S. Pat. No. 7,709,226 and Martin, A., "Protein Sequence and Structure Analysis of Antibody Variable Domains," in Antibody Engineering, Kontermann and Diibel, eds., Chapter 31, pp. 422-439, Springer-Verlag, Berlin (2001)). With respect to the Chothia numbering system, using the Kabat numbering system of numbering amino acid residues in the VH region, (i) the VH CDR1 is typically present at amino acid positions 26 to 32 of the heavy chain; (ii) the VH CDR2 is typically present at amino acid positions 53 to 55 of the heavy chain; and (iii) the VH CDR3 is typically present at amino acid positions 96 to 101 of the heavy chain. In a specific embodiment, with respect to the Chothia numbering system, using the Kabat numbering system of numbering amino acid residues in the VH region, (i) the VH CDR1 is typically present at amino acid positions 26 to 32 or 34 of the heavy chain; (ii) the VH CDR2 is typically present at amino acid positions 52 to 56 (in one embodiment, CDR2 is at positions 52A-56, wherein 52A follows position 52) of the heavy chain; and (iii) the VH CDR3 is typically present at amino acid positions 95 to 102 of the heavy chain (in one embodiment, there is no amino acid at positions numbered 96-100). With respect to the Chothia numbering system, using the Kabat numbering system of numbering amino acid residues in the VL region, (i) the VL CDR1 is typically present at amino acid positions 26 to 33 of the light chain; (ii) the VL CDR2 is typically present at amino acid positions 50 to 52 of the light chain; and (iii) the VL CDR3 is typically present at amino acid positions 91 to 96 of the light chain. In a specific embodiment, with respect to the Chothia numbering system, using the Kabat numbering system of numbering amino acid residues in the VL region, (i) the VL CDR1 is typically present at amino acid positions 24 to 34 of the light chain; (ii) the VL CDR2 is typically present at amino acid positions 50 to 56 of the light chain; and (iii) the VL CDR3 is typically present at amino acid positions 89 to 97 of the light chain (in one embodiment, there is no amino acid at positions numbered 96-100). These Chothia CDR positions may vary depending on the antibody, and can be determined according to methods known in the art.

The IMGT definition is from the EVIGT ("IMGT®, the international ImMunoGeneTics information System® website imgt.org, founder and director: Marie-Paule Lefranc, Montpellier, France; see, e.g., Lefranc, M. P., 1999, The Immunologist, 7: 132-136 and Lefranc, M. P. et al., 1999, Nucleic Acids Res., 27:209-212, both of which are incorporated herein by reference in their entirety). With respect to the IMGT numbering system, (i) the VH CDR1 is typically present at amino acid positions 25 to 35 of the heavy chain; (ii) the VH CDR2 is typically present at amino acid positions 51 to 57 of the heavy chain; and (iii) the VH CDR2 is typically present at amino acid positions 93 to 102 of the heavy chain. With respect to the IMGT numbering system, (i) the VL CDR1 is typically present at amino acid positions 27 to 32 of the light chain; (ii) the VL CDR2 is typically present at amino acid positions 50 to 52 of the light chain; and (iii) the VL CDR3 is typically present at amino acid positions 89 to 97 of the light chain.

Sequences and Structures of LGALS3 Antibodies

In certain embodiments, provided herein is an anti-LGALS3 antibody or antigen-binding fragment thereof which comprises VH CDRs of any of the anti-LGALS3 antibodies provided herein, e.g., as set forth in FIGS. 12*a*, 12*b* and 13A-O. In certain embodiments, an anti-LGALS3 antibody or antigen-binding fragment thereof provided herein comprises the VH CDR1 of an anti-LGALS3 antibody as set forth in FIG. 12a. In certain embodiments, an anti-LGALS3 antibody or antigen-binding fragment thereof provided herein comprises the VH CDR2 of an anti-LGALS3 antibody as set forth in FIG. 12a. In certain embodiments, an anti-LGALS3 antibody or antigen-binding fragment thereof provided herein comprises the VH CDR3 of an anti-LGALS3 antibody as set forth in FIG. 12a. In certain embodiments, an anti-LGALS3 antibody or antigen-binding fragment thereof provided herein comprises one, two or all three of VH CDRs of an anti-LGALS3 antibody as set forth in Table FIG. 12a.

In certain embodiments, provided herein is an anti-LGALS3 antibody or antigen-binding fragment thereof which comprises VL CDRs of any of the anti-LGALS3 antibodies provided herein, e.g., as set forth in FIGS. 12 and 13. In certain embodiments, an anti-LGALS3 antibody or antigen-binding fragment thereof provided herein comprises the VL CDR1 of an anti-LGALS3 antibody as set forth in FIG. 12b. In certain embodiments, an anti-LGALS3 antibody or antigen-binding fragment thereof provided herein comprises the VL CDR2 of an anti-LGALS3 antibody as set forth in FIG. 12b. In certain embodiments, an anti-LGALS3 antibody or antigen-binding fragment thereof provided herein comprises the VL CDR3 of an anti-LGALS3 antibody as set forth in FIG. 12b. In certain embodiments, an anti-LGALS3 antibody or antigen-binding fragment thereof provided herein comprises one, two or all three of VL CDRs of an anti-LGALS3 antibody in FIG. 12b.

In certain embodiments, provided herein is an anti-LGALS3 antibody or antigen-binding fragment thereof which comprises VH CDRs of any of the anti-LGALS3 antibodies provided herein, e.g., as set forth in FIGS. 13A-C. In certain embodiments, an anti-LGALS3 antibody or antigen-binding fragment thereof provided herein comprises the VH CDR1 of an anti-LGALS3 antibody as set forth in FIGS. 13A-C. In certain embodiments, an anti-LGALS3 antibody or antigen-binding fragment thereof provided herein comprises the VH CDR2 of an anti-LGALS3 antibody as set forth in FIGS. 13A-C. In certain embodiments, an anti-LGALS3 antibody or antigen-binding fragment thereof provided herein comprises the VH CDR3 of an anti-LGALS3 antibody as set forth in FIGS. 13A-C. In certain embodiments, an anti-LGALS3 antibody or antigen-binding fragment thereof provided herein comprises one, two or all three of VH CDRs of an anti-LGALS3 antibody as set forth in FIGS. 13A-C.

In certain embodiments, provided herein is an anti-LGALS3 antibody or antigen-binding fragment thereof which comprises VL CDRs of any of the anti-LGALS3 antibodies provided herein, e.g., as set forth in FIGS. 13A-C. In certain embodiments, an anti-LGALS3 antibody or antigen-binding fragment thereof provided herein comprises the VH CDR1 of an anti-LGALS3 antibody as set forth in FIGS. 13A-C. In certain embodiments, an anti-LGALS3 antibody or antigen-binding fragment thereof provided herein comprises the VH CDR2 of an anti-LGALS3 antibody as set forth in FIGS. 13A-C. In certain embodiments, an anti-LGALS3 antibody or antigen-binding fragment thereof provided herein comprises the VH CDR3 of an anti-LGALS3 antibody as set forth in FIGS. 13A-C. In certain embodiments, an anti-LGALS3 antibody or antigen-binding fragment thereof provided herein comprises one, two or all three of VL CDRs of an anti-LGALS3 antibody in FIGS. 13A-C.

In a particular embodiment, an anti-LGALS3 antibody or antigen-binding fragment thereof described herein, comprises a VH which comprises: (a) a VH CDR1 comprising the amino acid sequence SYGVH (SEQ ID NO: 5); (b) a VH CDR2 comprising the amino acid sequence VIWSDGSTTYNSTLKS (SEQ ID NO: 6); and (c) a VH CDR3 comprising the amino acid sequence HISNYGTMDY (SEQ ID NO: 7).

In a particular embodiment, an anti-LGALS3 antibody or antigen-binding fragment thereof an anti-LGALS3 antibody or antigen-binding fragment thereof described herein comprises a VH which comprises a VH CDR1 comprising the amino acid sequence of SEQ ID NO: 11 or 17, a VH CDR2 comprising the amino acid sequence of SEQ ID NO:12 or 18, and a VH CDR3 comprising the amino acid sequence of SEQ ID NO:13 or 19.

In a particular embodiment, an anti-LGALS3 antibody or antigen-binding fragment thereof an anti-LGALS3 antibody or antigen-binding fragment thereof described herein comprises a VL which comprises: (a) a VL CDR1 comprising the amino acid sequence RASQDIRNYLN (SEQ ID NO: 8) (b) a VL CDR2 comprising the amino acid sequence YTSRLHS (SEQ ID NO: 9); and (c) a VL CDR3 comprising the amino acid sequence QHFNTLPPT (SEQ ID NO: 10).

In a particular embodiment, an anti-LGALS3 antibody or antigen-binding fragment thereof described herein comprises a VL which comprises a VL CDR1 comprising the amino acid sequence of SEQ ID NO:14 or 20, a VL CDR2 comprising the amino acid sequence of SEQ ID NO:15 or 21, and a VL CDR3 comprising the amino acid sequence of SEQ ID NO:16 or 22.

In a particular embodiment, an anti-LGALS3 antibody or antigen-binding fragment thereof described herein comprises: (i) a VH which comprises: (a) a VH CDR1 comprising the amino acid sequence SYGVH (SEQ ID NO: 5); (b) a VH CDR2 comprising the amino acid sequence VIWSDGSTTYNSTLKS (SEQ ID NO: 6); and (c) a VH CDR3 comprising the amino acid sequence HISNYGTMDY (SEQ ID NO: 7); and (ii) a VL which comprises: (a) a VL CDR1 comprising the amino acid sequence RASQDIRNYLN (SEQ ID NO: 8); (b) a VL CDR2 comprising the amino acid sequence YTSRLHS (SEQ ID NO: 9); and (c) a VL CDR3 comprising the amino acid sequence QHFNTLPPT (SEQ ID NO: 10).

In a particular embodiment, an anti-LGALS3 antibody or antigen-binding fragment thereof described herein comprises a VH region comprising:

```
                                            (SEQ ID NO: 24)
QVQLKESGPGLVAPSQSLSITCTISGFSLSSYGVHWVRQPPGKGLEWLVV

IWSDGSTTYNSTLKSRLSISKDNSKSQVFLKMNSLQTDDTAMYYCARHIS

NYGTMDYWGQGTSVTVS.
```

In a particular embodiment, an anti-LGALS3 antibody or antigen-binding fragment thereof described herein comprises a VL region comprising:

```
                                            (SEQ ID NO: 26)
DIQMTQTTSSLSASLGDRVTISCRASQDIRNYLNWYQQKPDGSIKLLIYY

TSRLHSGVPSRFSGSGSGTDYSLTIRNLEQEDIATYFCQHFNTLPPTFGG

GTKLEIK
```

In a particular embodiment, an anti-LGALS3 antibody or antigen-binding fragment thereof described herein comprises a VH region comprising a heavy chain set forth in any of FIGS. 13D-O. In a particular embodiment, an anti-LGALS3 antibody or antigen-binding fragment thereof described herein comprises a VL region comprising a light chain set forth in any of FIGS. 13D-O.

In certain embodiments, an anti-LGALS3 antibody or antigen binding fragment thereof described herein can be described by its VH domain alone, or its VL domain alone, or by its three VH CDRs alone, or by its three VL CDRs alone. See, e.g., Rader C et al. (1998) PNAS 95: 8910-8915, which is incorporated herein by reference in its entirety, which describes the humanization of the mouse anti-avP3 antibody by identifying a complementing light chain or heavy chain, respectively, from a human light chain or heavy chain library, resulting in humanized antibody variants having affinities as high or higher than the affinity of the original antibody. See also, Clackson T et al., (1991) *Nature* 352: 624-628, which is incorporated herein by reference in its entirety, describing methods of producing antibodies that bind a specific antigen by using a specific VH domain (or VL domain) and screening a library for the complementary variable domains. See also, Kim and Hong (2007) *J Microbiol* 45: 572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

In certain embodiments, an anti-LGALS3 antibody or antigen binding fragment thereof described herein can be a humanized antibody, for example, a humanized form of a rodent antibody. Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), chain shuffling (U.S. Pat. No. 5,565,332), veneering or resurfacing (European Patent Nos. EP 592,106 and EP 519,596; Padlan (1991) *Molecular Immunology* 28(4/5):489-498; Studnicka et al. (1994) *Protein Engineering* 7(6):805-814; and Roguska et al. (1994) *PNAS* 91:969-973), and techniques disclosed in, e.g., U.S. Pat. Nos. 6,407,213, 5,766,886, WO 9317105, Sandhu (1994) *Gene* 150(2):409-10, Pedersen et al. (1994) *J. Mol. Biol.* 235(3):959-73, Couto et al. (1995) *Cancer Res.* 55(8): 1717-22, Roguska et al. (1996) *Protein Eng.* 9(10):895 904, Baca et al. (1997) *J. Biol. Chem.* 272(16): 10678-84, Couto et al. (1995) *Cancer Res.* 55 (23 Supp):5973s-5977s, Caldas et al. (2000) *Protein Eng.* 13(5): 353-60, Morea et al. (2000) *Methods* 20(3):267-79, and Tan et al. (2002) *J. Immunol.* 169: 1119-25. See also U.S. Patent Pub. No. US 2005/0042664 A1 (Feb. 24, 2005), each of which is incorporated by reference herein in its entirety.

In certain embodiments, an anti-LGALS3 antibody or antigen binding fragment thereof described herein is a composite human antibody. A composite human antibody can be generated by, e.g., designing variable region sequences from fragments of multiple human antibody variable region sequences in a manner that avoids T cell epitopes, thereby minimizing the immunogenicity of the resulting antibody (see, e.g., Baker et al. (2010) *Self Nonself* 1 (4):314-322; Bryson et al. (2010) *BioDrugs* 24(1): 1-8; and Jones et al. (2009) *Methods Mol Biol.* 525:405-23). Such antibodies can comprise human constant region sequences, e.g., human light chain and/or heavy chain constant regions.

In certain embodiments, an anti-LGALS3 antibody or antigen binding fragment thereof described herein can be a deimmunized antibody. A deimmunized antibody is an antibody in which T-cell epitopes have been removed. Methods for making deimmunized antibodies have been described. See, e.g., Jones et al. Methods Mol Biol. 2009; 525:405-23, xiv, and De Groot et al. (2006) *Cell. Immunol.* 244: 148-153).

In specific embodiments, an anti-LGALS3 antibody or antigen-binding fragment thereof described herein is a humanized immunoglobulin that comprises the 3 VH CDRs and the 3 VL CDRs (i.e., VH CDR1, VH CDR2, VH CDR3, VL CDR1, VL CDR2, and VL CDR3) of any of the antibodies in FIGS. 12 and 13, human-derived framework regions, and human derived constant regions. Non-limiting examples of human framework regions are described in the art, e.g., see Kabat et al. (1991) Sequences of Proteins of Immunological Interest Fifth Edition, U.S. Department of Health and Human Services, NIH Publication No. 91-3242). In certain embodiment, an anti-LGALS3 antibody or antigen binding fragment thereof described herein comprises framework regions (e.g., framework regions of the VL domain and/or VH domain) that are human framework regions or derived from human framework regions. In certain embodiments, an anti-LGALS3 antibody or antigen binding fragment thereof described herein comprises framework regions (e.g., framework regions of the VL domain and/or VH domain) that are primate (e.g., non-human primate) framework regions or derived from primate (e.g., non-human primate) framework regions. For example, CDRs from antigen-specific non-human antibodies, typically of rodent origin (e.g., mouse or rat), are grafted onto homologous human or non-human primate (e.g., Old World apes, e.g., *Pan troglodytes, Pan paniscus* or *Gorilla, Pan troglodytes*, Old World monkeys, e.g., from the genus *Macaca*, or the cynomolgus monkey *Macaca cynomolgus*). Non-human primate framework sequences are described in U.S. Patent Application Publication No. US 2005/0208625.

In a specific embodiment, the position of VH CDR1, VH CDR2, and/or VH CDR3 in the VH region and/or the position of VL CDR1, VL CDR2, and/or VL CDR2 in the VL region of an anti-LGALS3 antibody or antigen binding fragment thereof described herein may vary by 1, 2, 3, 4, 5, 6, or more amino acid positions so long as immunospecific binding to LGALS3 or a portion thereof containing the carbohydrate binding domain is maintained (e.g., by at least 50%, at least 60%, at least 70%, at least 80%, at least 90%, at least 95%).

In another embodiment, the length of VH CDR1, VH CDR2, and/or VH CDR3 in the VH region and/or the length of VL CDR1, VL CDR2, and/or VL CDR2 in the VL region of an anti-LGALS3 antibody or antigen binding fragment thereof described herein may vary (e.g., be shorter or longer) by 1, 2, 3, 4, 5, 6, or more amino acids, so long as immunospecific binding to LGALS3 or a portion thereof containing the carbohydrate binding domain is maintained (e.g., by at least 50%, at least 60%, at least 70%, at least 80%, at least 90%, at least 95%).

In another embodiment, the amino terminus and/or the carboxy terminus of a VH CDR1, VH CDR2, VH CDR3, VL CDR1, VL CDR2, and/or VL CDR3 described herein can be extended or shortened by 1, 2, 3, 4, 5, 6, or more amino acids compared to one or more of the CDRs described herein so long as immunospecific binding to LGALS3 or a portion thereof containing the carbohydrate binding domain is maintained (e.g., by at least 50%, at least 60%, at least 70%, at least 80%, at least 90%, at least 95%).

Any method known in the art can be used to ascertain whether immunospecific binding to LGALS3 is maintained, e.g., ELISA binding assays, SPR analysis, or FACs analysis.

In specific aspects, provided herein is an anti-LGALS3 antibody or antigen-binding fragment thereof comprising an antibody heavy chain and/or light chain, e.g., a heavy chain alone, a light chain alone, or both a heavy chain and a light chain.

In some embodiments, an anti-LGALS3 antibody or an antigen-binding fragment thereof described herein comprises a heavy chain wherein the amino acid sequence of the variable region of the heavy chain comprises a VH CDR1, VH CDR2, and VH CDR3 of any one of antibodies listed in FIG. 12 or 13, and wherein the constant region of the heavy chain is a human heavy chain constant region. In a particular embodiment, an anti-LGALS3 antibody or an antigen-binding fragment thereof described herein comprises a heavy chain wherein the amino acid sequence of the variable region of the heavy chain comprises a VH CDR1, VH CDR2, and VH CDR3 having the amino acid sequences of SEQ ID NO: 5, SEQ ID NO: 6, and SEQ ID NO: 7, respectively, wherein the constant region of the heavy chain is a human heavy chain constant region. In a specific embodiment, an anti-LGALS3 antibody or an antigen-binding fragment thereof described herein comprises a heavy chain wherein the amino acid sequence of the variable region of the heavy chain comprises the amino acid sequence of SEQ ID NO: 24, and wherein the constant region of the heavy chain is a human heavy chain constant region. Non-limiting examples of human constant region sequences have been described in the art, e.g., see Kabat E A et al. (1991) supra.

In some embodiments, the heavy chain of an anti-LGALS3 antibody or an antigen-binding fragment thereof described herein can be an alpha (a), delta (δ), epsilon (c), gamma (γ) or mu (μ) heavy chain. In another specific embodiment, the heavy chain of an anti-LGALS3 antibody or antigen binding fragment thereof described can comprise a human alpha (a), delta (δ), epsilon (ε), gamma (γ) or mu (μ) heavy chain. In some embodiments, an anti-LGALS3 antibody or an antigen-binding fragment thereof described herein comprises a heavy chain wherein the amino acid sequence of the variable region of the heavy chain comprises a VH CDR1, VH CDR2, and VH CDR3 of any one of antibodies listed in FIG. 12 or 13, and wherein the constant region of the heavy chain is an alpha (a), delta (δ), epsilon (c), gamma (γ) or mu (μ) heavy chain. In a particular embodiment, an anti-LGALS3 antibody or an antigen-binding fragment thereof described herein comprises a heavy chain wherein the amino acid sequence of the variable region of the heavy chain comprises a VH CDR1, VH CDR2, and VH CDR3 having the amino acid sequences of SEQ ID NO: 5, SEQ ID NO: 6, and SEQ ID NO: 7, respectively, wherein the constant region of the heavy chain is a human an alpha (a), delta (δ), epsilon (ε), gamma (γ) or mu (μ) heavy chain. In a specific embodiment, an anti-LGALS3 antibody or an antigen-binding fragment thereof described herein comprises a heavy chain wherein the amino acid sequence of the variable region of the heavy chain comprises the amino acid sequence of SEQ ID NO: 24, and wherein the constant region of the heavy chain is a human an alpha (a), delta (δ), epsilon (ε), gamma (γ) or mu (μ) heavy chain.

In a particular embodiment, an anti-LGALS3 antibody or an antigen-binding fragment thereof described herein comprises a light chain wherein the amino acid sequence of the variable region of the light chain comprises a VL CDR1, VL CDR2, and VL CDR3 of any one of antibodies listed in FIG. 12 or 13 and wherein the constant region of the light chain is a human light chain constant region. In a particular embodiment, an anti-LGALS3 antibody or an antigen-binding fragment thereof described herein comprises a light chain wherein the amino acid sequence of the variable region of the light chain comprises a VL CDR1, VL CDR2, and VL CDR3 having the amino acid sequences of antibody SEQ ID NO: 8, SEQ ID NO: 8, and SEQ ID NO: 10, respectively, and wherein the constant region of the light chain is a human light chain constant region. In a specific embodiment, an anti-LGALS3 antibody or an antigen-binding fragment thereof described herein comprises a light chain wherein the amino acid sequence of the variable region of the light chain comprises the amino acid sequence of SEQ ID NO: 26, and wherein the constant region of the light chain is a human light chain constant region.

In some embodiments, the light chain of an anti-LGALS3 antibody or an antigen-binding fragment thereof described herein is a kappa light chain. In another specific embodiment, the light chain of an anti-LGALS3 antibody or an antigen-binding fragment thereof described herein is a lambda light chain. In yet another specific embodiment, the light chain of an anti-LGALS3 antibody or an antigen-binding fragment thereof described herein is a human kappa light chain or a human lambda light chain. In a particular embodiment, an anti-LGALS3 antibody or an antigen-binding fragment thereof described herein comprises a light chain wherein the amino acid sequence of the variable region of the light chain comprises a VL CDR1, VL CDR2, and VL CDR3 of any one of antibodies listed in FIG. 12 or 13 and wherein the constant region of the light chain is a kappa (κ) or a lambda (λ) light chain constant region. In a particular embodiment, an anti-LGALS3 antibody or an antigen-binding fragment thereof described herein comprises a light chain wherein the amino acid sequence of the variable region of the light chain comprises a VL CDR1, VL CDR2, and VL CDR3 having the amino acid sequences of antibody SEQ ID NO: 8, SEQ ID NO: 9, and SEQ ID NO: 10, respectively, and wherein the constant region of the light chain is a kappa or lambda light chain constant region. In a specific embodiment, an anti-LGALS3 antibody or an antigen-binding fragment thereof described herein comprises a light chain wherein the amino acid sequence of the variable region of the light chain comprises the amino acid sequence of SEQ ID NO: 26, and wherein the constant region of the light chain is a kappa or lambda light chain constant region.

In a specific embodiment, an anti-LGALS3 antibody or antigen-binding fragment thereof described herein comprises a heavy chain variable region (VH) and a light chain variable region (VL) as described herein, and wherein the constant regions are of the type found in an IgG, IgE, IgM, IgD, IgA or IgY immunoglobulin molecule, or a human IgG, IgE, IgM, IgD, IgA or IgY immunoglobulin molecule. In another specific embodiment, an anti-LGALS3 antibody or antigen-binding fragment thereof described herein comprises a VH and a VL comprising any amino acid sequences described herein, and wherein the constant regions are of the type found in an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. In a particular embodiment, the constant regions are of the type found in a human IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2) of immunoglobulin molecule.

In certain embodiments, the epitope of an antibody can be determined by, e.g., NMR spectroscopy, X-ray diffraction crystallography studies, ELISA assays, hydrogen/deuterium exchange coupled with mass spectrometry (e.g., MALDI mass spectrometry), array-based oligo-peptide scanning assays, and/or mutagenesis mapping (e.g., site-directed mutagenesis mapping). For X-ray crystallography, crystallization can be accomplished using any of the known methods in the art (e.g., Giege R et al. (1994) *Acta Crystallogr D Biol Crystallogr* 50(Pt 4): 339-350; McPherson A (1990) *Eur J Biochem* 189: 1-23; Chayen N E (1997) *Structure* 5: 1269-1274; McPherson A (1976) *J Biol Chem* 251: 6300-6303). Antibody: antigen crystals can be studied using well known X-ray diffraction techniques and can be refined using computer software such as X-PLOR (Yale University, 1992, distributed by Molecular Simulations, Inc.; see e.g., Meth Enzymol (1985) volumes 114 & 115, eds Wyckoff H W et al.; U.S. Patent Application No. 2004/0014194), and BUSTER (Bricogne G (1993) *Acta Crystallogr D Biol Crystallogr* 49(Pt 1): 37-60; Bricogne G (1997) *Meth Enzymol* 276A: 361-423, ed Carter C W; Roversi P et al. (2000) *Acta Crystallogr D Biol Crystallogr* 56(Pt 10): 1316-1323). Mutagenesis mapping studies can be accomplished using any method known to one of skill in the art. See, e.g., Champe M et al. (1995) and Cunningham B C & Wells J A (1989) for a description of mutagenesis techniques, including alanine scanning mutagenesis techniques. In addition, antibodies that recognize and bind to the same or overlapping epitopes can be identified using routine techniques such as an immunoassay, e.g., by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits immunospecific binding of a reference antibody to a common antigen. Numerous types of competitive binding assays are known, e.g.: solid phase direct or indirect radioimmunoassay (MA), solid phase direct or indirect enzyme immunoassay (EIA), sandwich competition assay (see Stahli C et al. (1983) *Methods Enzymol* 9: 242-253); solid phase direct biotin-avidin EIA (see Kirkland T N et al. (1986) *J Immunol* 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using 1-125 label (see Morel G A et al. (1988) *Mot Immunol* 25(1): 7-15); solid phase direct biotin-avidin EIA (Cheung R C et al. (1990) *Virology* 176: 546-52); and direct labeled RIA. (Moldenhauer G et al. (1990) *Scand J Immunol* 32: 77-82). Typically, such an assay involves the use of purified antigen bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit immunospecific binding of a reference antibody to a common antigen by at least 50-55%, 55-60%, 60-65%, 65-70%) 70-75%) or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details, see, e.g., Wagener C et al. (1983) *J Immunol* 130: 2308-2315; Wagener C et al. (1984) *J Immunol Methods* 68: 269-274; Kuroki M et al. (1990) *Cancer Res* 50: 4872-4879; Kuroki M et al. (1992) *Immunol Invest* 21: 523-538; Kuroki M et al. (1992) *Hybridoma* 11: 391-407 and Antibodies: A Laboratory Manual, Ed Harlow E & Lane D editors supra, 386-389.

In certain aspects, competition binding assays can be used to determine whether an antibody is competitively blocked, e.g., in a dose dependent manner, by another antibody e.g., an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody can be tested in competition binding assays with an anti-LGALS3 antibody or antigen binding fragment thereof described herein (e.g., a murine IgG antibody containing the variable region of 14D11).

In another aspect, provided herein are antibodies that compete (e.g., in a dose dependent manner) for binding to LGALS3 with an anti-LGALS3 antibody or antigen binding fragment thereof described herein (e.g., a murine IgG antibody containing the variable region of 14D11), as determined using assays known to one of skill in the art or described herein (e.g., ELISA). In another aspect, provided herein are antibodies that competitively inhibit (e.g., in a dose dependent manner) an anti-LGALS3 antibody or antigen binding fragment thereof described herein (e.g., a murine IgG antibody containing the variable region of 14D11) from binding to LGALS3, as determined using assays known to one of skill in the art or described herein (e.g., ELISA).

In certain embodiments, provided herein is an antibody that competes with an antibody described herein for binding to the same extent that an anti-LGALS3 antibody or antigen binding fragment thereof described herein self-competes for binding to LGALS3. In certain embodiments, provided herein is a first antibody that competes with an anti-LGALS3 antibody or antigen binding fragment thereof described herein for binding to LGALS3, wherein the competition is exhibited as reduced binding of the first antibody to the epitope by more than 80% (e.g., 85%, 90%, 95%, or 98%, or between 80% to 85%, 80% to 90%, 85% to 90%, or 85% to 95%). In specific aspects, provided herein is an anti-LGALS3 antibody or antigen binding fragment thereof which competes (e.g., in a dose dependent manner) for immunospecific binding to LGALS3, with an anti-LGALS3 antibody or antigen binding fragment thereof comprising a VH comprising a VH CDR1, a VH CDR2, and/or a VH CDR3 comprising amino acid sequences as described in FIG. 12 or 13 and/or a VL comprising a VL CDR1, a VL CDR2, and/or a VL CDR3 comprising amino acid sequences as described in FIG. 12 or 13. In specific aspects, provided herein is an anti-LGALS3 antibody or antigen binding fragment thereof which competes (e.g., in a dose dependent manner) for immunospecific binding to LGALS3, with an anti-LGALS3 antibody or antigen binding fragment thereof comprising a VH domain having an amino acid sequence as described in FIG. 12*a* and/or a VL as described in FIG. 12*b*.

In specific aspects, provided herein is an anti-LGALS3 antibody or antigen binding fragment thereof which binds to the same or an overlapping epitope of antibody comprising a VH comprising a VH CDR1, a VH CDR2, and/or a VH CDR3 comprising amino acid sequences as described in FIG. 12 or 13 and/or a VL comprising a VL CDR1, a VL CDR2, and/or a VL CDR3 comprising amino acid sequences as described in FIG. 12 or 13. In specific aspects, provided herein is an anti-LGALS3 antibody or antigen binding fragment thereof that binds to the same or an overlapping epitope of antibody comprising a VH domain having an amino acid sequence as described in FIG. 12a and/or a VL as described in FIG. 12b.

Assays known to one of skill in the art or described herein (e.g., X-ray crystallography, ELISA assays, surface plasmon resonance (SPR) assays) can be used to determine if two antibodies bind to the same epitope. Affinity can be measured and/or expressed in a number of ways known in the art, including, but not limited to, equilibrium dissociation constant (KD), and equilibrium association constant (KA). The KD can be determined by techniques known to one of ordinary skill in the art, such as biolayer interferometry.

In certain embodiments, the epitope to which the an anti-LGALS3 antibody or antigen binding fragment thereof described herein binds is used as an immunogen to produce antibodies. In some embodiments, comprises all or a portion of the carbohydrate binding domain of LGALS3.

Functional Characteristics of Anti-LGALS3 Antibodies

In certain embodiments, an anti-LGALS3 antibody or an antigen-binding fragment thereof described herein binds to LGALS3 with a $k_d$ of less than or about $0.5\times10^{-3}$/s, $1\times10^{-3}$/s, $1.5\times10^{-3}$/s, $2\times10^{-3}$/s, $2.5\times10^{-3}$/s, $3\times10^{-3}$7s, $4\times10^{-3}$/s, $5\times10^{-3}$/s, $6\times10^{-3}$/s, $7\times10^{-3}$/s, $8\times10^{-3}$/s, $9\times10^{-3}$/s, $1\times10^{4}$/s, $2\times10^{-4}$/s, $3\times10^{-4}$/s, $4\times10^{-4}$/s, $5\times10^{-4}$/s, $6\times10^{-4}$/s, $7\times10^{-4}$/s, or $8\times10^{-4}$/s. In some embodiments, an anti-LGALS3 antibody or an antigen-binding fragment thereof described herein binds to LGALS3 with a kd of about $0.5\times10^{-3}$/s to $8\times10^{-4}$/s.

In certain embodiments, an anti-LGALS3 antibody or an antigen-binding fragment thereof described herein binds to LGALS3 with a ka of at least or about $2.5\times10^{4}$/s, $3\times10^{4}$/s, $3.5\times10^{4}$/s, $4\times10^{4}$/s, $4.5\times10^{4}$/s, $5\times10^{4}$/s, $5.5\times10^{4}$/s, $6\times10^{4}$/s, $6.5\times10^{4}$/s, $7\times10^{4}$/s, $7\ 0.5\times10^{4}$/s, $8\times10^{4}$/s, $9\times10^{4}$/s, or $9\times10^{5}$/s. In certain embodiments, an anti-LGALS3 antibody or an antigen-binding fragment thereof described herein binds to LGALS3 with a ka of at least or about $2.5\times10^{4}$/s to $9\times10^{5}$/s.

In certain embodiments, an anti-LGALS3 antibody or an antigen-binding fragment thereof described herein binds to LGALS3 with a KD of less than or about 1000 nM, 500 nM, 100 nM, 50 nM, 25 nM, 20 nM, 15 nM, 10 nM, 5 nM, 4 nM, 3 nM, 2 nM, 1 nM, 0.5 nM, 0.1 nM, or 0.05 nM. In some embodiments, an anti-LGALS3 antibody or an antigen-binding fragment thereof described herein binds to LGALS3 with a KD of about 10 nM to about 1000 nM. In some embodiments, an anti-LGALS3 antibody or an antigen-binding fragment thereof described herein binds LGALS3 with a KD of about 100 nM to about 1000 nM. In some embodiments, an anti-LGALS3 antibody or an antigen-binding fragment thereof described herein binds LGALS3 with a KD of about 500 nM to about 1000 nM.

In certain embodiments, the anti-LGALS3 antibody or antigen-binding fragment thereof provided herein binds to LGALS3 at least 10, 20, 30, 40, 50, 60, 70, 80, 90, 100, 250, 500, or 1000 fold more than an isotype control antibody binds to LGALS3. An isotype control antibody is an art-recognized term the refers to an antibody that lacks specificity to the target, but match the class and type of the primary antibody (e.g., an anti-LGALS3 antibody or antigen-binding fragment thereof provided herein). Isotype controls are used as negative controls to help differentiate non-specific background signal from specific antibody signal.

In certain embodiments, an anti-LGALS3 antibody or antigen-binding fragment thereof described herein binds to LGALS3 with a 100-1,000 fold increased affinity over the natural ligand binding.

Assays to determine the anti-LGALS3 antibody- or antigen-binding fragment-mediated inhibition of Matrigel invasion are known to a person skilled in the art. For example, BD BioCoat™ Matrigel™ Invasion Inserts or Chambers (catalog #354480 in 24 well plate) and Control Inserts (catalog #354578 in 24 well plate) can be purchased from BD Biosciences, MA. Matrigel Invasion assay can be performed as per manufacturer's protocol. Briefly, the Matrigel chambers in 24 well plates (stored at −20° C.) and control inserts (stored at 4° C.) are allowed to come to room temperature. Both inserts are rehydrated with 0.5 mL of serum free medium in the insert as well as in the outside well of the 24 well plate, for 2 hrs at 37° C. 5% $CO_2$ humidified incubator. Cultured SKOV3 cells are trypsinized and washed with culture medium. A million cells are separated into another centrifuge tube and washed 3 times with serum free medium. These cells are later adjusted to give 5,000 cells in 0.5 mL serum free medium. The medium in the rehydrated inserts are removed and the insert was transferred into a new 24 well plate containing 0.75 mL of 10% Fetal Bovine Serum (FBS) containing culture medium in the well which serves as a chemo attractant. Immediately, 0.5 mL of the cells (5,000 cells) in serum free medium is added to the insert. Proper care is taken to see that there is no air bubble is trapped in the insert and the outside well. The 24 well plate is incubated at 37° C. 5% $CO_2$ humidified incubator for 48 hrs. After incubation, the non-invading cells are removed from the upper surface of the membrane by "scrubbing" by inserting a cotton tipped swab into Matrigel or control insert and gently applied pressure while moving the tip of the swab over the membrane surface. The scrubbing is repeated with a second swab moistened with medium. Then the inserts are stained in a new 24 well plate containing 0.5 mL of 0.5% crystal violet stain in distilled water for 30 minutes. Following staining the inserts are rinsed in 3 beakers of distilled water to remove excess stain. The inserts are air dried for in a new 24 well plate. The invaded cells are hand counted under an inverted microscope at 200× magnification. Several fields of triplicate membranes were counted and recorded in the figure.

In certain embodiments, an anti-LGALS3 antibody or an antigen-binding fragment thereof described herein is capable of inhibiting or reducing metastasis, inhibiting tumor growth or inducing tumor regression in mouse model studies. For example, tumor cell lines can be introduced into athymic nude mice, and the athymic mice can be administered anti-LGALS3 antibodies described herein one or more times, and tumor progression of the injected tumor cells can be monitored over a period of weeks and/or months. In some cases, administration of the anti-LGALS3 antibodies or antigen-binding fragments thereof to the athymic nude mice can occur prior to introduction of the tumor cell lines. In a certain embodiment, SKOV3 cells are utilized for the mouse xenograft models described herein.

In specific embodiments, anti-LGALS3 antibodies or antigen-binding fragments thereof described herein inhibit tumor growth or induce tumor regression in a mouse model by at least about 5%, 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein or known to one of skill in the art, as compared to mock treated mice. In specific embodiments, anti-LGALS3 antibodies or antigen-binding fragments thereof described herein inhibit tumor growth or induce tumor regression in a mouse model by at least about 25% or 35%), optionally to about 75%, as assessed by methods described herein or known to one of skill in the art, as compared to mock-treated mice. In specific embodiments, anti-LGALS3 antibodies or antigen-binding fragments thereof described herein inhibit tumor growth or induce tumor regression in a mouse model by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art, as compared to mock-treated mice. Mock-treated mice can, for example, be treated with phosphate buffered saline or a control (e.g., anti-IgG antibody).

Determining tumor growth inhibition or tumor regression can be assessed, for example, by monitoring tumor size over a period of time, such as by physical measurement of palpable tumors, or other visual detection methods. For example, tumor cell lines can be generated to recombinantly express a visualization agent, such as green fluorescent protein (GFP) or luciferase, then in vivo visualization of GFP can be carried out by microscopy, and in vivo visualization of luciferase can be carried out by administering luciferase substrate to the xenograft mice and detecting luminescent due to the luciferase enzyme processing the luciferase substrate. The degree or level of detection of GFP or luciferase correlates to the size of the tumor in the xenograft mice.

In certain embodiments, anti-LGALS3 antibodies or antigen-binding fragments thereof described herein can increase survival of animals in tumor xenograft models as compared to mock-treated mice. In specific embodiments, anti-LGALS3 antibodies or antigen-binding fragments thereof described herein increase survival of mice in tumor xenograft models by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, as compared to mock-treated mice. In specific embodiments, anti-LGALS3 antibodies or antigen-binding fragments thereof described herein increase survival of mice in tumor xenograft models by at least about 25% or 35%, optionally to about 75%), as assessed by methods described herein or known to one of skill in the art, as compared to mock-treated mice in tumor xenograft models. In specific embodiments, anti-LGALS3 antibodies or antigen-binding fragments thereof described herein increase survival of mice in tumor xenograft models by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art, as compared to mock-treated mice in tumor xenograft models. Survival can, for example, be determined by plotting a survival curve of number of surviving mice against time (e.g., days or weeks) after tumor cell line injection. Mock-treated mice can, for example, be treated with phosphate buffered saline or a control (e.g., anti-IgG antibody).

Antibody Conjugates

In some embodiments, an anti-LGALS3 antibody or antigen-binding fragment thereof provided herein is conjugated to another molecule, such as an organic moiety, a detectable label, and/or an isotope.

In certain embodiments, provided herein are anti-LGALS3 antibodies or antigen-binding fragment thereof conjugates, wherein said anti-LGALS3 antibody or antigen-binding fragment thereof is conjugated to one or more agents, e.g., an imaging agent or a cytotoxic agent. Also provided herein are bispecific antibody conjugates, wherein said bispecific antibody is conjugated to one or more agent, e.g., an imaging agent or a cytotoxic agent. Also provided herein are antibody heavy chain conjugates, wherein said antibody heavy chain is conjugated to one or more agent, e.g., an imaging agent or a cytotoxic agent. Also provided herein are antibody light chain conjugates, wherein said antibody light chain is conjugated to one or more agent, e.g., an imaging agent or a cytotoxic agent. Also provided herein are fusion protein conjugates, wherein said fusion protein is conjugated to an agent, e.g., an imaging agent or a cytotoxic agent. In certain embodiments, the agent is conjugated covalently or non-covalently. In certain embodiments, the imaging agent is a detectable label, such as, a chromogenic, enzymatic, radioisotopic, isotopic, fluorescent, toxic, chemiluminescent, nuclear magnetic resonance contrast agent or other label.

Non-limiting examples of suitable chromogenic labels include diaminobenzidine and 4-hydroxyazo-benzene-2-carboxylic acid.

Non-limiting examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Non-limiting examples of suitable radioisotopic labels include $^{3}H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{217}Pb$, $^{47}Sc$, $^{223}Ra$, $^{224}Ra$, $^{89}Zr$, $^{177}Lu$, and $^{109}Pd$. In certain embodiments, $^{111}In$ is used for in vivo imaging as it avoids the problem of dehalogenation of $^{125}I$ or $^{131}I$-labeled anti-LGALS3 antibodies or antigen-binding fragments thereof in the liver. In addition, $^{111}In$ has a more favorable gamma emission energy for imaging (Perkins et al. (1985) Eur. J. Nucl. Med. 70:296-301; Carasquillo et ah, (1987) J. Nucl. Med. 25:281-287). For example, $^{111}In$ coupled to monoclonal antibodies with 1-(P-isothiocyanatobenzyl)-DPTA has shown little uptake in non-tumorous tissues, particularly the liver, and therefore enhances specificity of tumor localization (Esteban et al., (1987) J. Nucl. Med. 28:861-870).

Non-limiting examples of suitable non-radioactive isotopic labels include $^{157}Gd$, $^{55}Mn$, $^{162}Dy$, $^{52}Tr$, and $^{56}Fe$.

Non-limiting examples of suitable fluorescent labels include a $^{152}Eu$ label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label.

Non-limiting examples of chemiluminescent labels include a luminol label, an isoluminol label, an aromatic acridinium ester label, an imidazole label, an acridinium salt label, an oxalate ester label, a luciferin label, a luciferase label, and an aequorin label.

Non-limiting examples of nuclear magnetic resonance contrasting agents include heavy metal nuclei such as Gd, Mn, and iron.

Techniques known to one of ordinary skill in the art for conjugating the above-described labels to said anti-LGALS3 antibodies or antigen-binding fragments thereof, bispecific antibodies, antibody heavy chains, antibody light chains, and fusion proteins are described in, for example, Kennedy et al. (1976) Clin. Chm. Acta 70: 1-31, and Schurs et al. (1977) Clin. Chm. Acta 81: 1-40. Coupling techniques mentioned in the latter are the glutaraldehyde method, the periodate method, the dimaleimide method, the m-maleimidobenzoyl-N-hydroxy-succinimide ester method, all of which methods are incorporated by reference herein.

Non-limiting examples of cytotoxic agents include a cytostatic or cytocidal agent, a radioactive metal ion, e.g., alpha-emitters, and toxins, e.g., pseudomonas exotoxin, abrin, cholera toxin, ricin A, and diphtheria toxin.

In certain embodiments, the agent is a diagnostic agent. A diagnostic agent is an agent useful in diagnosing or detecting a disease by locating the cells containing the antigen. Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. In some embodiments, the diagnostic agents are selected from the group consisting of radioisotopes, enhancing agents for use in magnetic resonance imaging, and fluorescent compounds. In order to load an anti-LGALS3 antibody or antigen-binding fragment thereof with radioactive metals or paramagnetic ions, it can be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, for example, ethylenediaminetetraacetic acid (EDTA), diethylenetriaminepentaacetic acid (DTPA), porphyrins, polyamines, crown ethers, bis-thiosemicarbazone, polyoximes, and like groups known to be useful for this purpose. Chelates are coupled to the antibodies using standard chemistries. The chelate is normally linked to the antibody by a group which enables formation of a bond to the molecule with minimal loss of immunoreactivity and minimal aggregation and/or internal cross-linking other, more unusual, methods and reagents for conjugating chelates to antibodies are disclosed in U.S. Pat. No. 4,824,659 to Hawthorne, entitled "Antibody Conjugates," issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MRI, when used along with an anti-LGALS3 antibody or antigen-binding fragment thereof provided herein. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as 223Ra for RAIT are encompassed herein.

In certain embodiments, the agent is an organic agent. Such organic agents can produce a conjugate with improved pharmacokinetic properties (e.g., increased in vivo serum half-life). The organic moiety can be a hydrophilic polymeric group, fatty acid group, or fatty acid ester group. As used herein, the term "fatty acid" encompasses monocarboxylic acids and di-carboxylic acids. As used herein, a "hydrophilic polymeric group" refers to an organic polymer that is more soluble in water than in octane, e.g., polylysine. Hydrophilic polymers suitable for modifying an anti-LGALS3 antibody or antigen-binding fragment thereof provided herein can be linear or branched and include, for example, polyalkane glycols (e.g., polyethylene glycol, (PEG), monomethoxy-polyethylene glycol, and polypropylene glycol), carbohydrates (e.g., dextran, cellulose, oligosaccharides, and polysaccharides), polymers of hydrophilic amino acids (e.g., polylysine, polyarginine, and polyaspartate), polyalkane oxides (e.g., polyethylene oxide and polypropylene oxide) and polyvinyl pyrolidone. In certain embodiments, the hydrophilic polymer that modifies an anti-LGALS3 antibody or antigen-binding fragment thereof, a bispecific antibody, an antibody heavy chain, an antibody light chain, or a fusion protein provided herein has a molecular weight of about 800 to about 150,000 Daltons as a separate molecular entity. For example, $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying an anti-LGALS3 antibody or antigen-binding fragment thereof, a bispecific antibody, an antibody heavy chain, an antibody light chain, or a fusion protein provided herein can be saturated or can contain one or more units of unsaturation. Fatty acids that are suitable for modifying an anti-LGALS3 antibody or antigen-binding fragment thereof, a bispecific antibody, an antibody heavy chain, an antibody light chain, or a fusion protein provided herein include, for example, n-dodecanoate, n-tetradecanoate, n-octadecanoate, n-eicosanoate, n-docosanoate, n-triacontanoate, n-tetracontanoate, cis-delta-9-octadecanoate, all cis-delta-5,8,11,14-eicosatetraenoate, octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The conjugates provided herein can be prepared using suitable methods, such as by reaction with one or more modifying agents. As used herein, an "activating group" is a chemical moiety or functional group that can, under appropriate conditions, react with a second chemical group thereby forming a covalent bond between the modifying agent and the second chemical group. For example, amine-reactive activating groups include electrophilic groups such as, for example, tosylate, mesylate, halo (chloro, bromo, fluoro, iodo), N-hydroxysuccinimidyl esters (NETS), and the like. Activating groups that can react with thiols include, for example, maleimide, iodoacetyl, acryloyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphoramide linkages. Suitable methods to introduce activating groups into molecules are known in the art (see, for example, Hernanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example a divalent $C_1$-$C_{12}$ group, wherein one or more carbon atoms can be replaced by a heteroatom such as oxygen, nitrogen or sulfur. Suitable linker moieties include, for example, tetraethylene glycol, $(CH_2)_3$, and NH. Modifying agents that comprise a linker moiety can be produced, for example, by reacting a mono-Boc-alkyldiamine (e.g., mono-Boc-ethylenediamine or mono-Boc-diaminohexane) with a fatty acid in the presence of 1-ethyl-3-(3-dimethylaminopropyl)carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

A "modifying agent" can refer to a suitable organic group (e.g., hydrophilic polymer, a fatty acid, and a fatty acid ester) that comprises an activating group. For example, the organic moieties can be bonded to the anti-LGALS3 antibody or antigen-binding fragment thereof in a non-site specific manner by employing an amine-reactive modifying agent, for example, an N-hydroxysuccinimide ester of PEG. A modified the anti-LGALS3 antibody or antigen-binding fragment thereof can also be prepared by reducing disulfide bonds (e.g., intra-chain disulfide bonds) of the anti-LGALS3 antibody or antigen-binding fragment thereof, bispecific antibody, antibody heavy chain, antibody light chain, or fusion protein. The reduced anti-LGALS3 antibody or antigen-binding fragment thereof, bispecific antibody, antibody heavy chain, antibody light chain, or fusion protein can then be reacted with a thiol-reactive modifying agent to produce the conjugates provided herein. Conjugates comprising an organic moiety that is bonded to specific sites of an anti-LGALS3 antibody or antigen-binding fragment thereof provided herein can be prepared using suitable methods, such as reverse proteolysis (Fisch et al. (1992) *Bioconjugate Chem.,* 3: 147-153; Werlen et al. (1994) *Bioconjugate Chem.,* 5:411-417; Kumaran et al. (1997) *Protein Sci.* 6(10):2233-2241; Itoh et al. (1996) *Bioorg. Chem.,* 24(1): 59-68; Capellas et al. (1997) *Biotechnol. Bioeng.* 56(4):456-463), and the methods described in Hermanson, G. T., Bioconjugate Techniques, Academic Press: San Diego, Calif. (1996).

Antibody Production

Producing and Screening Antibodies

In another aspect, provided herein are methods of producing anti-LGALS3 antibodies or antigen-binding fragments. The antibodies or antigen-binding fragments thereof described herein can be produced by any method known in the art for the synthesis of antibodies, e.g., by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, e.g., in the references cited herein and are fully explained in the literature. See, e.g., Maniatis T et al. (1982) Molecular Cloning: A Laboratory Manual, Cold Spring Harbor Laboratory Press; Sambrook J et al. (1989), Molecular Cloning: A Laboratory Manual, Second Edition, Cold Spring Harbor Laboratory Press; Sambrook J et al. (2001) Molecular Cloning: A Laboratory Manual, Cold Spring Harbor Laboratory Press, Cold Spring Harbor, NY; Ausubel F M et al. Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al. (eds.) (1999) Genome Analysis: A Laboratory Manual, Cold Spring Harbor Laboratory Press.

In a specific embodiment, an anti-LGALS3 antibody or antigen binding fragment thereof described herein is an antibody (e.g., recombinant antibody) prepared, expressed, created or isolated by any means that involves creation, e.g., via synthesis, genetic engineering of DNA sequences. In certain embodiments, such antibody comprises sequences that are encoded by DNA sequences that do not naturally exist within the antibody germline repertoire of an animal or mammal (e.g., human) in vivo. In a specific embodiment, an anti-LGALS3 antibody or antigen binding fragment thereof described herein is made by a method comprising using the carbohydrate binding domain of LGALS3 or a portion thereof. See, e.g., Example 3 for a detailed description of an exemplary method for how to produce antibodies described herein.

In a certain aspect, provided herein is an immunogenic peptide comprising (SEQ ID NO: 2)
CNTKLDNNWGREERQSVFPFESG.

In a certain aspect, provided herein is an immunogenic peptide comprising a Fc-fusion protein comprising amino acids 117-224 of LGALS3 linked to the Fc region (CH2 and CH3 domains) of the human IgG1 heavy chain and the hinge region. Amino acids 117-224 of LGALS3 is represented by the following amino acid sequence:

(SEQ ID NO: 27)
PYNLPLPGGVVPRMLITILGTVKPNANRIALDFQRGNDVAFHFNPRFNEN

NRRVIVCNTKLDNNWGREERQSVFPFESGKPFKIQVLVEPDHFKVAVNDA

HLLQYNHRVKKLNEISKLGISGDIDLTS.

In some embodiment amino acids 117-224 of LGALS3 can be encoded by the following exemplary nucleotide sequence:

(SEQ ID NO: 28)
CCTTATAACCTGCCTTTGCCTGGGGGAGTGGTGCCTCGCATGCTGATAAC

AATTCTGGGCACGGTGAAGCCCAATGCAAACAGAATTGCTTTAGATTTCC

AAAGAGGGAATGATGTTGCCTTCCACTTTAACCCACGCTTCAATGAGAAC

AACAGGAGAGTCATTGTTTGCAATACAAAGCTGGATAATAACTGGGGAAG

GGAAGAAAGACAGTCGGTTTTCCCATTTGAAAGTGGGAAACCATTCAAAA

TACAAGTACTGGTTGAACCTGACCACTTCAAGGTTGCAGTGAATGATGCT

CACTTGTTGCAGTACAATCATCGGGTTAAAAAACTCAATGAAATCAGCAA

ACTGGGAATTTCTGGTGACATAGACCTCACCAGT.

In certain embodiments, the immunogenic peptide is conjugated to an immunogenic carrier protein. In most cases, small antigens (e.g., short peptides or small haptens) are not sufficiently complex to elicit the production of antibodies. The immunogenic carrier proteins, because of their large size and complex structure, may confer immunogenicity to conjugated small antigens, resulting in antibodies being produced against epitopes on the small antigens and the immunogenic carrier proteins. Therefore, small antigens are always chemically conjugated with immunogenic carrier proteins to intensify the immune response for successful production of antibodies. Commonly used immunogenic carrier proteins include, but are not limited to, keyhole limpet hemocyanin (KLH), *Concholepas concholepas* hemocyanin (CCH), bovine serum albumin (BSA), and ovalbumin (OVA). In a specific embodiment, the immunogenic peptide is conjugated to KLH. KLH is a copper-containing polypeptide that belongs to a group of non-heme proteins called hemocyanins, which are found in arthropods and mollusks. KLH is isolated from keyhole limpets (*Megathura crenulata*). Because of its evolutionary distance from mammals, high molecular weight, complex structure, and a large surface containing several hundred lysine groups that provide primary amines as targets for conjugation, KLH is an extremely immunogenic and effective carrier protein in mammals.

In certain embodiments, the immunogenic peptide is 10 to 60 amino acid residues in length. In some embodiments, the immunogenic peptide is 10 to 30 amino acid residues in length. In some embodiments, the immunogenic peptide is 15 to 25 amino acid residues in length. In some embodiments, the immunogenic peptide is 15 to 20 amino acid residues in length. In specific embodiments, the immunogenic peptide is 15 to 18 amino acid residues in length.

In certain embodiments, the immunogenic peptide comprises an at least 10 amino acid portion of the LGALS3 CBD domain. In certain embodiments, the immunogenic peptide comprises an at least 10 amino acid portion of the amino acid sequence of SEQ ID NO: 27. In certain other embodiments, the immunogenic peptide comprises an at least 15, 20, 25, or 30 amino acid portion of the amino acid sequence of SEQ ID NO: 27. In specific embodiments, the immunogenic peptide consists of 15 to 30 consecutive amino acid residues of SEQ ID NO: 27.

In another aspect, provided herein is a method of generating an antibody or an antigen-binding fragment thereof that immunospecifically binds to a LGALS3, comprising immunizing a subject with an immunogenic peptide as described above. The subject immunized in accordance with the methods described herein can be, but is not limited to, a goat, a sheep, a donkey, a chicken, a guinea pig, a rat, a rabbit, or a mouse. In some embodiments, the subject immunized in accordance with the methods described herein is a rat, a rabbit, or a mouse. In a specific embodiment, the subject immunized in accordance with the methods described herein is a mouse. In some embodiments, the subject immunized in accordance with the methods described herein is a transgenic mouse that expresses chimeric forms of various immunoglobulin chains. In some embodiments, the transgenic mouse expresses human variable region linked to a mouse constant region. (See e.g. U.S. Pat. Nos. 8,502,018, 9,580,491, US Patent Publication Nos. 20170218090, 20160222093, and 20130167256, each of which is incorporated by reference in its entirety; see also AlivaMab Mouse platform (Ablexis)).

Immunization of the subject can be performed by any method known in the art, for example, by administering the immunogenic peptide and an adjuvant to the subject as described in Example 3.

In another aspect, also provided herein is a method of preparing an immunogenic peptide described herein. In certain embodiments, the method of preparing the immunogenic peptide comprises synthesizing the peptide moiety. The peptide moiety of the immunogenic peptide can be synthesized by any method known in the art, for example, by Fmoc solid-phase peptide synthesis.

Methods to produce anti-LGALS3 antibodies or antigen-binding fragments thereof described herein are known to one of ordinary skill in the art, for example, by chemical synthesis, by purification from biological sources, or by recombinant expression techniques, including, for example, from mammalian cell or transgenic preparations. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, for example, Maniatis et al. (1982) Molecular Cloning: A Laboratory Manual, Cold Spring Harbor Laboratory Press; Sambrook et al. (1989), Molecular Cloning: A Laboratory Manual, Second Edition, Cold Spring Harbor Laboratory Press; Sambrook et al. (2001) Molecular Cloning: A Laboratory Manual, Cold Spring Harbor Laboratory Press, Cold Spring Harbor, NY; Ausubel et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren et al. (eds.) (1999) Genome Analysis: A Laboratory Manual, Cold Spring Harbor Laboratory Press.

A variety of methods exist in the art for the production of anti-LGALS3 antibodies or antigen-binding fragments thereof described herein. For example, the anti-LGALS3 antibody or antigen-binding fragment thereof can be made by recombinant DNA methods, such as those described in U.S. Pat. No. 4,816,567. The one or more DNAs encoding an anti-LGALS3 antibody or antigen-binding fragment thereof provided herein can be readily isolated and sequenced using conventional procedures (e.g., by using oligonucleotide probes that are capable of binding specifically to genes encoding the heavy and light chains of murine antibodies, or such chains from human, humanized, or other sources). Once isolated, the DNA can be placed into expression vectors, which are then transformed into host cells such as NSO cells, Simian COS cells, Chinese hamster ovary (CHO) cells, yeast cells, algae cells, eggs, or myeloma cells that do not otherwise produce immunoglobulin protein, to obtain the synthesis of the anti-LGALS3 antibody or antigen-binding fragment thereof in the recombinant host cells. The DNA also can be modified, for example, by substituting the coding sequence for human heavy and light chain constant domains of a desired species in place of the homologous human sequences (U.S. Pat. No. 4,816,567; Morrison et al. supra) or by covalently joining to the immunoglobulin coding sequence all or part of the coding sequence for a non-immunoglobulin polypeptide. Such a non-immunoglobulin polypeptide can be substituted for the constant domains of an anti-LGALS3 antibody or antigen-binding fragment thereof provided herein. In certain embodiments, the DNA encoding anti-LGALS3 antibodies or antigen-binding fragments thereof provided herein can also be prepared using at least one anti-LGALS3 antibody- or antigen-binding fragment thereof-encoding polynucleotide to provide transgenic animals or mammals, such as goats, cows, horses, sheep, and the like, that produce such antibodies in their milk. Such animals can be provided using known methods. See, for example, but not limited to, U.S. Pat. Nos. 5,827,690; 5,849,992; 4,873,316; 5,849,992; 5,994,616, 5,565,362; 5,304,489, and the like, each of which is entirely incorporated herein by reference.

In certain embodiments, anti-LGALS3 antibodies or antigen-binding fragments thereof provided herein can additionally be prepared using at least one anti-LGALS3 antibody- or antigen-binding fragment thereof-encoding polynucleotide provided herein to provide transgenic plants and cultured plant cells (for example, but not limited to tobacco and maize) that produce such antibodies, specified portions or variants in the plant parts or in cells cultured there from. As a non-limiting example, transgenic tobacco leaves expressing recombinant proteins have been successfully used to provide large amounts of recombinant proteins, for example, using an inducible promoter. See, for example, Cramer et al. (1999) Curr. Top. Microbol. Immunol. 240: 95-118 (1999) and references cited therein. Also, transgenic maize has been used to express mammalian proteins at commercial production levels, with biological activities equivalent to those produced in other recombinant systems or purified from natural sources. See, for example, Hood et al. (1999) Adv. Exp. Med. Biol. 464: 127-147 and references cited therein. Antibodies have also been produced in large amounts from transgenic plant seeds including antibody fragments, such as scFvs, including tobacco seeds and potato tubers. See, for example, Conrad et al. (1998) Plant Mol. Biol. 38: 101-109 and references cited therein. Thus, anti-LGALS3 antibodies or antigen-binding fragments thereof can also be produced using transgenic plants, according to known methods. See also, for example, Fischer et al. (1999) Biotechnol. Appl. Biochem. 30:99-108, Ma et al. (1995) Trends Biotechnol. 13:522-7; Ma et al, (1995) Plant Physiol. 109:341-6; Whitelam et al. (1994) Biochem Soc. Trans. 22:940-944; and references cited therein. Each of the above references is entirely incorporated herein by reference.

In certain embodiments, anti-LGALS3 antibodies or antigen-binding fragments thereof provided herein can be prepared using at least one anti-LGALS3 antibody- or antigen-binding fragment thereof-encoding polynucleotide provided herein to provide bacteria that produce such anti-LGALS3 antibodies or antigen-binding fragments. As a non-limiting example, E. coli expressing recombinant proteins has been successfully used to provide large amounts of recombinant proteins. See, for example, Verma et al. (1998) 216(1-2): 165-181 and references cited therein.

Methods for making multispecific (e.g., bispecific antibodies) have been described, see, e.g., U.S. Pat. Nos. 7,951, 917; 7, 183,076; 8,227,577; 5,837,242; 5,989,830; 5,869, 620; 6,132,992 and 8,586,713.

In certain embodiments, anti-LGALS3 antibodies or antigen-binding fragments thereof provided herein are utilized in the generation of bispecific antibodies. Bispecific antibodies can be made by fusing two hybridomas to create hybrid immunoglobulin molecules with two binding sites. Bispecific antibodies not only handcuff tumors to T-cells; they cross-link CD3 on T-cells and initiate the activation cascade. This way, T cell receptor-based cytotoxicity is redirected to desired tumor targets bypassing MHC restrictions. Arming of polyclonally activated T cells (ATC) with an anti-CD3-anti-LGALS3 bispecific binding molecule combines the targeting specificity of the anti-LGALS3 antibody with the non-MHC-restricted perforin/granzyme mediated cytotoxicity of T cells. Bispecific binding molecules BsAb or BiTE can arm ex vivo expanded activated T cells before infusion into a patient. This strategy converts every ATC into a specific CTL (Thakur and Lum (2010) Curr Opin Mol Ther 12, 340-349; Grabert et al. (2006) Clin Cancer Res 12, 569-576).

Bispecific binding molecules can be comprised of an anti-LGALS3 antibody, wherein the anti-LGALS3 antibody is an immunoglobulin, wherein each light chain of the immunoglobulin is a fusion protein, wherein the fusion protein is the immunoglobulin light chain linked via a peptide linker to a scFv targeting CD3. A N297A mutation in the CH2 domain results in a glycosylation leading to no FcR or C1q binding.

An anti-LGALS3 antibody or antigen-binding fragment thereof provided herein can be utilized to generate a CAR. CARs are most commonly composed of a single chain variable fragment length antibody (scFv), such as one derived from a monoclonal antibody targeting a given tumor associated antigen and/or variant thereof, a transmembrane domain (for example, a transmembrane domain derived from a T Cell surface molecule such as a costimulatory molecule such as CD8, CD28, OX-40, and 4-1BB), a signaling portion of a TCR complex, such as an intracellular domain and/or additional portion(s) of a TCR zeta ($\zeta$) chain, such as a cytoplasmic signaling domain thereof.

In a specific embodiment, the heavy and light chain variable regions of a monoclonal anti-LGALS3 antibody described herein are isolated from a hybridoma cell line which generates a monoclonal anti-LGALS3 antibody. For example, RNA is extracted from the hybridoma cell line and cDNA is generated from the RNA by reverse transcription PCR. The VH and VL chain variable regions are cloned by standard PCR utilizing primers specific for such variable regions. The resulting VH and VL fragments are subcloned into a shuttle vector, such as, for example TopoTA PCR 2.1 cloning vector (Invitrogen), and sequenced. The VH and VL fragments are subsequently ligated to a (Gly4Ser)3 spacer domain (SEQ ID NO: 308), generating an anti-LGALS3 antibody scFv and fused to the human CD8 leader peptide (CD8L) (CD8L-anti-LGALS3 antibody scFv) by overlapping PCR (see, e.g., Maher et al. (2002) Nat Biotechnol 20(1):70-5 and Gong et al. (1999) Neoplasia 1(2): 123-7). The coding region of the CD8L-anti-LGALS3 antibody scFv is fused to the human CD8 hinge and transmembrane domains, or alternatively to the CD28 transmembrane and cytoplasmic signaling domains, fused to the T cell receptor 0)3-$\zeta$ signaling domain (see, e.g., Maher et al. (2002) Nat Biotechnol 20(1):70-5; Brentjens et al. (2003) Nat Med 9(3):279-86; and Brentjens et al. (2007) Clin Cancer Res 13(18 Pt1):5426-35).

Also provided herein is a T cell expressing a CAR described herein. Methods for the generation of a T cell expressing a CAR are known in the art. For example, a CAR construct can be sub-cloned into a modified MMLV retroviral vector SFG (see, e.g., Riviere et al. (1995) Proc Natl Acad Sci USA 92(15):6733-7) or other suitable retroviral vectors. In some embodiments, the retroviral vector is a lentiviral vector, for example, an HIV-based vector. VSV-G pseudotyped retroviral supernatants derived from transduced gpg29 fibroblasts can be used to construct stable PG13 gibbon ape leukemia virus (GaLV) envelope-pseudotyped retroviral producing cell lines (see, e.g., Gong et al. (1999) Neoplasia 1(2): 123-7). Isolated healthy donor peripheral blood mononuclear cells (PBMCs) can be activated with phytohemagglutinin (PHA) at 2 µg/ml (Sigma. St. Louis, MO) and retrovirally transduced on retronectin coated non-tissue culture plates (Quintas-Cardama A, et al. (2007) Hum Gene Ther 18(12): 1253-60) to generate the T cell recombinantly expressing the CAR. Gene transfer of the CAR into the T cell can be assessed by FACS.

Single domain antibodies, e.g., antibodies lacking the light chains, can be produced by methods well known in the art. See, e.g., Riechmann and Muyldermans (1999) *J Immunol* 231: 25-38; Nuttall S D et al. (2000) *Curr Pharm Biotechnol* 1(3): 253-263; Muyldermans S, (2001) *J Biotechnol* 74(4): 277-302; U.S. Pat. No. 6,005,079; and International Publication Nos. WO 94/04678, WO 94/25591 and WO 01/44301, each of which are incorporated by reference in their entirety.

In particular embodiments, an anti-LGALS3 antibody or antigen binding fragment thereof described herein, which binds to the same or an overlapping epitope as an anti-LGALS3 antibody described herein, is a human anti-LGALS3 antibody or antigen-binding fragment thereof. In particular embodiments, an anti-LGALS3 antibody or antigen binding fragment thereof described herein, which competitively blocks (e.g., in a dose-dependent manner) any one of the antibodies described herein, from binding to LGALS3, is a human anti-LGALS3 antibody or antigen-binding fragment thereof.

Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see, e.g., Lonberg and Huszar (1995) *Int Rev Immunol* 13:65-93. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mouse™ (Kirin) and the KM Mouse™ (Medarex/Kirin).

Human antibodies which immunospecifically bind to LGALS3 can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen. Such methods are known and are described in the art, see, e.g., Shinmoto H et al. (2004) *Cytotechnology* 46: 19-23; Naganawa Y et al. (2005) *Human Antibodies* 14: 27-31.

Exemplary methods of producing antibodies or antigen-binding fragments thereof that immunospecifically bind to LGALS3 and methods of screening and selecting antibodies or antigen-binding fragments thereof that immunospecifically bind to LGALS3 are described in Example 3. In exemplary embodiments, the mouse-human hybridomas are generated from mice immunize with an immunogenic peptide of LGALS3 or a chimeric fusion protein as described in Example 3. In exemplary embodiments, the monoclonal antibodies secreted by the hybridomas are screened for binding to the LGALS3 carbohydrate binding domain peptide (CBD), full-length LSGAL3 protein. In some embodiments, the LGALS3 N-terminus, which contains the polymerization domain, is employed as a control. In some embodiments, the monoclonal antibodies are further screened against Murine Gal3 CBD (mCBD3) or other members of the galectin family, such as, for example, LGAL1, LGAL7, LGAL8, and LGAL9.

Once an anti-LGALS3 antibody or an antigen-binding fragment thereof described herein has been produced, it can be purified by any method known in the art for purification of an immunoglobulin molecule, e.g., by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an anti-LGALS3 antibody or an antigen-binding fragment thereof described herein is isolated or purified. Generally, an isolated antibody is one that is substantially free of other antibodies with different antigenic specificities than the isolated antibody. For example, in a particular embodiment, a preparation of an anti-LGALS3 antibody or antigen binding fragment thereof described herein is substantially free of cellular material and/or chemical precursors. The language "substantially free of cellular material" includes preparations of an anti-LGALS3 antibody or antigen binding fragment thereof in which the antibody is separated from cellular components of the cells from which it is isolated or recombinantly produced. Thus, an anti-LGALS3 antibody or antigen binding fragment thereof that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an anti-LGALS3 antibody or antigen binding fragment thereof, e.g., different post-translational modified forms of an anti-LGALS3 antibody or antigen binding fragment thereof or other different versions of an anti-LGALS3 antibody or antigen binding fragment thereof (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

Polynucleotides

In certain embodiments, provided herein are polynucleotides comprising a nucleotide sequence encoding an anti-LGALS3 antibody or antigen-binding fragment thereof. Also provided herein are vectors comprising such polynucleotides. Also provided herein are polynucleotides encoding antigens of the anti-LGALS3 antibody or antigen-binding fragment thereof described herein. Also provided herein are polynucleotides that hybridize under stringent or lower stringency hybridization conditions to polynucleotides that encode an anti-LGALS3 antibody or antigen-binding fragment thereof described herein.

The language "purified" includes preparations of polynucleotide or nucleic acid molecule having less than about 15%, 10%, 5%, 2%, 1%, 0.5%, or 0.1% (in particular less than about 10%)) of other material, e.g., cellular material, culture medium, other nucleic acid molecules, chemical precursors and/or other chemicals. In a specific embodiment, a nucleic acid molecule(s) encoding an anti-LGALS3 antibody or antigen-binding fragment thereof described herein is isolated or purified.

Nucleic acid molecules provided herein can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

In certain embodiments, provided herein is a polynucleotide comprising nucleotide sequences encoding anti-LGALS3 antibody or antigen-binding fragment thereof described herein. In particular aspects, also provided herein are polynucleotides comprising nucleotide sequences encoding anti-LGALS3 antibodies or antigen-binding fragments thereof, which immunospecifically bind to LGALS3, and comprise an amino acid sequence as described herein, as well as antibodies which compete with such anti-LGALS3 antibody or antigen-binding fragment thereof for binding to LGALS3, or which binds to the same epitope as that of such antibodies.

The polynucleotides provided herein can be obtained by any method known in the art. For example, if the nucleotide sequence encoding an anti-LGALS3 antibody or antigen-binding fragment thereof described herein is known, a polynucleotide encoding the anti-LGALS3 antibody or antigen-binding fragment thereof can be can be assembled from chemically synthesized oligonucleotides (e.g., as described in Kutmeier et al. (1994) BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an anti-LGALS3 antibody or antigen-binding fragment thereof can be generated from nucleic acid from a suitable source. If a clone containing a nucleic acid encoding a particular anti-LGALS3 antibody or antigen-binding fragment thereof is not available, but the sequence of the anti-LGALS3 antibody or antigen-binding fragment thereof is known, a nucleic acid encoding the anti-LGALS3 antibody or antigen-binding fragment thereof can be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an anti-LGALS3 antibody or antigen binding fragment thereof provided herein) by PCR amplification using synthetic primers that hybridize to the 3' and 5' ends of the sequence or by cloning using an oligonucleotide probe specific for the particular gene sequence to identify, for example, a cDNA clone from a cDNA library that encodes the antibody. Amplified nucleic acids generated by PCR may then be cloned into replicable cloning vectors using any method well known in the art. In such embodiments, a polynucleotide encoding such an anti-LGALS3 antibody or antigen-binding fragment thereof can be manipulated using methods well known in the art for the manipulation of nucleotide sequences, e.g., recombinant DNA techniques, site directed mutagenesis, PCR, etc. (see, for example, the techniques described in Sambrook et al. (19900 Molecular Cloning, A Laboratory Manual, 2d Ed., Cold Spring Harbor Laboratory, Cold Spring Harbor, N.Y. and Ausubel et al., eds. (1998) Current Protocols in Molecular Biology, John Wiley & Sons, N. Y., which are both incorporated by reference herein in their entireties), to generate anti-LGALS3 antibodies or antigen-binding fragments thereof having a different amino acid sequence, for example, to create amino acid substitutions, deletions, and/or insertions. For example, such manipulations can be performed to render the encoded amino acid aglycosylated, or to destroy the antibody's ability to bind to C1q, Fc receptor, or to activate the complement system.

Isolated nucleic acid molecules provided herein can include nucleic acid molecules comprising an open reading frame (ORF), optionally with one or more introns, for example, but not limited to, at least one specified portion of at least one complementarity determining region (CDR), as CDR1, CDR2 and/or CDR3 of at least one heavy chain or light chain; nucleic acid molecules comprising the coding sequence for an anti-LGALS3 antibody or variable region; and nucleic acid molecules which comprise a nucleotide sequence substantially different from those described above but which, due to the degeneracy of the genetic code, still encode at least one anti-LGALS3 antibody or antigen-binding fragment thereof as described herein.

Also provided herein are isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides provided herein can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

The nucleic acids can conveniently comprise sequences in addition to a polynucleotide provided herein. For example, a multi-cloning site comprising one or more endonuclease restriction sites can be inserted into the nucleic acid to aid in isolation of the polynucleotide. In addition, translatable sequences can be inserted to aid in the isolation of the translated polynucleotide provided herein. For example, a hexa-histidine marker sequence (SEQ ID NO: 309) provides a convenient means to purify the polypeptides provided herein. The nucleic acid provided herein—excluding the coding sequence—is optionally a vector, adapter, or linker for cloning and/or expression of a polynucleotide provided herein.

Additional sequences can also be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

In a specific embodiment, using routine recombinant DNA techniques, one or more of the CDRs of an anti-LGALS3 antibody or antigen binding fragment thereof described herein can be inserted within known framework regions. The framework regions can be naturally occurring or consensus framework regions, and preferably human framework regions (see, e.g., Chothia et al., (1998) *J. Mol. Biol.* 278: 457-479 for a listing of human framework regions). In some embodiments, the polynucleotide generated by the combination of the framework regions and CDRs encodes an anti-LGALS3 antibody or antigen binding fragment thereof that immunospecifically binds LGALS3. One or more amino acid substitutions can be made within the framework regions, and, preferably, the amino acid substitutions improve binding of the antibody to its antigen. Additionally, such methods can be used to make amino acid substitutions or deletions of one or more variable region cysteine residues participating in an intrachain disulfide bond to generate antibody molecules lacking one or more intrachain disulfide bonds. Other alterations to the polynucleotide are provided herein and within the skill of the art.

In certain embodiments, the isolated or purified nucleic acid molecule, or fragment thereof, upon linkage with another nucleic acid molecule, can encode a fusion protein. The generation of fusion proteins is within the ordinary skill in the art and can involve the use of restriction enzyme or recombinant cloning techniques (see, for example, Gateway™ (Invitrogen)). See, also, U.S. Pat. No. 5,314,995.

In certain embodiments, a polynucleotide provided herein is in the form of a vector (e.g., expression vector). In certain aspects, provided herein are polynucleotides comprising a nucleotide sequence encoding an anti-LGALS3 antibody or antigen binding fragment thereof described herein or an antigen-binding fragment thereof (e.g., a variable light chain region and/or variable heavy chain region) that immunospecifically binds to LGALS3, and vectors, e.g., vectors comprising such polynucleotides for their efficient expression in host cells (e.g., *E. coli* and mammalian cells). In some embodiments, a polynucleotide is isolated or purified.

In particular aspects, provided herein are polynucleotides comprising nucleotide sequences encoding anti-LGALS3 antibodies or antigen binding fragments thereof and comprise an amino acid sequence as described herein, as well as antibodies which compete with such antibodies for binding to LGALS3 (e.g., in a dose-dependent manner), or which binds to the same or an overlapping epitope as that of such antibodies.

In certain aspects, provided herein are polynucleotides comprising a nucleic acid sequence encoding the light chain or heavy chain of an anti-LGALS3 antibody or antigen binding fragment thereof described herein. The polynucleotides can comprise nucleotide sequences encoding a heavy chain comprising the VH CDRs described herein (see, e.g., FIGS. 12 and 13). The polynucleotides can comprise nucleotide sequences encoding a light chain comprising the VL CDRs described herein (see, e.g., FIGS. 12 and 13).

In particular embodiments, provided herein are polynucleotides comprising a nucleotide sequence encoding an anti-LGALS3 antibody comprising three VH CDRs, e.g., containing VH CDR1, VH CDR2, and VH CDR3 as described in FIGS. 12 and 13, wherein the antibody immunospecifically binds to LGALS3. In specific embodiments, a polynucleotide described herein encodes a VH CDR1, a VH CDR2, and a VH CDR3 of the 14D11 antibody (i.e., SEQ ID NO: 5, SEQ ID NO: 6, and SEQ ID NO: 7, respectively), wherein the antibody immunospecifically binds to LGALS3. In certain embodiments, a polynucleotide described herein comprises a nucleotide sequence encoding an anti-LGALS3 antibody described herein comprising a heavy chain variable region that comprises an amino acid sequence described herein (e.g., SEQ ID NO: 24), wherein the antibody immunospecifically binds to LGALS3.

In particular embodiments, provided herein are polynucleotides comprising a nucleotide sequence encoding an anti-LGALS3 antibody comprising three VL CDRs, e.g., containing VL CDR1, VL CDR2, and VL CDR3 as described in FIGS. 12 and 13, wherein the antibody immunospecifically binds to LGALS3. In specific embodiments, a polynucleotide described herein encodes a VL CDR1, a VL CDR2, and a VL CDR3 of the 14D11 antibody (i.e., SEQ ID NO: 8, SEQ ID NO: 9, and SEQ ID NO: 10, respectively), wherein the antibody immunospecifically binds to LGALS3. In certain embodiments, a polynucleotide described herein comprises a nucleotide sequence encoding an anti-LGALS3 antibody described herein comprising a light chain variable region that comprises an amino acid sequence described herein (e.g., SEQ ID NO: 26), wherein the antibody immunospecifically binds to LGALS3.

In certain embodiments, a polynucleotide described herein comprises a nucleotide sequence encoding an anti-LGALS3 antibody described herein comprising a heavy chain variable region that comprises an amino acid sequence described herein (e.g., SEQ ID NO: 24) and a light chain variable region that comprises an amino acid sequence described herein (e.g., SEQ ID NO: 26), wherein the antibody immunospecifically binds to LGALS3.

In specific aspects, provided herein is a polynucleotide comprising a nucleotide sequence encoding an anti-LGALS3 antibody or antigen binding fragment thereof comprising a light chain and a heavy chain, e.g., a separate light chain and heavy chain. With respect to the heavy chain, in a specific embodiment, a polynucleotide provided herein comprises a nucleotide sequence encoding an alpha (α), delta (δ), epsilon (ε), gamma (γ) or mu (μ) heavy chain. With respect to the light chain, in a specific embodiment, a polynucleotide provided herein comprises a nucleotide sequence encoding a kappa (κ) or a lambda (λ) light chain.

Cells and Vectors

In certain embodiments, provided herein are cells (e.g., isolated or ex vivo cells) expressing (e.g., recombinantly) one or more anti-LGALS3 antibodies or antigen-binding fragments thereof. Also provided herein are vectors (e.g., expression vectors) comprising nucleotide sequences encoding an anti-LGALS3 antibody or antigen-binding fragment thereof described herein for recombinant expression in host cells, preferably in mammalian cells. Also provided herein are cells (e.g., isolated or ex vivo cells) comprising such vectors or nucleotide sequences for recombinantly expressing an anti-LGALS3 antibody or antigen-binding fragment thereof described here. Also provided herein are methods for producing an anti-LGALS3 antibody or antigen-binding fragment thereof described herein, comprising expressing such anti-LGALS3 antibody or antigen-binding fragment thereof from a cell (e.g., isolated or ex vivo cells).

A vector (e.g., expression vector) is a DNA molecule comprising a gene that is expressed in a cell (e.g., ex vivo cell). Typically, gene expression is placed under the control of certain regulatory elements, including constitutive or inducible promoters, tissue-specific regulatory elements and enhancers. Such a gene is said to be "operably linked to" the regulatory elements, e.g., a promoter. A recombinant host can be any prokaryotic or eukaryotic cell that contains either a cloning vector or expression vector. This term also includes those prokaryotic or eukaryotic cells, as well as a transgenic animal, that have been genetically engineered to contain the cloned gene(s) in the chromosome or genome of the host cell or cells of the host cells (e.g., ex vivo cells). In one embodiment, the promoter is the CMV promoter.

In certain embodiments, provided herein is a vector comprising one or more polynucleotide as described herein. In certain embodiments, a polynucleotide as described herein can be cloned into a suitable vector and can be used to transform or transfect any suitable host. Vectors and methods to construct such vectors are known to one of ordinary skill in the art and are described in general technical references (see, in general, "Recombinant DNA Part D," Methods in Enzymology, Vol. 153, Wu and Grossman, eds., Academic Press (1987)). In certain embodiments, the vector comprises regulatory sequences, such as transcription and translation initiation and termination codons, which are specific to the type of host (e.g., bacterium, fungus, plant, insect, or mammal) into which the vector is to be introduced, as appropriate and taking into consideration whether the vector is DNA or RNA. In certain embodiments, the vector comprises regulatory sequences that are specific to the genus of the host. In certain embodiments, the vector comprises regulatory sequences that are specific to the species of the host. In certain embodiments, the vector comprises one or more marker genes, which allow for selection of transformed or transfected hosts. Non-limiting examples of marker genes include biocide resistance, e.g., resistance to antibiotics, heavy metals, etc., complementation in an auxotrophic host to provide prototrophy, and the like. In a particular embodiment, the vector comprises ampicillin and hygromycin selectable markers.

In certain embodiments, an expression vector can comprise a native or normative promoter operably linked to a polynucleotide as described herein. The selection of promoters, for example, strong, weak, inducible, tissue-specific and developmental-specific, is within the skill in the art. Similarly, the combining of a nucleic acid molecule, or fragment thereof, as described above with a promoter is also within the skill in the art.

Non-limiting examples of suitable vectors include those designed for propagation and expansion or for expression or both. For example, a cloning vector can be selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as lamda-GTIO, lamda-GTl1, lamda-ZapII (Stratagene), lamda-EMBL4, and lamda-NMl149, can also be used. Non-limiting examples of plant expression vectors include pBIl10, pBI101.2, pBI101.3, pBI121 and pBIN19 (Clontech). Non-limiting examples of animal expression vectors include pEUK-Cl, pMAM and pMAMneo (Clontech). The TOPO cloning system (Invitrogen, Carlsbad, Calif.) can also be used in accordance with the manufacturer's recommendations.

In certain embodiments, the vector is a mammalian vector. In certain embodiments, the mammalian vector contains at least one promoter element, which mediates the initiation of transcription of mRNA, the anti-LGALS3 antibody or antigen-binding fragment thereof coding sequence, and signals required for the termination of transcription and polyadenylation of the transcript. In certain embodiments, the mammalian vector contains additional elements, such as, for example, enhancers, Kozak sequences and intervening sequences flanked by donor and acceptor sites for RNA splicing. In certain embodiments, highly efficient transcription can be achieved with, for example, the early and late promoters from SV40, the long terminal repeats (LTRS) from retroviruses, for example, RSV, HTLVI, HIVI and the early promoter of the cytomegalovirus (CMV). However, cellular elements can also be used (e.g., the human actin promoter). Non-limiting examples of mammalian expression vectors include, vectors such as pIRESlneo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Non-limiting example of mammalian host cells that can be used in combination with such mammalian vectors include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

In certain embodiments, the vector is a viral vector, for example, retroviral vectors, parvovirus-based vectors, e.g., adeno-associated virus (AAV)-based vectors, AAV-adenoviral chimeric vectors, and adenovirus-based vectors, and lentiviral vectors, such as Herpes simplex (HSV)-based vectors. In certain embodiments, the viral vector is manipulated to render the virus replication deficient. In certain embodiments, the viral vector is manipulated to eliminate toxicity to the host. These viral vectors can be prepared using standard recombinant DNA techniques described in, for example, Sambrook et al., Molecular Cloning, a Laboratory Manual, 2d edition, Cold Spring Harbor Press, Cold Spring Harbor, N.Y. (1989); and Ausubel et al., Current Protocols in Molecular Biology, Greene Publishing Associates and John Wiley & Sons, New York, N.Y. (1994).

In certain embodiments, a vector or polynucleotide described herein can be transferred to a cell (e.g., an ex vivo cell) by conventional techniques and the resulting cell can be cultured by conventional techniques to produce an anti-LGALS3 antibody or antigen-binding fragment thereof described herein. Accordingly, provided herein are cells comprising a polynucleotide encoding an anti-LGALS3 antibody or antigen-binding fragment thereof, a heavy or light chain thereof, or a light chain fusion polypeptide thereof, operably linked to a promoter for expression of such sequences in the host cell. In certain embodiments, a vector encoding the heavy chain operably linked to a promoter and a vector encoding the light chain operably linked to a promoter can be co-expressed in the cell for expression of the entire anti-LGALS3 antibody. In certain embodiments, a vector encoding a heavy chain operably linked to a promoter and a vector encoding a light chain fusion polypeptide operably linked to a promoter can be co-expressed in the cell for expression of an entire bispecific binding molecule. In certain embodiments, a cell comprises a vector comprising a polynucleotide encoding both the heavy chain and the light chain polypeptide of an anti-LGALS3 antibody described herein operably linked to a promoter. In certain embodiments, a cell comprises a vector comprising a polynucleotide encoding both the heavy chain and the light chain fusion polypeptide of a bispecific binding molecule described herein operably linked to a promoter. In certain embodiments, a cell comprises two different vectors, a first vector comprising a polynucleotide encoding a heavy chain operably linked to a promoter, and a second vector comprising a polynucleotide encoding a light chain polypeptide operably linked to a promoter. In certain embodiments, a cell comprises two different vectors, a first vector comprising a polynucleotide encoding a heavy chain operably linked to a promoter, and a second vector comprising a polynucleotide encoding a light chain fusion polypeptide operably linked to a promoter. In certain embodiments, a first cell comprises a first vector comprising a polynucleotide encoding a heavy chain of an anti-LGALS3 antibody described herein, and a second cell comprises a second vector comprising a polynucleotide encoding a light chain polypeptide of an anti-LGALS3 antibody described herein. In certain embodiments, provided herein is a mixture of cells comprising such first cell and such second cell. In certain embodiments, a first cell comprises a first vector comprising a polynucleotide encoding a heavy chain of a bispecific binding molecule described herein, and a second cell comprises a second vector comprising a polynucleotide encoding a light chain fusion polypeptide of a bispecific binding molecule described herein. In certain embodiments, provided herein is a mixture of cells comprising such first cell and such second cell. In a particular embodiment, the cell expresses the vector or vectors such that the polynucleotide is both transcribed and translated efficiently by the cell.

In some embodiments, the cell expresses the vector, such that the polynucleotide, or fragment thereof, is both transcribed and translated efficiently by the cell.

In certain embodiments, the cell is present in a host, which can be an animal, such as a mammal. Examples of cells include, but are not limited to, a human cell, a human cell line, E. coli (e.g., E. coli TB-1, TG-2, DH5a, XL-Blue MRF (Stratagene), SA2821 and Y1090), B. subtilis, P. aerugenosa, S. cerevisiae, N. crassa, insect cells (e.g., Sf9, Ea4) and others set forth herein below. In a particular embodiment, the cell is a CHO cell. In another particular embodiment, the cell is a CHO-S cell.

In certain embodiments, a polynucleotide described herein can be expressed in a stable cell line that comprises the polynucleotide integrated into a chromosome by introducing the polynucleotide into the cell. In certain embodiments, the polynucleotide is introduced into the cell by, for example, electroporation. In certain embodiments, the polynucleotide is introduced into the cell by, for example, transfection of a vector comprising the polynucleotide into the cell. In certain embodiments, the vector is co-transfected with a selectable marker such as DHFR, GPT, neomycin, or hygromycin to allow for the identification and isolation of the transfected cells. In certain embodiments, the transfected polynucleotide can also be amplified to express large amounts of the encoded anti-LGALS3 antibody or antigen-binding fragment thereof. For example, the DHFR (dihydrofolate reductase) marker can be utilized to develop cell lines that carry several hundred or even several thousand copies of the polynucleotide of interest. Another example of a selection marker is the enzyme glutamine synthase (GS) (Murphy, et al., Biochem. J. 227:277-279 (1991); Bebbington, et al., *Bio/Technology* 10: 169-175). Using these markers, the cells are grown in selective medium and the cells with the highest resistance are selected. These cell lines contain the amplified gene(s) integrated into a chromosome. Chinese hamster ovary (CHO) and NSO cells are often used for the production of antibodies.

In some embodiments, the vector comprises (i) a first polynucleotide sequence encoding an immunoglobulin light chain that binds to LGALS3, operably linked to a first promoter and (ii) a second polynucleotide encoding an immunoglobulin heavy chain that binds to LGALS3, operably linked to a second promoter. In certain embodiments, the vector is a viral vector.

In some embodiments, the vector comprises (i) a first polynucleotide sequence encoding a light chain fusion polypeptide comprising an immunoglobulin light chain fused to a scFv, via a peptide linker, wherein the light chain binds to LGALS3 and wherein the scFv binds to CD3, operably linked to a first promoter and (ii) a second polynucleotide encoding an immunoglobulin heavy chain that binds to LGALS3 operably linked to a second promoter. In certain embodiments, the vector is a viral vector.

Pharmaceutical Compositions

In certain embodiments, provided herein are compositions (e.g., pharmaceutical compositions) and kits comprising a pharmaceutically effective amount of one or more anti-LGALS3 antibodies or antigen-binding fragments thereof. In certain embodiments, the pharmaceutical compositions comprise immune cells, for example T cells, recombinantly expressing an antibody, antigen-binding fragment thereof, and/or CAR described herein. Compositions can be used in the preparation of individual, single unit dosage forms. Compositions provided herein can be formulated for parenteral, subcutaneous, intramuscular, intravenous, intrarticular, intrabronchial, intraabdominal, intracapsular, intracartilaginous, intracavitary, intracelial, intracelebellar, intracerebroventricular, intra-Ommaya, intraocular, intravitreous, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, intrathecal, intraventricular in the brain, intraparenchymal in the brain, or transdermal administration.

In certain embodiments, provided herein is a composition comprising one or more polynucleotide comprising nucleotide sequences encoding an anti-LGALS3 antibody or an antigen-binding fragment thereof described herein. In certain embodiments, provided herein is a composition comprising a cell, wherein the cell comprises one or more polynucleotides comprising nucleotide sequences encoding an anti-LGALS3 antibody or an antigen-binding fragment thereof described herein. In certain embodiments, provided herein is a composition comprising a vector, wherein the vector comprises one or more polynucleotide comprising nucleotide sequences encoding an anti-LGALS3 antibody or an antigen-binding fragment thereof described herein. In certain embodiments, provided herein is a composition comprising a cell, wherein the cell comprises a vector, wherein the vector comprises one or more polynucleotide comprising nucleotide sequences encoding an anti-LGALS3 antibody or an antigen-binding fragment thereof described herein.

In certain embodiments, a composition described herein is a stable or preserved formulation. In certain embodiments, the stable formulation comprises a phosphate buffer with saline or a chosen salt. In certain embodiments, a composition described is a multi-use preserved formulation, suitable for pharmaceutical or veterinary use. In certain embodiments, a composition described herein comprises a preservative. Preservatives are known to one of ordinary skill in the art. Non-limiting examples of preservatives include phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, and sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9%, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

It can be desirable to deliver the compositions provided herein to a subject over prolonged periods of time, for example, for periods of one week to one year or more from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g., a zinc tannate salt. Additionally, a composition provided herein, preferably, a relatively insoluble salt such as those just described, can be formulated in a gel, for example, an aluminum monostearate gel with, e.g., sesame oil, suitable for injection. Particularly particular salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer, for example, as described in U.S. Pat. No. 3,773,919. The compounds or, preferably, relatively insoluble salts such as those described above can also be formulated in cholesterol matrix silastic pellets, particularly for use in animals. Additional slow release, depot or implant compositions, e.g., gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

The range of at least one anti-LGALS3 antibody or antigen-binding fragment thereof composition provided herein includes amounts yielding upon reconstitution, if in a wet/dry system, concentrations from about 1.0 microgram/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

In certain embodiments, compositions provided herein comprise at least one of any suitable auxiliary, such as, but not limited to, diluent, binder, stabilizer, buffers, salts, lipophilic solvents, preservative, adjuvant or the like. In certain embodiments, pharmaceutically acceptable auxiliaries are particular. Non-limiting examples of, and methods of preparing such sterile solutions are well known in the art, such as, but not limited to, Gennaro, Ed., Remington's Pharmaceutical Sciences, 18th Edition, Mack Publishing Co. (Easton, Pa.) 1990.

Pharmaceutically acceptable carriers can be routinely selected that are suitable for the mode of administration, solubility and/or stability of the anti-LGALS3 antibody or antigen-binding fragment thereof described herein.

In certain embodiments, compositions provided herein contain one or more pharmaceutical excipient and/or additive. Non-limiting examples of pharmaceutical excipients and additives are proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Non-limiting examples of protein excipients include serum albumin such as human serum albumin (HSA), recombinant human albumin (rHA), gelatin, casein, and the like. Non-limiting examples of amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. In certain embodiments, the amino acid is glycine. Non-limiting examples of carbohydrate excipients include monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. In certain embodiments, the carbohydrate excipient is mannitol, trehalose, or raffinose.

In certain embodiments, a composition provided herein includes one or more buffer or a pH adjusting agent; typically, the buffer is a salt prepared from an organic acid or base. Non-limiting examples of buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. In certain embodiments, the buffer is an organic acid salts such as citrate. Other excipients, e.g., isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The compositions can cover a wide range of pHs, such as from about pH 4 to about pH 10, and particular ranges from about pH 5 to about pH 9, and a most particular range of about 6.0 to about 8.0. In some embodiments, the compositions provided herein have pH between about 6.8 and about 7.8. Preferred buffers include phosphate buffers, most preferably sodium phosphate, particularly phosphate buffered saline (PBS).

In certain embodiments, a composition provided herein includes one or more polymeric excipient/additive such as, for example, polyvinylpyrrolidones, ficolls (a polymeric sugar), dextrates (e.g., cyclodextrins, such as 2-hydroxypropyl-.beta.-cyclodextrin), polyethylene glycols, flavoring agents, antimicrobial agents, sweeteners, antioxidants, antistatic agents, surfactants (e.g., polysorbates such as "TWEEN 20" and 'TWEEN 80"), lipids (e.g., phospholipids, fatty acids), steroids (e.g., cholesterol), and/or chelating agents (e.g., EDTA).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or nonionic surfactants such as polysorbate 20 or 80 or poloxamer 184 or 188, Pluronic® polyls, other block co-polymers, and chelators such as EDTA and EGTA can optionally be added to the compositions to reduce aggregation. These additives are particularly useful if a pump or plastic container is used to administer the composition. The presence of pharmaceutically acceptable surfactant mitigates the propensity for the protein to aggregate.

Additional pharmaceutical excipients and/or additives suitable for use in a composition provided herein are known to one of skill in the art and are referenced in, for example, "Remington: The Science & Practice of Pharmacy", 19.sup.th ed., Williams & Williams, (1995), and in the "Physician's Desk Reference", 52nd ed., Medical Economics, Montvale, N.J. (1998), which are entirely incorporated herein by reference. In certain particular embodiments, the carrier or excipient materials are carbohydrates (e.g., saccharides and alditols) and buffers (e.g., citrate) or polymeric agents.

In some embodiments, the aqueous diluent optionally further comprises a pharmaceutically acceptable preservative. Exemplary preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the composition is a concentration sufficient to yield an anti-microbial effect. Such concentrations are dependent on the preservative selected and are readily determined by the skilled artisan.

The compositions provided herein can be prepared by a process which comprises mixing at least one anti-LGALS3 antibody or antigen-binding fragment thereof described herein and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-LGALS3 antibody or antigen-binding fragment thereof described herein and preservative in an aqueous diluent is carried out using conventional dissolution and mixing procedures. To prepare a suitable composition, for example, a measured amount of at least one anti-LGALS3 antibody or antigen-binding fragment thereof described herein in buffered solution is combined with the desired preservative in a buffered solution in quantities sufficient to provide the anti-LGALS3 antibody or antigen-binding fragment thereof described herein and preservative at the desired concentrations. The compositions provided herein can be prepared by a process that comprises mixing at least one anti-LGALS3 antibody or antigen-binding fragment thereof described herein and a selected buffer, preferably a phosphate buffer containing saline or a chosen salt. Mixing the at least one anti-LGALS3 antibody or antigen-binding fragment thereof described herein and buffer in an aqueous diluent is carried out using conventional dissolution and mixing procedures. To prepare a suitable composition, for example, a measured amount of at least one anti-LGALS3 antibody or antigen-binding fragment thereof described herein in water or buffer is combined with the desired buffering agent in water in quantities sufficient to provide the protein and buffer at the desired concentrations. Variations of these processes would be recognized by one of ordinary skill in the art. For example, the order the components are added, whether additional additives are used, the temperature and pH at which the composition is prepared, are all factors that can be optimized for the concentration and means of administration used.

Parenteral Formulations

In certain embodiments, a composition provided herein is formulated for parenteral injectable administration. As used herein, the term "parenteral" includes intravenous, intravascular, intramuscular, intradermal, subcutaneous, and intraocular. For parenteral administration, the composition can be formulated as a solution, suspension, emulsion or lyophilized powder in association, or separately provided, with a pharmaceutically acceptable parenteral vehicle. Non-limiting examples of such vehicles are water, saline, Ringer's solution, dextrose solution, glycerol, ethanol, and 1-10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or tri-glycerides. Parental administration is known in the art and includes, but is not limited to, conventional means of injections, a gas pressured needleless injection device as described in U.S. Pat. No. 5,851,198, and a laser perforator device as described in U.S. Pat. No. 5,839,446 entirely incorporated herein by reference.

Pulmonary Formulations

In certain embodiments, a composition comprising an anti-LGALS3 antibody or an antigen-binding fragment thereof described herein is formulated for pulmonary administration. For pulmonary administration, the composition is delivered in a particle size effective for reaching the lower airways of the lung or sinuses.

Compositions for pulmonary administration can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of an anti-LGALS3 antibody or an antigen-binding fragment thereof described herein are also known in the art. All such devices use formulations suitable for the administration for the dispensing of an anti-LGALS3 antibody or an antigen-binding fragment thereof described herein in an aerosol. Such aerosols can be comprised of either solution (both aqueous and nonaqueous) or solid particles. Metered dose inhalers like the Ventolin® metered dose inhaler, typically use a propellant gas and require actuation during inspiration (See, e.g., WO 94/16970, WO 98/35888). Dry powder inhalers like Turbuhaler™ (Astra), Rotahaler®. (Glaxo), Diskus® (Glaxo), devices marketed by Inhale Therapeutics, to name a few, use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference).

Nebulizers like the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. Such examples of commercially available inhalation devices are non-limiting examples are not intended to be limiting in scope.

In certain embodiments, a spray comprising an anti-LGALS3 antibody or an antigen-binding fragment thereof described herein can be produced by forcing a suspension or solution of at least one anti-LGALS3 antibody or antigen-binding fragment thereof described herein through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of a composition comprising at least one anti-LGALS3 antibody or antigen-binding fragment thereof described herein delivered by a sprayer have a particle size less than about 10 μm, for example in the range of about 1 μm to about 5 μm, for example about 2 μm to about 3 μm.

Formulations of a composition comprising at least one anti-LGALS3 antibody or antigen-binding fragment thereof described herein suitable for use with a sprayer typically include the at least one anti-LGALS3 antibody or antigen-binding fragment thereof described herein in an aqueous solution at a concentration of about 0.1 mg to about 100 mg per ml of solution or mg/gm, or any range or value therein, e.g., but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the anti-LGALS3 antibody or antigen-binding fragment thereof composition, such as a buffer, a reducing agent, a bulk protein, or a carbohydrate. Bulk proteins useful in formulating such a composition include albumin, protamine, or the like. Typical carbohydrates useful in formulating antibody composition proteins include sucrose, mannitol, lactose, trehalose, glucose, or the like. The composition can also include a surfactant, which can reduce or prevent surface-induced aggregation of the composition caused by atomization of the solution in forming an aerosol. Various conventional surfactants can be employed, such as polyoxyethylene fatty acid esters and alcohols, and polyoxy ethylene sorbitol fatty acid esters. Amounts will generally range between 0.001 and 14% by weight of the formulation. Preferred surfactants are polyoxyethylene sorbitan monooleate, polysorbate 80, polysorbate 20, or the like.

In certain embodiments, the composition is administered via a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition protein either directly or through a coupling fluid, creating an aerosol including the antibody composition protein. Advantageously, particles of antibody composition protein delivered by a nebulizer have a particle size less than about 10 um, preferably in the range of about 1 um to about 5 um, and most preferably about 2 um to about 3 um.

In certain embodiments, the composition is administered via a metered dose inhaler (MDI), wherein a propellant, at least one anti-LGALS3 antibody or antigen-binding fragment thereof described herein, and any excipients or other additives are contained in a canister as a mixture including a liquefied compressed gas.

Actuation of the metering valve releases die mixture as an aerosol, preferably containing particles in the size range of less than about 10 um, preferably about 1 um to about 5 um, and most preferably about 2 um to about 3 um. The desired aerosol particle size can be obtained by employing a formulation of antibody composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of an anti-LGALS3 antibody or an antigen-binding fragment thereof described herein for use with a metered-dose inhaler device will generally include a finely divided powder containing at least one Anti-IL-6 antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluoroalkane-134a), HFA-227 (hydrofluoroalkane-227), or the like. In some embodiments, the propellant is a hydrofluorocarbon. The surfactant can be chosen to stabilize the at least one anti-LGALS3 antibody or antigen-binding fragment thereof described herein as a suspension in the propellant, to protect the active agent against chemical degradation, and the like. Suitable surfactants include sorbitan trioleate, soya lecithin, oleic acid, or the like. In some cases, solution aerosols are particular using solvents such as ethanol.

Additional agents known in the art for formulation of a protein can also be included in the formulation.

Oral Formulations

In certain embodiments, a composition provided herein is formulated for oral administration. In certain embodiments, for oral administration, compositions and methods of administering at least one anti-LGALS3 antibody or antigen-binding fragment thereof described herein rely on the co-administration of adjuvants such as, for example, resorcinols and nonionic surfactants such as polyoxyethylene oleyl ether and n-hexadecylpolyethylene ether, to artificially increase the permeability of the intestinal walls, as well as the co-administration of enzymatic inhibitors such as, for example, pancreatic trypsin inhibitors, diisopropylfluorophosphate (DFF) and trasylol, to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, such as, for example, inactive diluting agent, lubricant such as magnesium stearate, paraben, preserving agent such as sorbic acid, ascorbic acid, alpha.-tocopherol, antioxidant such as cysteine, disintegrator, binder, thickener, buffering agent, sweetening agent, flavoring agent, perfuming agent, etc.

In certain embodiments, tablets and pills for oral administration can be further processed into enteric-coated preparations. In certain embodiments, liquid preparations for oral administration include, for example, emulsion, syrup, elixir, suspension and solution preparations allowable for medical use. These preparations can contain inactive diluting agents ordinarily used in said field, for example, water. Liposome preparations can be utilized for oral administration preparations, for example, as described for insulin and heparin (U.S. Pat. No. 4,239,754). Additionally, microspheres of artificial polymers of mixed amino acids (proteinoids) can be utilized to in oral administration of pharmaceuticals, for example, as described in U.S. Pat. No. 4,925,673. Furthermore, carrier compounds, such as those described in U.S. Pat. Nos. 5,879,681 and 5,871,753, are used in oral administration of biologically active agents.

Mucosal Formulations

In certain embodiments, a composition provided herein is formulated for absorption through mucosal surfaces. In certain embodiments, for absorption through mucosal surfaces, compositions and methods of administering at least one anti-LGALS3 antibody or antigen-binding fragment thereof described herein include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions provided herein can include, for example, corneal, conjunctival, buccal, sublingual, nasal, vaginal, pulmonary, stomachic, intestinal, and rectal routes of administration. Formulations for vaginal or rectal administration, for example, suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include, for example, sugars, calcium stearate, magnesium stearate, pregelinatined starch, and the like (U.S. Pat. No. 5,849,695).

Transdermal Formulations

In certain embodiments, a composition provided herein is formulated for transdermal administration. In certain embodiments, for transdermal administration, the composition comprises at least one anti-LGALS3 antibody or antigen-binding fragment thereof described herein encapsulated in a delivery device such as, for example, a liposome or polymeric nanoparticles, microparticle, microcapsule, or microspheres (referred to collectively as microparticles unless otherwise stated). A number of suitable devices are known for transdermal administration, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

Kits

Also provided herein are kits comprising one or more antibodies described herein, or antigen-binding fragments thereof, or conjugates thereof. In a specific embodiment, provided herein is a pharmaceutical pack or kit comprising one or more containers filled with one or more of the ingredients of the pharmaceutical compositions described herein, such as one or more antibodies or an antigen-binding fragment thereof described herein. In some embodiments, the kits contain a pharmaceutical composition described herein and a prophylactic or therapeutic agent.

Optionally associated with such container(s) can be a notice in the form prescribed by a governmental agency regulating the manufacture, use or sale of pharmaceuticals or biological products, a dosage form, and/or instructions for use thereof. In certain embodiments, the instructions included with the kit provide guidance with respect to the dosage amounts and/or dosing regimens for administration of the pharmaceutical composition(s).

Examples of pharmaceutical packaging materials include, but are not limited to, blister packs, bottles, packets, sachets, tubes, inhalers, pumps, bags, vials, containers, syringes and any packaging material suitable for a selected pharmaceutical composition and intended mode of administration and treatment.

Kits provided herein can further include devices that are used to administer the active ingredients. Examples of such devices include, but are not limited to, syringes, needle-less injectors, drip bags, patches and inhalers.

Kits provided herein can further include pharmaceutically acceptable vehicles that can be used to administer the ingredients. For example, if an ingredient is provided in a solid form that must be reconstituted for parenteral administration, the kit can comprise a sealed container of a suitable vehicle in which the ingredient can be dissolved to form a particulate-free sterile solution that is suitable for parenteral administration or can be reconstituted as a suspension for oral administration. Examples of pharmaceutically acceptable vehicles include, but are not limited to: aqueous vehicles including, but not limited to, Water for Injection USP, Sodium Chloride Injection, Ringer's Injection, Dextrose Injection, Dextrose and Sodium Chloride Injection, and Lactated Ringer's Injection; water-miscible vehicles including, but not limited to, ethyl alcohol, polyethylene glycol, and polypropylene glycol; and non-aqueous vehicles including, but not limited to, corn oil, cottonseed oil, peanut oil, sesame oil, ethyl oleate, isopropyl myristate, and benzyl benzoate.

Uses and Methods

Therapeutic Uses and Methods

In certain embodiments, provided herein are methods for treating a LGALS3-related disease or condition comprising administering to the subject in need thereof a therapeutically effective amount of an anti-LGALS3 antibody or antigen-binding fragment thereof. Exemplary LGALS3-related disease or conditions include, but are not limited to, cancer, tumor metastasis, tumor angiogenesis, heart failure, pulmonary fibrosis, glomerular disease of the kidney, inflammatory disease, and rheumatic diseases.

In a specific embodiment, the anti-LGALS3 antibody or antigen-binding fragment thereof is administered in combination with one or more additional therapeutic agents. In some embodiments, the one or more additional therapeutic agents inhibit or treat one or more symptoms of the LGALS3-related disease or condition.

In certain embodiments, provided herein are methods for treating cancer in a subject, in particular, a LGALS3-positive cancer in a subject, comprising administering to the subject in need thereof a therapeutically effective amount of an anti-LGALS3 antibody or antigen-binding fragment thereof. In a specific embodiment, the LGALS3-positive cancer is ovarian cancer, lung cancer, pancreatic cancer, breast cancer, fallopian tube cancer, uterine (e.g., endometrial) cancer, primary peritoneum cancer or cancer of any other tissue that expresses LGALS3.

For use of an anti-LGALS3 antibody or fragment thereof in a subject of a particular species, an anti-LGALS3 antibody or fragment thereof is used that binds to LGALS3 of that particular species. For example, to treat a human, an anti-LGALS3 antibody or antigen-binding fragment thereof is used that binds to human LGALS3. In a specific embodiment, the anti-LGALS3 antibody or antigen-binding fragment thereof is an immunoglobulin.

In addition, for use of an anti-LGALS3 antibody or fragment thereof in a subject of a particular species, the anti-LGALS3 antibody, in certain embodiments, the constant region of an anti-LGALS3 antibody or antigen binding fragment thereof, is derived from that particular species. For example, to treat a human, the anti-LGALS3 antibody or fragment thereof can comprise an anti-LGALS3 antibody or antigen binding fragment thereof that is an immunoglobulin, wherein the immunoglobulin comprises a human constant region. In a specific embodiment, the subject is a human.

In specific embodiments, treatment can be to achieve beneficial or desired clinical results including, but not limited to, alleviation of a symptom, diminishment of extent of a disease, stabilizing (i.e., not worsening) of state of a disease, delay or slowing of disease progression, amelioration or palliation of the disease state, and remission (whether partial or total), whether detectable or undetectable. In a specific embodiment, "treatment" can also be to prolong survival as compared to expected survival if not receiving treatment. In specific embodiments, the administration of an anti-LGALS3 antibody or antigen binding fragment thereof described herein, or a pharmaceutical composition described herein to a subject with cancer (e.g., ovarian cancer, lung cancer, pancreatic cancer, breast cancer, fallopian tube cancer, uterine (e.g., endometrial) cancer, or primary peritoneum cancer, or cancer of any other tissue that expresses LGALS3) achieves at least one, two, three, four or more of the following effects: (i) the reduction or amelioration of the severity of one or more symptoms of cancer; (ii) the reduction in the duration of one or more symptoms associated with cancer; (iii) the prevention in the recurrence of a symptom associated with cancer; (iv) the reduction in hospitalization of a subject; (v) a reduction in hospitalization length; (vi) the increase in the survival of a subject; (vii) the enhancement or improvement of the therapeutic effect of another therapy; (viii) the inhibition of the development or onset of one or more symptoms associated with cancer; (ix) the reduction in the number of symptoms associated with cancer; (x) improvement in quality of life as assessed by methods well known in the art; (x) inhibition of the recurrence of a tumor; (xi) the regression of tumors and/or one or more symptoms associated therewith; (xii) the inhibition of the progression of tumors and/or one or more symptoms associated therewith; (xiii) a reduction in the growth of a tumor; (xiv) a decrease in tumor size (e.g., volume or diameter); (xv) a reduction in the formation of a newly formed tumor; (xvi) prevention, eradication, removal, or control of primary, regional and/or metastatic tumors; (xvii) a decrease in the number or size of metastases; (xviii) a reduction in mortality; (xix) an increase in relapse free survival; (xx) the size of the tumor is maintained and does not increase or increases by less than the increase of a tumor after administration of a standard therapy as measured by conventional methods available to one of skill in the art, such as magnetic resonance imaging (MM), dynamic contrast-enhanced MRI (DCE-MRI), X-ray, and computed tomography (CT) scan, or a positron emission tomography (PET) scan; and/or (xxi) an increase in the length of remission in patients. Treatment can be to achieve one or more of the foregoing.

Diagnostic Uses

In certain embodiments, anti-LGALS3 antibodies or antigen-binding fragments thereof described herein can be used for diagnostic purposes to detect, diagnose, or monitor a condition described herein (e.g., a condition involving LGALS3-positive cancer cells). In certain embodiments, anti-LGALS3 antibodies or antigen-binding fragments thereof for use in diagnostic purposes are labeled.

In certain embodiments, provided herein are methods for the detection of a condition described herein comprising (a) assaying the expression of LGALS3 or a fragment thereof in cells or a tissue sample of a subject using one or more anti-LGALS3 antibodies or antigen-binding fragments thereof described herein; and (b) comparing the level of LGALS3 or the fragment thereof expression with a control level, for example, levels in normal tissue samples (e.g., from a subject not having a condition described herein, or from the same patient before onset of the condition), whereby an increase or decrease in the assayed level of LGALS3 or the fragment thereof expression compared to the control level of LGALS3 or the fragment thereof expression is indicative of a condition described herein.

Antibodies described herein can be used to assay the levels of LGALS3 or a fragment thereof in a biological sample using classical immunohistological methods as described herein or as known to those of skill in the art (e.g., see Jalkanen et al., 1985, J. Cell. Biol. 101:976-985; and Jalkanen et al. (1987) *J. Cell. Biol.* 105:3087-3096). Other antibody-based methods useful for detecting protein gene expression include immunoassays, such as the enzyme linked immunosorbent assay (ELISA) and the radioimmunoassay (MA). Suitable antibody assay labels are known in the art and include enzyme labels, such as, glucose oxidase; radioisotopes, such as iodine ($^{125}$I, 121I), carbon ($^{14}$C), sulfur ($^{35}$S), tritium ($^3$H), indium ($^{121}$In), and technetium ($^{99}$Tc); luminescent labels, such as luminol; and fluorescent labels, such as fluorescein and rhodamine, and biotin.

In certain embodiments, monitoring of a condition described herein (e.g., a LGALS3-positive cancer), is carried out by repeating the method for diagnosing for a period of time after initial diagnosis.

Presence of the labeled molecule can be detected in the subject using methods known in the art for in vivo scanning. Skilled artisans will be able to determine the appropriate method for detecting a particular label. Methods and devices that can be used in the diagnostic methods of the invention include, but are not limited to, computed tomography (CT), whole body scan such as position emission tomography (PET), magnetic resonance imaging (MM), and sonography.

Doses and Regimens

An anti-LGALS3 antibody or antigen-binding fragment thereof, or composition, or cells expressing the antibodies, or antigen-binding fragments thereof, described herein can be delivered to a subject by a variety of routes. These include, but are not limited to, parenteral, intranasal, intratracheal, oral, intradermal, topical, intramuscular, intraperitoneal, transdermal, intravenous, intratumoral, conjunctival and subcutaneous routes. Pulmonary administration can also be employed, e.g., by use of an inhaler or nebulizer, and formulation with an aerosolizing agent for use as a spray. In one embodiment, an anti-LGALS3 antibody or antigen-binding fragment thereof, or a composition described herein is administered parenterally to a subject. In a specific embodiment, said parenteral administration is intravenous, intramuscular, or subcutaneous.

The amount of an anti-LGALS3 antibody or antigen-binding fragment thereof, or composition which will be effective in the treatment and/or prevention of a condition will depend on the nature of the disease, and can be determined by standard clinical techniques.

The precise dose to be employed in a composition will also depend on the route of administration, and the type of cancer, and should be decided according to the judgment of the practitioner and each subject's circumstances. For example, effective doses may also vary depending upon means of administration, target site, physiological state of the patient (including age, body weight and health), whether the patient is human or animal, other medications administered, or whether treatment is prophylactic or therapeutic. Treatment dosages are optimally titrated to optimize safety and efficacy.

In certain embodiments, an in vitro assay is employed to help identify optimal dosage ranges. Effective doses can be extrapolated from dose response curves derived from in vitro or animal model test systems.

For an anti-LGALS3 antibody or antigen binding fragment thereof, the dosage can range from about 0.0001 to 100 mg/kg, and more usually 0.01 to 15 mg/kg, of the patient body weight. For example, dosages can be 1 mg/kg body weight, 10 mg/kg body weight, or within the range of 1-10 mg/kg or in other words, 70 mg or 700 mg or within the range of 70-700 mg, respectively, for a 70 kg patient.

Generally, human antibodies have a longer half-life within the human body than antibodies from other species due to the immune response to the foreign polypeptides. Thus, lower dosages of human antibodies and less frequent administration is often possible.

In certain embodiments, such as in the administration of engineered cells expressing the antibodies or antigen-binding fragments thereof, or CARs, a subject is administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges. In some embodiments, the dose of total cells and/or dose of individual sub-populations of cells is within a range of between at or about $10^4$ and at or about $10^9$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg, $2\times10^6$ cells/kg, $5\times10^6$ cells/kg, or $10\times10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^7$ T cells/kg body weight.

An anti-LGALS3 antibody or antigen-binding fragment thereof can be administered on multiple occasions. Intervals between single dosages can be, for example, 1 week, 2 weeks, 3 weeks, 4 weeks, 1 month, 2 months, 3 months, 6 months, 1 year, or 2 years.

Combination Therapies

In a specific embodiment, the methods provided herein for treating cancer (e.g., ovarian cancer, pancreatic cancer, lung cancer, breast cancer, fallopian tube cancer, uterine (e.g., endometrial) cancer, or primary peritoneum cancer) in a subject, comprising administering to a subject in need thereof a pharmaceutical composition comprising an anti-LGALS3 antibody or an antigen-binding fragment thereof described herein, further comprise administering to the subject one or more additional therapeutic agents. In a specific embodiment, the additional therapeutic agent is for treating the cancer in the subject (e.g., ovarian cancer, pancreatic cancer, lung cancer, breast cancer, fallopian tube cancer, uterine (e.g., endometrial) cancer, and primary peritoneum cancer). In a specific embodiment, the additional therapeutic agent is for treating any side effects of treatment with an anti-LGALS3 antibody or an antigen-binding fragment described herein described herein.

In specific embodiments, the additional agent is an agent used to treat ovarian cancer. In specific embodiments, the additional agent is an agent used to treat pancreatic cancer. In specific embodiments, the additional agent is an agent used to treat lung cancer. In specific embodiments, the additional agent is an agent used to treat breast cancer. In specific embodiments, the additional agent is an agent used to treat fallopian tube cancer. In specific embodiments, the additional agent is an agent used to treat uterine (e.g., endometrial) cancer. In specific embodiments, the additional agent is an agent used to treat primary peritoneum cancer.

An anti-LGALS3 antibody or an antigen-binding fragment thereof described herein described herein can be administered with an additional therapeutic agent concurrently or sequentially (before and/or after). The antibody or antigen binding fragment thereof and the additional therapeutic agent can be administered in the same or different compositions, and by the same or different routes of administration. A first therapy (which is an anti-LGALS3 antibody or an antigen-binding fragment thereof described herein, or the additional therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second therapy (the anti-LGALS3 antibody or antigen-binding fragment thereof described herein described herein, or the additional therapeutic agent) to a subject with cancer (e.g., ovarian cancer, pancreatic cancer, lung cancer, breast cancer, fallopian tube cancer, uterine (e.g., endometrial) cancer, and primary peritoneum cancer). In certain embodiments, an additional therapeutic agent administered to a subject in combination with anti-LGALS3 antibody or antigen-binding fragment thereof described herein is administered in the same composition (pharmaceutical composition). In other embodiments, an additional therapeutic agent administered in combination with anti-LGALS3 antibody or an antigen-binding fragment thereof described herein is administered to a subject in a different composition than the anti-LGALS3 antibody or antigen-binding fragment thereof described herein (e.g., two or more pharmaceutical compositions are used).

Patient Population

A subject treated in accordance with the methods provided herein can be any mammal, such as a rodent, a cat, a canine, a horse, a cow, a pig, a monkey, a primate, or a human, etc. In a particular embodiment, the subject is a human. In another particular embodiment, the subject is a canine. As used herein, the terms "subject" and "patient" are used interchangeably.

In certain embodiments, a subject treated in accordance with the methods provided herein has been diagnosed with a LGALS3-positive cancer, including but not limited to, ovary, lung, pancreas, breast, uterine, fallopian tube, or primary peritoneum cancer, or cancer of any other tissue that expresses the LGALS3.

The following examples are offered by way of illustration and not by way of limitation.

EXAMPLES

Example 1. Generation of Galectin-3-Fc Domain Fusion Protein

A Galectin-3(LGALS3)-Fc domain fusion protein was generated for use as an antigen and for studying LGALS3 function.

Previously, mucin-16 (MUC16) ectodomain monoclonal antibodies and fusion proteins were generated using pFUSE-hIgG1-Fc2 vector (InvivoGen) that serves as a 'dummy' antibody with human IgG1-Fc backbone (see Rao et al. (2015) *PLoS One* 10, e012663; Rao et al. (2017) *ACS Chem. Biol.* 12: 2085-2096, each of which are incorporated by reference in its entirety). The pFUSE-hIgG1-Fc2 vector allows for the generation of a Fc-fusion protein comprising a selected antigen (e.g. LGALS3) linked to the Fc region (CH2 and CH3 domains) of the human IgG1 heavy chain and the hinge region. The hinge serves as a flexible spacer between the two parts of the Fc-fusion protein, allowing each part of the molecule to function independently. A 20 amino acid IL-2 signal sequence is linked to the N-terminus of the selected antigen and allows for secretion of the antigenic fusion protein. The IL-2 signal peptide is intracellularly cleaved after Ser20.

PCR primers were designed with the restriction enzyme site EcoRV as the forward primer and NcoI as the reverse primer to extract the DNA encoding a fragment of LGALS3 (amino acids 117-244 of SEQ ID NO:1, underlined below), which includes the LGALS3 sugar-binding domain (FIG. 4, bolded below).

HUMAN Galectin-3

(SEQ ID NO: 1)
MADNFSLHDALSGSGNPNPQGWPGAWGNQPAGAGGYPGASYPGAYPGQAP

PGAYPGQAPPGAYPGAPGAYPGAPAPGVYPGPPSGPGAYPSSGQPSATGA

YPATGPYGAPAGPLIV<u>PYNLPLPGGVVPRMLITILGTVKPNANRIALDFQ</u>

<u>RGNDVAFHFNPRFNENNRRVIVCNTKLDNNWGREERQSVFPFESGKPFKI</u>

<u>QVLVEPDHFKVAVNDAHLLQYNHRVKKLNEISKLGISGDIDLTS</u>ASYTMI

The template employed for the PCR amplification was a LGALS3 cDNA clone BC001120.2 (MGC:2058 IMAGE: 3050135 GenBank: AAH01120.1) obtained from ATCC (Manassas, VA)). The BC001120.2 Galectin-3 cDNA clone has the following nucleotide sequence (the full coding sequence for LGALS3 is italicized, and the amplified portion is underlined)

(SEQ ID NO: 29)
CCGGAGCCAGCCAACGAGCGGAAAAT*GGCAGACAATTTTTCGCTCCATGA*

*TGCGTTATCTGGGTCTGGAAACCCAAACCCTCAAGGATGGCCTGGCGCAT*

*GGGGGAACCAGCCTGCTGGGGCAGGGGGCTACCCAGGGGCTTCCTATCCT*

*GGGGCCTACCCCGGGCAGGCACCCCCAGGGGCTTATCCTGGACAGGCACC*

*TCCAGGCGCCTACCCTGGAGCACCTGGAGCTTATCCCGGAGCACCTGCAC*

*CTGGAGTCTACCCAGGGCCACCCAGCGGCCCTGGGGCCTACCCATCTTCT*

*GGACAGCCAAGTGCCACCGGAGCCTACCCTGCCACTGGCCCCTATGGCGC*

*CCCTGCTGGGCCACTGATTGTG*<u>*CCTTATAACCTGCCTTTGCCTGGGGAG*</u>

<u>*TGGTGCCTCGCATGCTGATAACAATTCTGGGCACGGTGAAGCCCAATGCA*</u>

<u>*AACAGAATTGCTTTAGATTTCCAAAGAGGGAATGATGTTGCCTTCCACTT*</u>

<u>*TAACCCACGCTTCAATGAGAACAACAGGAGAGTCATTGTTTGCAATACAA*</u>

<u>*AGCTGGATAATAACTGGGGAAGGGAAGAAAGACAGTCGGTTTTCCCATTT*</u>

<u>*GAAAGTGGGAAACCATTCAAAATACAAGTACTGGTTGAACCTGACCACTT*</u>

<u>*CAAGGTTGCAGTGAATGATGCTCACTTGTTGCAGTACAATCATCGGGTTA*</u>

-continued

AAAAACTCAATGAAATCAGCAAACTGGGAATTTCTGGTGACATAGACCTC
ACCAGTGCTTCATATACCATGATATAATCTGAAAGGGGCAGATTAAAAAA
AAAAAAAAAAAA

The amplified portion encodes 117-244 LGALS3 having the amino acid sequence:

(SEQ ID NO: 27)
PYNLPLPGGVVPRMLITILGTVKPNANRIALDFQRGNDVAFHFNPRFNEN

NRRVIVCNTKLDNNWGREERQSVFPFESGKPFKIQVLVEPDHFKVAVNDA

HLLQYNHRVKKLNEISKLGISGDIDLTS

The PCR product encoding $^{117\text{-}244}$LGALS3 was then purified on a 1% agarose gel, sequenced, and inserted into the pFUSE-IgG1-Fc2 vector (Invivogen) to generate $^{117\text{-}244}$LGALS3-pFUSE-hIgG1-Fc2. This mimics Galectin-3 sugar binding but lacks the ability to form Galectin-3 pentamers, preventing formation of the stabilizing Galectin-3 gel/matrix.

The pFUSE-IgG1-Fc2 vector (Invivogen) has the following nucleic acid sequence (EcoRI and NcoI cloning sites are underlined:

(SEQ ID NO: 30)
GGATCTGCGATCGCTCCGGTGCCCGTCAGTGGGCAGAGCGCACATCGCCC
ACAGTCCCCGAGAAGTTGGGGGGAGGGGTCGGCAATTGAACGGGTGCCTA
GAGAAGGTGGCGCGGGGTAAACTGGGAAAGTGATGTCGTGTACTGGCTCC
GCCTTTTTCCCGAGGGTGGGGGAGAACCGTATATAAGTGCAGTAGTCGCC
GTGAACGTTCTTTTTCGCAACGGGTTTGCCGCCAGAACACAGCTGAAGCT
TCGAGGGGCTCGCATCTCTCCTTCACGCGCCCGCCGCCCTACCTGAGGCC
GCCATCCACGCCGGTTGAGTCGCGTTCTGCCGCCTCCCGCCTGTGGTGCC
TCCTGAACTGCGTCCGCCGTCTAGGTAAGTTTAAAGCTCAGGTCGAGACC
GGGCCTTTGTCCGGCGCTCCCTTGGAGCCTACCTAGACTCAGCCGGCTCT
CCACGCTTTGCCTGACCCTGCTTGCTCAACTCTACGTCTTTGTTTCGTTT
TCTGTTCTGCGCCGTTACAGATCCAAGCTGTGACCGGCGCCTACCTGAGA
TCACCGGcGAAGGAGGGCCACCATGTACAGGATGCAACTCCTGTCTTGCA
TTGCACTAAGTCTTGCACTTGTCAC<u>GAATTC</u>GATATC<u>GGCCATG</u>GTTAGA
TCTGACAAAACTCACACATGCCCACCGTGCCCAGCACCTGAACTCCTGGG
GGGACCGTCAGTCTTCCTCTTCCCCCCAAAACCCAAGGACACCCTCATGA
TCTCCCGGACCCCTGAGGTCACATGCGTGGTGGTGGACGTGAGCCACGAA
GACCCTGAGGTCAAGTTCAACTGGTACGTGGACGGCGTGGAGGTGCATAA
TGCCAAGACAAAGCCGCGGGAGGAGCAGTACAACAGCACGTACCGTGTGG
TCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCCC
CATCCCGGGAGGAGATGACCAAGAACCAGGTCAGCCTGACCTGCCTGGTC
AAAGGCTTCTATCCCAGCGACATCGCCGTGGAGTGGGAGAGCAATGGGCA

GCCGGAGAACAACTACAAGACCACGCCTCCCGTGCTGGACTCCGACGGCT
CCTTCTTCCTCTACAGCAAGCTCACCGTGGACAAGAGCAGGTGGCAGCAG
GGGAACGTCTTCTCATGCTCCGTGATGCACGAGGCTCTGCACAACCACTA
CACGCAGAAGAGCCTCTCCCTGTCTCCGGGTAAATGAGTGCTAGCTGGCC
AGACATGATAAGATACATTGATGAGTTTGGACAAACCACAACTAGAATGC
AGTGAAAAAAATGCTTTATTTGTGAAATTTGTGATGCTATTGCTTTATTT
GTAACCATTATAAGCTGCAATAAACAAGTTAACAACAACAATTGCATTCA
TTTTATGTTTCAGGTTCAGGGGGAGGTGTGGGAGGTTTTTTAAAGCAAGT
AAAACCTCTACAAATGTGGTATGGAATTAATTCTAAAATACAGCATAGCA
AAACTTTAACCTCCAAATCAAGCCTCTACTTGAATCCTTTTCTGAGGGAT
GAATAAGGCATAGGCATCAGGGGCTGTTGCCAATGTGCATTAGCTGTTTG
CAGCCTCACCTTCTTTCATGGAGTTTAAGATATAGTGTATTTTCCCAAGG
TTTGAACTAGCTCTTCATTTCTTTATGTTTTAAATGCACTGACCTCCCAC
ATTCCCTTTTTAGTAAAATATTCAGAAATAATTTAAATACATCATTGCAA
TGAAATAAATGTTTTTTATTAGGCAGAATCCAGATGCTCAAGGCCCTTC
ATAATATCCCCCAGTTTAGTAGTTGGACTTAGGGAACAAAGGAACCTTTA
ATAGAAATTGGACAGCAAGAAAGCGAGCTTCTAGCTTATCCTCAGTCCTG
CTCCTCTGCCACAAAGTGCACGCAGTTGCCGGCCGGGTCGCGCAGGGCGA
ACTCCCGCCCCCACGGCTGCTCGCCGATCTCGGTCATGGCCGGCCCGGAG
GCGTCCCGGAAGTTCGTGGACACGACCTCCGACCACTCGGCGTACAGCTC
GTCCAGGCCGCGCACCCACACCCAGGCCAGGGTGTTGTCCGGCACCACCT
GGTCCTGGACCGCGCTGATGAACAGGGTCACGTCGTCCCGGACCACACCG
GCGAAGTCGTCCTCCACGAAGTCCCGGGAGAACCCGAGCCGGTCGGTCCA
GAACTCGACCGCTCCGGCGACGTCGCGCGCGGTGAGCACCGGAACGGCAC
TGGTCAACTTGGCCATGATGGCTCCTctgtcaggagaggaaagagaaga
aggttagtacaattgCTATAGTGAGTTGTATTATACTATGCAGATATACT
ATGCCAATGATTAATTGTCAAACTAGGGCTGCAgggttcatagtgccact
tttcctgcactgccccatctcctgccacccttttcccaggcatagacagt
cagtgacttacCAAACTCACAGGAGGGAGAAGGCAGAAGCTTGAGACAGA
CCCGCGGGACCGCCGAACTGCGAGGGGACGTGGCTAGGGCGGCTTCTTTT
ATGGTGCGCCGGCCCTCGGAGGCAGGGCGCTCGGGGAGGCCTAGCGGCCA
ATCTGCGGTGGCAGGAGGCGGGGCCGAAGGCCGTGCCTGACCAATCCGGA
GCACATAGGAGTCTCAGCCCCCCGCCCCAAAGCAAGGGGAAGTCACGCGC
CTGTAGCGCCAGCGTGTTGTGAAATGGGGGCTTGGGGGGTTGGGGCCCT
GACTAGTCAAAACAAACTCCCATTGACGTCAATGGGGTGGAGACTTGGAA
ATCCCCGTGAGTCAAACCGCTATCCACGCCCATTGATGTACTGCCAAAAC
CGCATCATCATGGTAATAGCGATGACTAATACGTAGATGTACTGCCAAGT
AGGAAAGTCCCATAAGGTCATGTACTGGGCATAATGCCAGGCGGGCCATT
TACCGTCATTGACGTCAATAGGGGGCGTACTTGGCATATGATACACTTGA
TGTACTGCCAAGTGGGCAGTTTACCGTAAATACTCCACCCATTGACGTCA -continued
```
ATGGAAAGTCCCTATTGGCGTTACTATGGGAACATACGTCATTATTGACG

TCAATGGGCGGGGTCGTTGGGCGGTCAGCCAGGCGGGCCATTTACCGTA

AGTTATGTAACGCCTGCAGGTTAATTAAGAACATGTGAGCAAAAGGCCAG

CAAAAGGCCAGGAACCGTAAAAAGGCCGCGTTGCTGGCGTTTTTCCATAG

GCTCCGCCCCCTGACGAGCATCACAAAAATCGACGCTCAAGTCAGAGGT

GGCGAAACCCGACAGGACTATAAAGATACCAGGCGTTTCCCCCTGGAAGC

TCCCTCGTGCGCTCTCCTGTTCCGACCCTGCCGCTTACCGGATACCTGTC

CGCCTTTCTCCCTTCGGGAAGCGTGGCGCTTTCTCATAGCTCACGCTGTA

GGTATCTCAGTTCGGTGTAGGTCGTTCGCTCCAAGCTGGGCTGTGTGCAC

GAACCCCCCGTTCAGCCCGACCGCTGCGCCTTATCCGGTAACTATCGTCT

TGAGTCCAACCCGGTAAGACACGACTTATCGCCACTGGCAGCAGCCACTG

GTAACAGGATTAGCAGAGCGAGGTATGTAGGCGGTGCTACAGAGTTCTTG

AAGTGGTGGCCTAACTACGGCTACACTAGAAGAACAGTATTTGGTATCTG

CGCTCTGCTGAAGCCAGTTACCTTCGGAAAAAGAGTTGGTAGCTCTTGAT

CCGGCAAACAAACCACCGCTGGTAGCGGTGGTTTTTTTGTTTGCAAGCAG

CAGATTACGCGCAGAAAAAAGGATCTCAAGAAGATCCTTTGATCTTTTC

TACGGGGTCTGACGCTCAGTGGAACGAAAACTCACGTTAAGGGATTTTGG

TCATGGCTAGTTAATTAACATTTAAATCAGCGGCCGCAATAAAATATCTT

TATTTTCATTACATCTGTGTGTTGGTTTTTGTGTGAATCGTAACTAACA

TACGCTCTCCATCAAAACAAAACGAAACAAAACAAACTAGCAAAATAGGC

TGTCCCCAGTGCAAGTGCAGGTGCCAGAACATTTCTCTATCGAA.
```

The fusion protein was expressed in human 293 cells and purified on a protein A column for immunization. The expressed fusion protein has the following sequence:

```
                                          (SEQ ID NO: 31)
MYRMQLLSCIALSLALVTNSPYNLPLPGGVVPRMLITILGTVKPNANRIA

LDFQRGNDVAFHFNPRFNENNRRVIVCNTKLDNNWGREERQSVFPFESGK

PFKIQVLVEPDHFKVAVNDAHLLQYNHRVKKLNEISKLGISGDIDLTSMV

RSDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGK
```

A second sugar-binding fusion protein ($^{11-119}$pFUSE) was created as a negative control with the sugar-binding domain of Galectin-1.

Example 2. Inhibition of Galectin-3 Inhibits Oncogene Activation, Cell Invasion and Tumor Growth Prior studies by the inventors have established a role for LGALS3-Mucin 16 interaction ovarian tumor growth and invasion as described in Rao et al. (2017) ACS Chem. Biol. 12: 2085-2096, which is incorporated herein by reference in its entirety. Selected experiments from this study are highlighted herein, which support LGALS3 as a target for therapeutic antibody development.

FIG. 2A illustrates LGALS3 shRNA blocking MUC16 oncogene activation, as assessed by inhibition of phosphorylation of several oncogenes, including EGFR, AKT, ERK and SRC (P-EGFR, P-AKT, P-ERK, P-SRC, respectively). Expression of MUC16 in SKOV3 cells increased phosphorylation of pERK1/2, pSRC, and EGFR. However, shRNA knockdowns of MGAT5 (shMGAT5), Galectin-3 (shLGALS3), and N→A mutation of N30 of MUC16 all impair MUC16c114-induced oncogene activation. MGAT5 (mannosyl(alpha-1,6-)-glycoprotein beta-1,6-N-acetyl-glucosaminyltransferase) catalyzes the formation of tetra-antennary N-glycans, binding Galectin-3 with the high affinity. Similar effects occurred in A2780-MUC16 cells. Thus, loss of LGALS3 greatly inhibits MUC16 activation (MUC16c344) of a variety of oncogenes in two ovarian models.

FIG. 2B illustrates competing LGALS3 but not LGAL1 (Galectin-1) blocks Matrigel invasion of ovarian cancer cell lines, OVCAR3, OVCA-432, OVCA-433 and CAOV3. These cell lines expressed full-length MUC16 with multiple tandem repeats and released CA125 antigen into the cell culture supernatant. The fusion protein containing the carbohydrate binding domain of LGALS3 linked to the IgG1 Fc domain, $^{117-244}$LGAL3-pFUSE, significantly blocked ovarian cancer cell invasion, whereas a fusion protein containing the N-terminal protein of LGALS1, $^{11-119}$LGAL1-pFUSE, did not. Swainsonine and Kifunensine both block the synthesis of the LGALS3 ligand, polylactosamine, and also substantially decreased Matrigel invasion.

FIG. 2C illustrates inhibition of A2780 Ovarian Cancer in a tumor xenograft model by inhibitors of LGALS3 function. Cell lines were introduced into the flank of 10 athymic female nude mice per group. Loss of LGALS3 expression by shLGALS3 inhibition is highly inhibitory on tumor growth. Modest inhibition of tumor growth by $^{117-244}$LGAL3-pFUSE was also observed.

FIG. 2D illustrates antisense knockdowns of MGAT5 and LGALS3 inhibit tumor growth in an SKOV3 Ovarian Cancer xenograft mode. In SKOV3, MUC16 overexpression expression (c114) enhanced tumor growth (top line). By contrast, loss of N-glycosylation sites (N1-N24-N13-mut c114), or shRNA against MGAT5 or LGALS3 reduced growth back to control levels.

Example 3. Generation of Galectin-3 Antibodies

To generate high-affinity anti galectin-3 (LGALS3) antibodies, several strategies were employed in separate campaigns.

In the first immunization campaign (Campaign 1), 5 female BALB/c mice were immunized with a series of immunogens at a dose of 50 µg/mouse intraperitoneally (IP) every 3 weeks for a total of 7 injections. The first 5 immunizations were done with the fusion protein produced by the $^{117-244}$LGALS3-pFUSE-hIgG1-Fc2 construct (Example 1). The last 2 immunizations were done with human LGALS3 protein (OriGene; Rockville, MD). The immune sera from the mice were collected at the time of every immunization and screened for reactivity against LGALS3 by enzyme linked immunosorbent assay (ELISA). Following the last immunization, 2 of the 5 immunized mice which showed high ELISA titers to the antigen were selected and intravenously (IV) boosted with the human LGALS3 protein at a dose of 10 µg/mouse (one mouse was planned for sacrifice while the other selected as a backup). Twenty-four hours following the IV boost, the mouse was sacrificed; splenocytes were harvested, fused with SP2/mIL6 hybridoma fusion partner and plated in 96 well plates at 10, 1, 0.3, or 0.1 cells/well. Hybridoma supernatants were then collected and screened for LGALS3 binding. Positive supernatant hybridomas were expanded from single 96 well plates to multiple 96 well plates and then to 24 well plates. At every passage of hybridoma cells, ELISA reactivity to the antigen was tested to avoid false positives.

To increase the antibody yield, a second immunization campaign was undertaken (Campaign 2). A 23-amino acid custom peptide was synthesized from the sugar binding domain of LGALS3, CNTKLDNNWGREERQSVFPFESG (SEQ ID NO: 2) (called Peptide 1) (Atlantic Peptides, Lewisburg, PA). The peptide sequence was chosen as it was noted to be conserved among various species and therefore represented a critical region of the protein. The peptide was then conjugated to keyhole limpet hemocyanin (KLH) using Imject Maleimide-Activated mcKLH Kit (Rockford, IL), creating the KLH-Peptide 1.

The 4 remaining mice were then immunized with KLH-Peptide 1 at 50 µg/mouse IP every 3 weeks for a total of 3 injections. Immune sera were collected and screened for reactivity against LGALS3 and Peptide 1 by ELISA. Following the last immunization, two mice were chosen to receive an IV boost of KLH-Peptide 1 at 10 µg/mouse and 24-hours later, one mouse was sacrificed. The splenocytes of this mouse were fused with hybridoma fusion partner as described above.

Hybridoma supernatants were screened for immunoglobulin (Ig) isotype by ELISA and IgG1, IgG2a, and IgG2b isotypes were selected. Supernatants were also screened against mouse LGALS3 (mLGALS3), human LGALS1, human LGALS7 and human LGALS9. Hybridoma cells that were producing the desired antibodies were chosen for purification (by Bio X Cell; West Lebanon, NH).

Additional antibodies have also been generated using the AlivaMab mouse platform (Ablexis). The AlivaMab mouse generates chimeric antibodies having a human variable domain.

Example 4. Functional Assays to Characterize Galectin-3 Antibodies

Once the purified anti-Gal3 antibodies were obtained, they were screened for their activity using binding, invasion and anti-tumor assays.

Methods:

ELISA: Purified antibodies that bound to Gal3 were confirmed by ELISA. For this, two strategies were used. The first utilized a plastic 96-well microplate coated with LGALS3 protein and an isotype specific secondary antibody conjugated Horse-Radish-Peroxidase (HRP) for detection. As there was concern that LGALS3 would not retain its native confirmation on a plastic plate, for the second strategy, an LGALS3 construct was created with polyhistidine-tag at the N-terminus (Abcam, ab89487). A nickel coated 96-well microplate was used with polyhistidine-tagged LGALS3 as the primary protein. Similarly, an isotype specific secondary antibody was used for detection.

SPR: Antibody binding to LGALS3 was confirmed by surface plasmon resonance (SPR) assay. The antibody was captured on an anti-mouse Fc surface and an 8-pt. 2-fold dilution series of LGALS3 was flown over the antibody starting at 500 nM.

Antibodies that screened positive on the nickel plated ELISA and SPR were carried forward to other experiments.

Laminin binding inhibition: To check whether the LGALS3 binding to laminin could be interrupted by the antibodies, an ELISA assay was utilized. Various antibody concentrations were used against a fixed laminin concentration.

A Maxisorb plate was coated overnight with 50 µl of Sigma Laminin (10 µg/ml in PBS) at 4° C. with orbital shaking. The next morning, the plate was equilibrated to room temperature, washed 3 times with PBS-Tween 20 (PBS-T) and blocked for 2 hours with SuperBlock (Thermo Scientific). Wells were incubated with Galectin-3:Biotin for 1 hour at room temperature. Wells were then washed 3 times with PBS-T and incubated with either 50 µl of Anti-Biotin-HRP (1:5000) or streptavidin-HRP (1:1000) for 1 hour. Plate was then washed 3 times and incubated with 100 µl TMB-Ultra for 30 minutes followed by addition of 100 µl 2N $H_2SO_4$ and read on a plate reader at wavelength 450 nm.

Matrigel Invasion Assay: Antibody inhibition of basement membrane invasion was determined in Matrigel invasion chambers as previously described by Rao, et al. (2017) *ACS Chem. Biol.* 12 (8): 2085-2096, which is incorporated by reference in its entirety. Briefly, MUC16 expressing cell lines were created by transfecting MUC16-negative human ovarian cancer cell lines (SKOV3 and A2780) with the sequence elements of the C-terminal MUC16, which are essential for tumor promoting effects, using the phrGFP vector (A2780-phrGFP-MUC16$^{c344}$ and SKOV3-phrGFP-MUC16$^{c344}$).

The transfected cells as well as wild type MUC16 expressing cells (OVCAR3) were pretreated with a selected antibody prior to exposure to the Matrigel invasion chambers. The number of invading cells was counted.

Mouse models: Lead antibodies from the in vitro experiments were then used to evaluate antibody efficacy in a transplanted ovarian tumor growth xenograft model.

A2780-MUC16$^{c344}$ cells were introduced into the flank area of 16 female athymic nude mice at 2 million cells per mouse. Similarly, control A2780-phrGFP cells were introduced into the flanks of 6 female athymic nude mice at 2 million cells per mouse. Eight of the mice that were implanted with A2780-MUC16$^{c344}$ transfected cells received twice weekly antibody injections at 50 µg/mouse intravenously (i.v.). Routine animal care was provided by the MSKCC Antitumor Assessment Core Facility. Tumor measurements were taken twice a week and tumor growth recorded as per guidelines from the MSKCC Research Animal Resource Center. Animals were sacrificed after reaching a maximum tumor volume of 2000 mm$^3$.

Statistical Analyses: To compare studies of growth and invasion, data was expressed as Mean±Standard Error (SE) and was analyzed for statistical significance using Unpaired Student's t-test. Kaplan Meier curves were constructed for survival and log-rank test used to determine significance. (Stata 14, StataCorp 2015; College Station, TX).

Results:

There were 2 antibodies generated from the first immunization campaign and 12 additional antibodies generated from the second immunization campaign (Table 1). Table 1 provides a summary of selected antibodies generated, their immunoglobulin isotypes, and their antibody antigen targets. In the table below, LGALS3 is human Galectin-3, Peptide-1 is a 23-amino acid constructed peptide from the conserved region of the carbohydrate binding domain of LGALS3, mLGALS3 is mouse Galectin-3, LGALS1 is human Galectin-1.

TABLE 1

Summary of Selected Antibodies Generated, immunoglobulin isotypes, and antibody antigen targets.

| Immunization campaign | Antibody name | Ig isotype | kappa/lambda | Antigen target |
|---|---|---|---|---|
| 1 | 112516.1D1.2F9 | IgG1 | kappa | LGALS3, mLGALS3 |
| 1 | 112516.14D11.2D2 | IgG1 | kappa | LGALS3, mLGALS3 |
| 2 | 22417a.1D1.E12 | IgG1 | lambda | Peptide-1, LGALS3, mLGALS3 |
| 2 | 22417a.3G10.D11 | IgG1 | lambda | Peptide-1, LGALS3, mLGALS3 |
| 2 | 22417a.7A2.A7 | IgG1 | lambda | Peptide-1, LGALS3, mLGALS3 |
| 2 | 22417a.11D1.Al2 | IgG1 | lambda | Peptide-1, LGALS3, mLGALS3 |
| 2 | 22417a.11E12.E4 | IgG1 | lambda | Peptide-1, LGALS3, mLGALS3 |
| 2 | 22417a.1E4.E11 | IgG2b | kappa | Peptide-1, LGALS3, mLGALS3 |
| 2 | 22417a.5G2.A6 | IgG2b | kappa | Peptide-1, LGALS3, mLGALS3 |
| 2 | 22417a.4B10.B12 | IgG2b | kappa | Peptide-1, LGALS3, mLGALS3 |
| 2 | 22417a.5G4.A3 | IgG2a | kappa | Peptide-1, LGALS3, mLGALS3 |
| 2 | 22417a.12A11.A7 | IgG2a | lambda | Peptide-1, LGALS3, mLGALS3, LGALS1 |
| 2 | 22417b.21Al2.A6 | IgG2a | lambda | Peptide-1, LGALS3, mLGALS3, LGALS1 |
| 2 | 22417b.15D12.A7 | IgG2b | lambda | Peptide-1, LGALS3, mLGALS3, LGALS1 |

Figure 6:
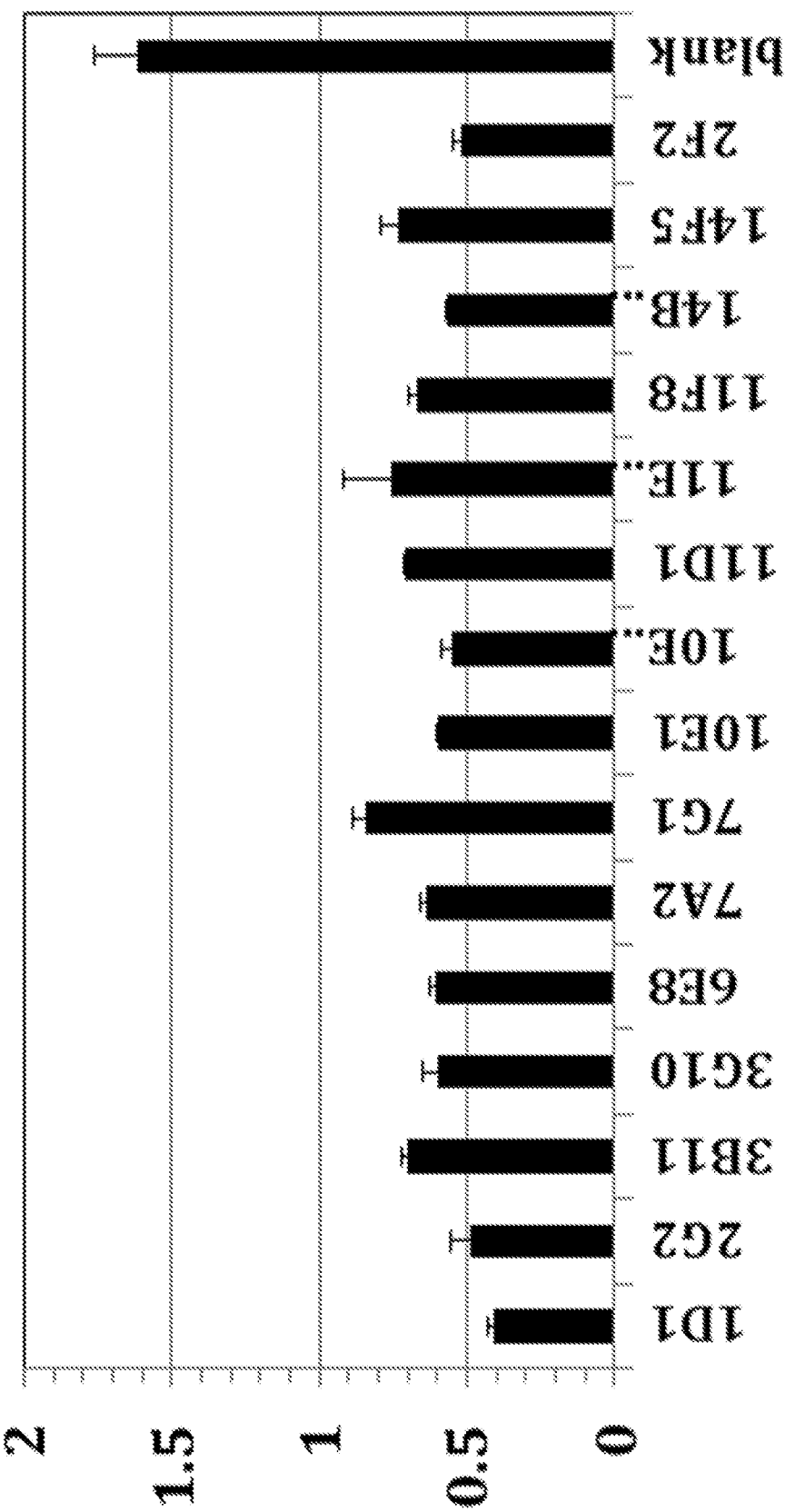
FIG. 6 illustrates inhibition of LGALS3 binding to laminin by the candidate antibodies.

FIG. 5 shows a summary of the binding properties of the antibodies from campaign 2. FIG. 6 shows the ELISA results for the binding of the campaign 2 antibodies to laminin.

Figure 7:
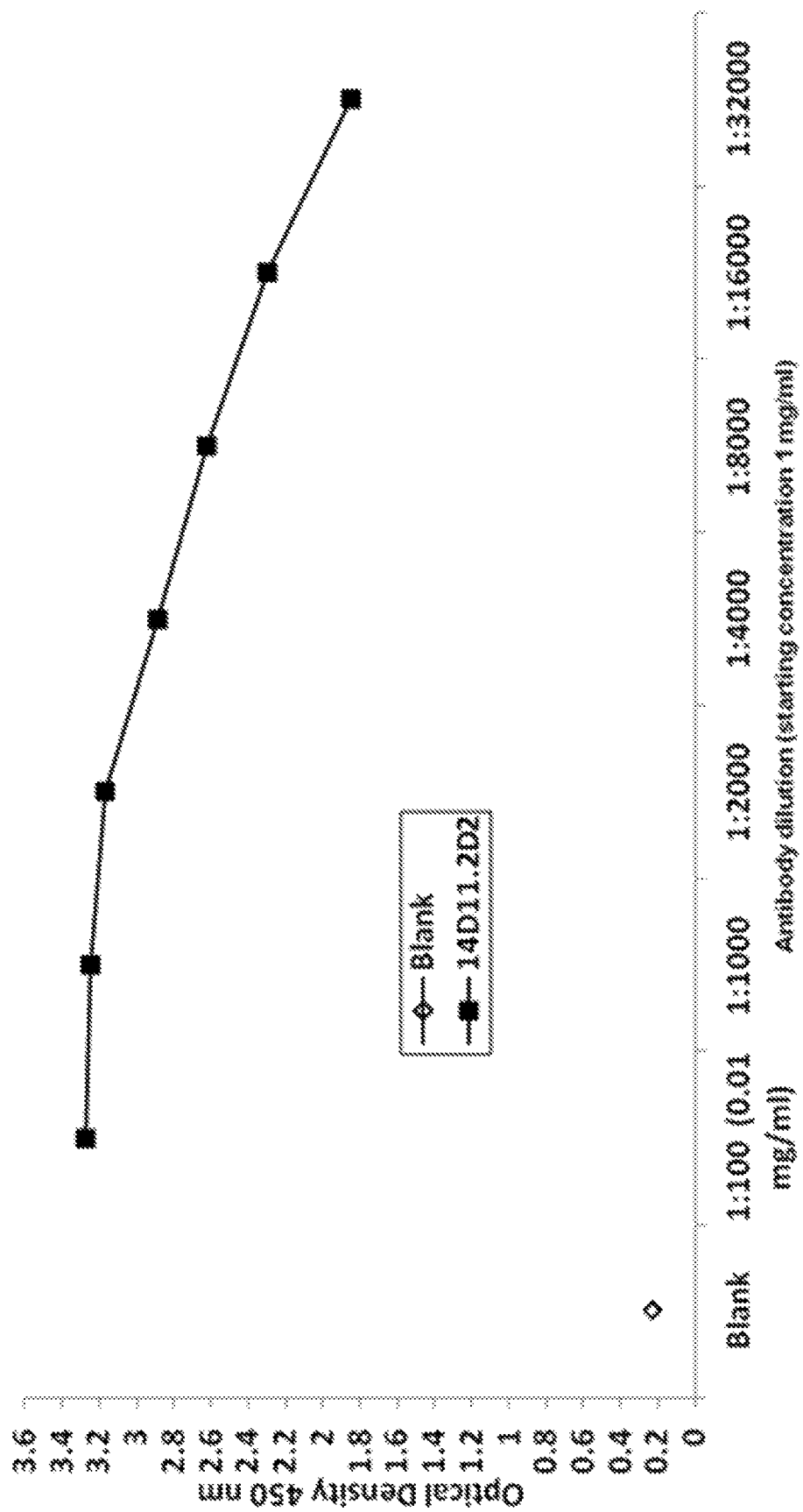
FIG. 7 illustrates binding of antibody 14D11.2D2 to LGALS3 in an ELISA assay utilizing nickel plated 96-well microplates, polyhistidine-tagged LGALS3 as primary protein at 500 ng/well, dilutions of primary antibody 14D11.2D2 with a starting concentration of 1 mg/mL, and secondary antibody of goat anti-mouse IgG1-HRP at 1:3000 dilution.
Figure 8:
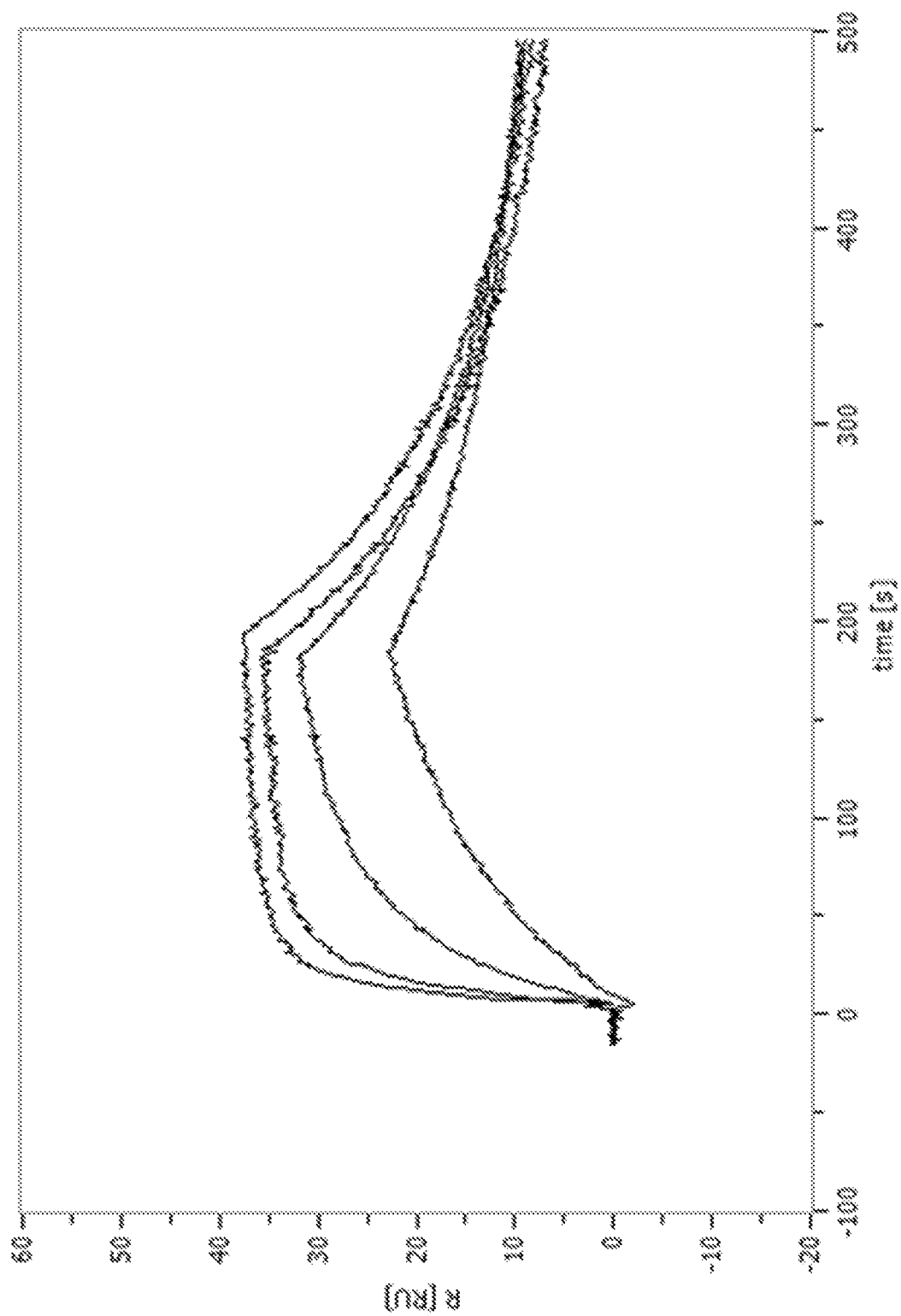
FIG. 8 illustrates binding of antibody 14D11.2D2 to LGALS3 in a surface plasmon resonance (SPR) assay. Topmost curve 14D11.2D2 at 250.0 nM, second curve 14D11.2D2 at 125.0 nM, third curve 14D11.2D2 at 31.25 nM and bottommost curve 14D11.2D2 at 7.813 nM. This yielded a dissociation constant (KD) value of 14.6 nM.
Figure 9:
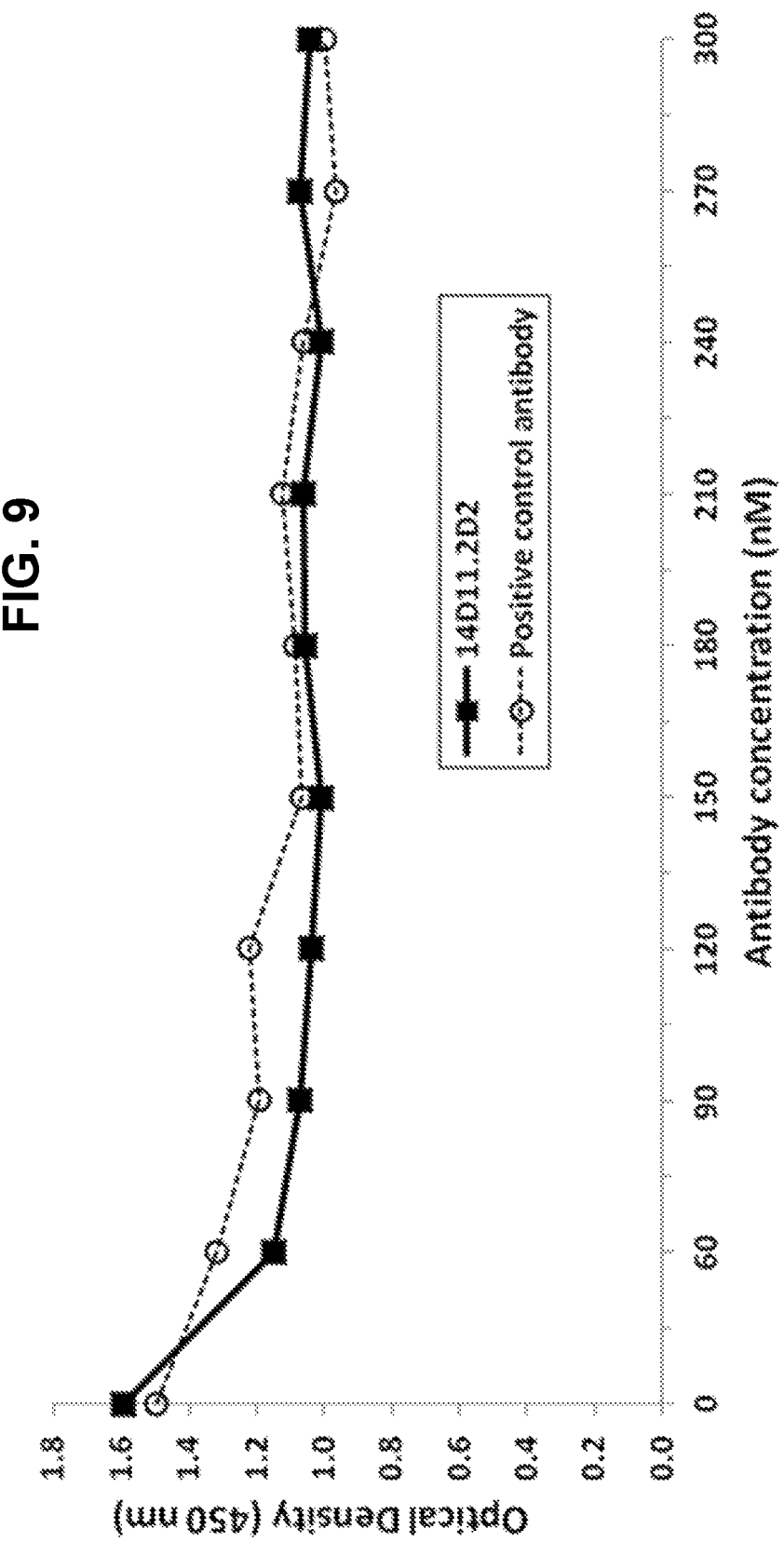
FIG. 9 illustrates an ELISA assay showing 14D11.2D2 blocking of LGALS3 binding to laminin. At a concentration of 250 nM, 14D11.2D2 decreased LGALS3 binding by 36.6%.
Figure 10:
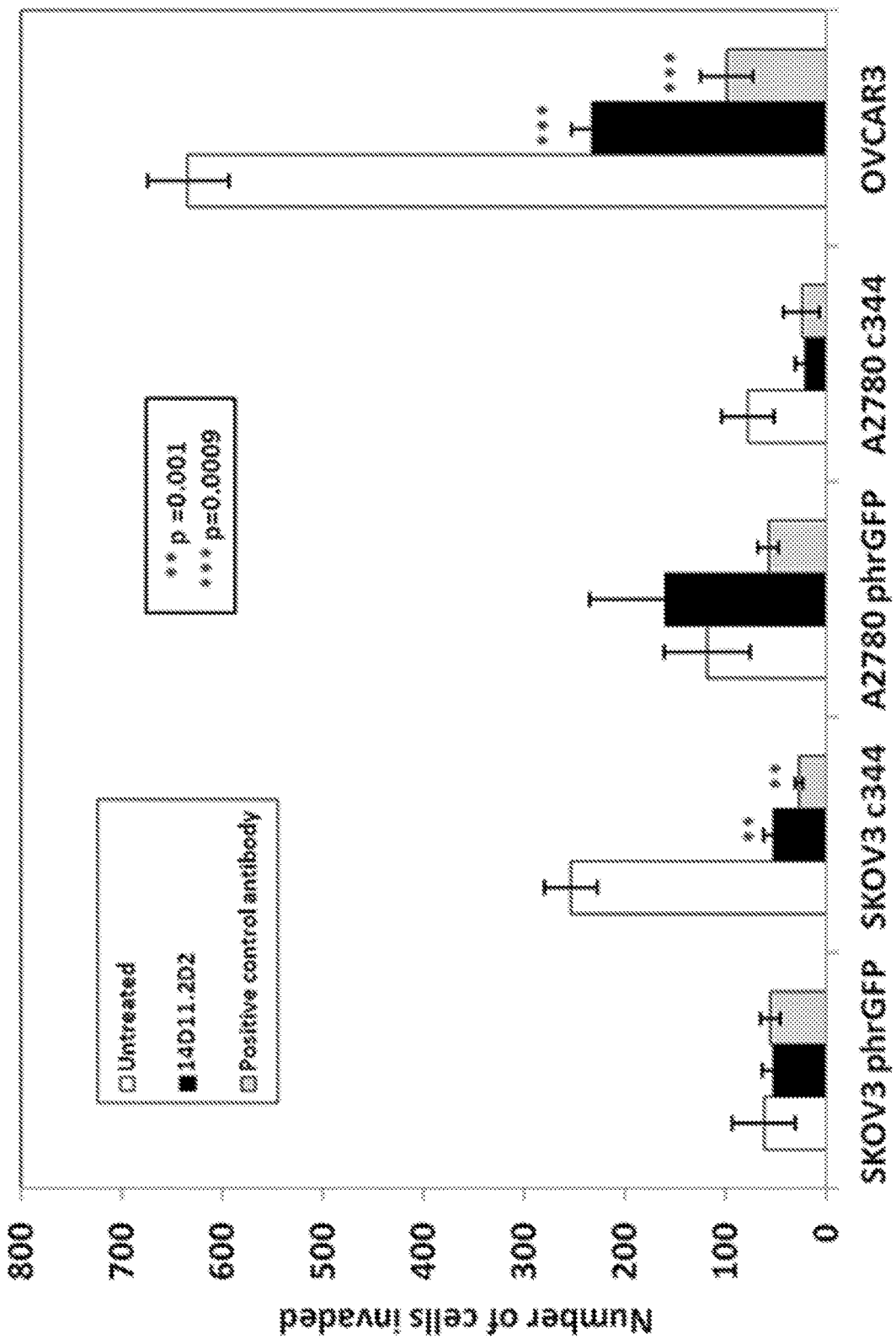
FIG. 10 illustrates 14D11.2D2 inhibits invasion of SKOV3-MUC16c344 (SKOV3c344), A2780-MUC16c344 (A2780c344), and OVCAR3 cell lines as compared to untreated cells in a Matrigel invasion assay.  or * denotes statistically significant difference between untreated cells and cells treated with antibody. The Matrigel Invasion assay was done using SKOV3-MUC16c344, A2780-MUC16c344, and wild type OVCAR3 cell lines. Significantly fewer MUC16 transfected SKOV3 cells were noted to invade the Matrigel membrane when treated with antibody (p=0.001); similar results were noted for OVCAR3 cells treated with antibody (p=0.0009). MUC16 transfected A2780 cells showed a decreased cellular invasion in the presence of 14D11.2D2 but did not reach statistical significance (p=0.1067).

Achieving a high affinity antibody to native LGALS3 was particularly difficult. Although all antibodies in campaigns 1 and 2 screened positive for binding to LGALS3 on an ELISA assay, only 112516.14D11.2D2 showed affinity for native LGALS3 by SPR (FIGS. 7 and 8). Therefore, it was the only antibody that was screened using functional assays. 112516.14D11.2D2 is also referred to herein as 14D11.2D2. FIG. 7 shows that 14D11.2D2 binds LGALS3 protein in an ELISA assay. FIG. 8 shows that 14D11.2D2 binds LGALS3 in an SPR assay. The antibody dissociation constant was 14.6 nM by SPR. FIG. 9 shows that 14D11.2D2 inhibits LGALS3 binding to laminin. At a concentration of 150 nM, 14D11.2D2 decreased galectin-3 binding to laminin by 36.6% compared to untreated control. FIG. 10 shows that 14D11.2D2 inhibits invasion of SKOV3-MUC16c344 (SKOV3c344), A2780-MUC16c344 (A2780c344), and OVCAR3 cell lines as compared to untreated cells in a Matrigel invasion assay. Significantly fewer MUC16 transfected SKOV3 cells were noted to invade the Matrigel membrane when treated with antibody (p=0.001). Similar results were noted for OVCAR3 cells treated with antibody (p=0.0009).

Figure 11:
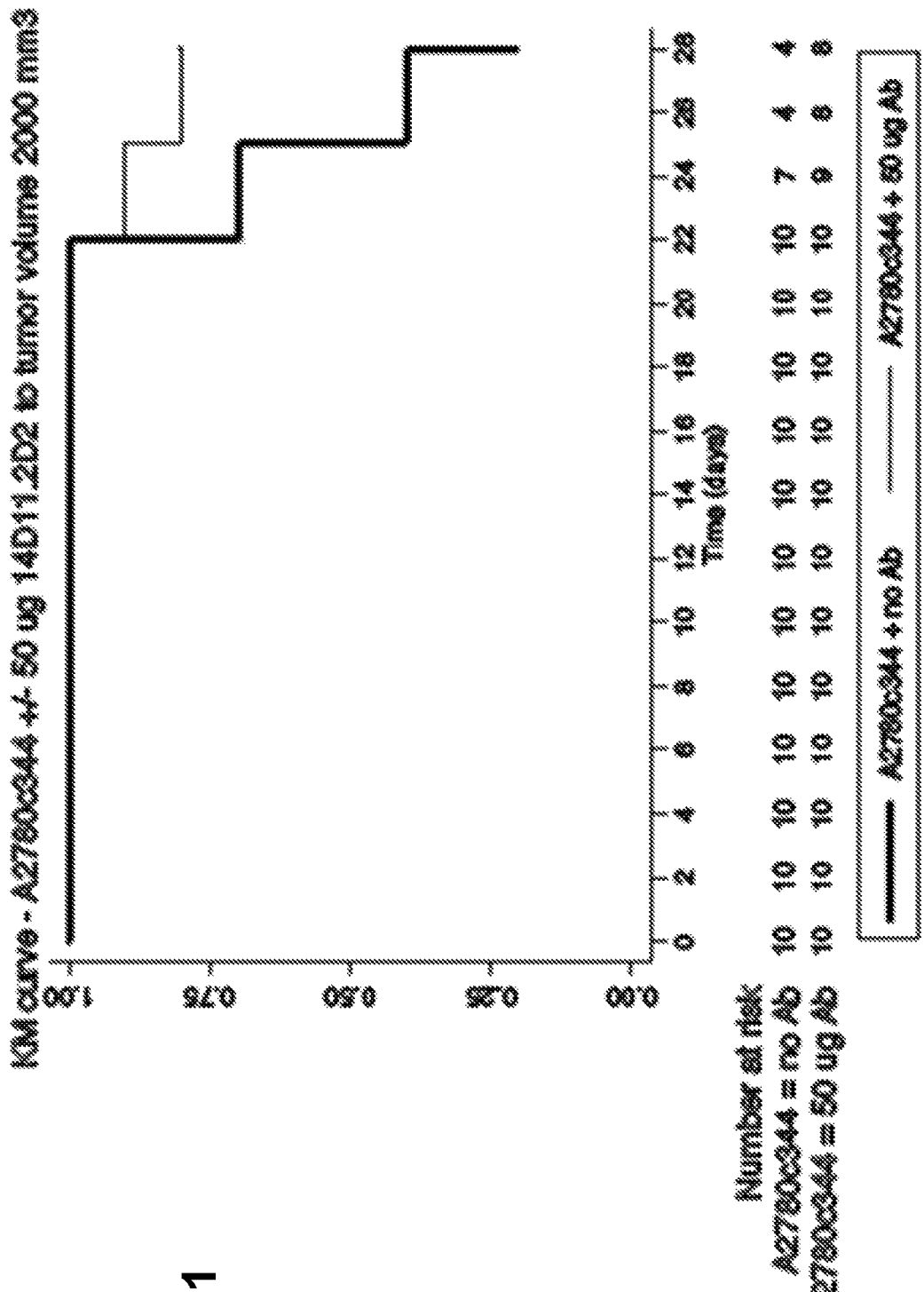
FIG. 11 illustrates the effect of increased survival of 14D11.2D2 antibody treated mice in an ovarian tumor xenograft model. Mice immunized with 14D11.2D2 antibody were more likely to survive than mice that did not receive the antibody. Ovarian tumor cells (A2780-phrGFP-MUC16c344 (A2780c344)) were implanted into flank of 20 athymic female nude mice. Ten mice were immunized with 14D11.2D2 twice weekly at 50 μg/mouse intravenously (iv) for a total of 8 injections. Tumor volumes were measured twice weekly. Mice were sacrificed once tumor volume reached 1500 mm³. A pilot mouse experiment was conducted with 14D11.2D2 using the A2780-MUC16c344 cell line. 14D11.2D2 was administered at a dose of 50 μg/mouse administered twice weekly for total of 8 doses. After 28 days, animals that did not receive the antibody were statistically significantly less likely to survive than animals that received the antibody (p=0.012).

FIG. 11 shows that mice immunized with 14D11.2D2 antibody are more likely to survive than mice that did not receive the antibody in the ovarian tumor xenograft mouse model described above. 14D11.2D2 was administered at a dose of 50 µg/mouse administered twice weekly for total of 8 doses. After 28 days, animals that did not receive the antibody were statistically significantly less likely to survive than animals that received the antibody (p=0.012). In addition, MUC16 expressing A2780 tumors showed a trend in decreased tumor growth in mice treated with Mab.

Taken together these data demonstrate that the 14D11.2D2 antibody binds to non-denatured LGALS3 and exhibits anti-tumor activity.

Example 5. Loss of Metastatic Activity in Tumor Cells Lacking Galectin-3 Expression In order to demonstrate a role for LGALS3 in tumor metastasis in vivo, the metastasis of a breast cancer cell line to the lung was studied in a mouse xenograft model. For this experiment, derivatives of the MDA-MB-231 cell line, which is an epithelial, MUC16+, human breast cancer cell line, were employed. MDA-MB-231-TGL expresses luciferase and GFP to allow for non-invasive bioluminescence analysis (Minn et al. (2005) Nature 436:518-524). MDA-MB-231-TGL shGAL is a further derivative cell line in which LGALS3 is silenced using a short hairpin RNA.

Figure 14A:
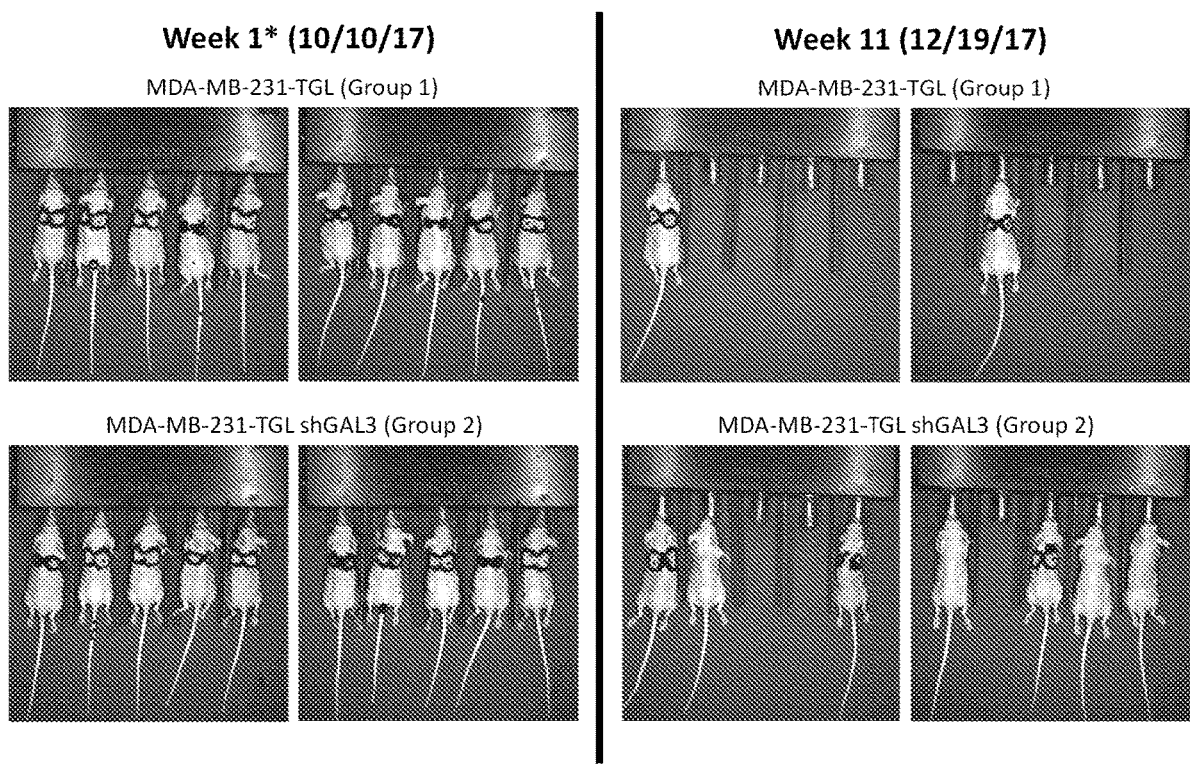
FIG. 14A illustrates loss of metastatic lung tumor development in athymic mice injected with breast cancer cell line deficient for LGALS3 expression. Athymic nude female mice, 6-8 weeks old at start of experiment; Group 1 (10 mice) and Group 2 (10 mice) underwent tail vein injections with $1.5 \times 10^6$ cells of MDA-MB-231-TGL wt or MDA-MB-231-TGL shGAL3, respectively; dorsal imaging shown; *Week 1 is one week after injection. MDA-MB-231 cell line is an epithelial, human breast cancer cell line.
Figure 14B:
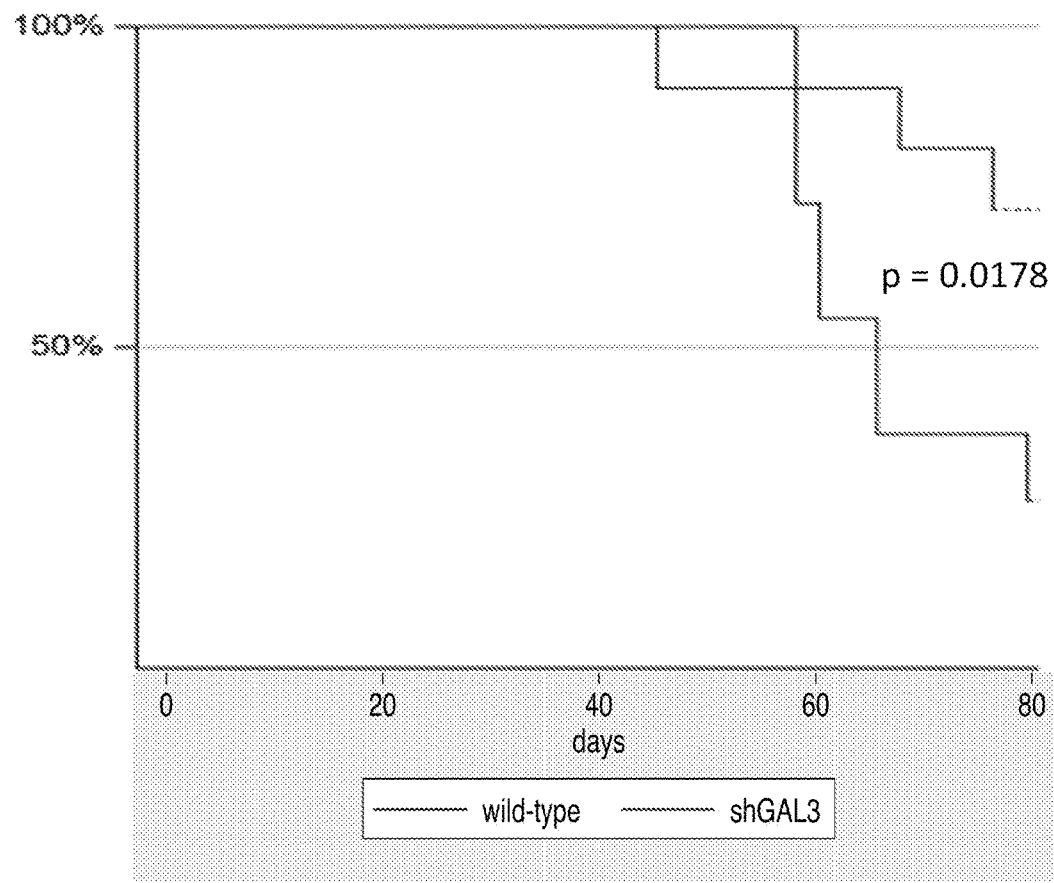
FIG. 14B illustrates the prolonged survival of the LGALS3 deficient mice as shown by Kaplan-Meier survival curve. p=0.0178.

Athymic nude female mice at 6-8 weeks old at start of experiment were divided into two groups, Group 1 (10 mice) and Group 2 (10 mice), and administered via tail vein injection $1.5 \times 10^6$ cells of MDA-MB-231-TGL wt or MDA-MB-231-TGL shGAL3, respectively. FIG. 14A shows dorsal imaging of the injected mice at one week and 11 weeks after injection. FIG. 14B shows the survival curve for the experiment. The mice injected with the LGALS deficient cells exhibited a significant decrease in lung metastases even after establishment of the tumor at week (compare Group 1 week 1 to week 11). In several mice, the tumors appeared completely eradicated (FIG. 14A). The mice injected with the LGALS deficient cells also exhibited significantly longer survival (FIG. 14A).

Figure 14C:
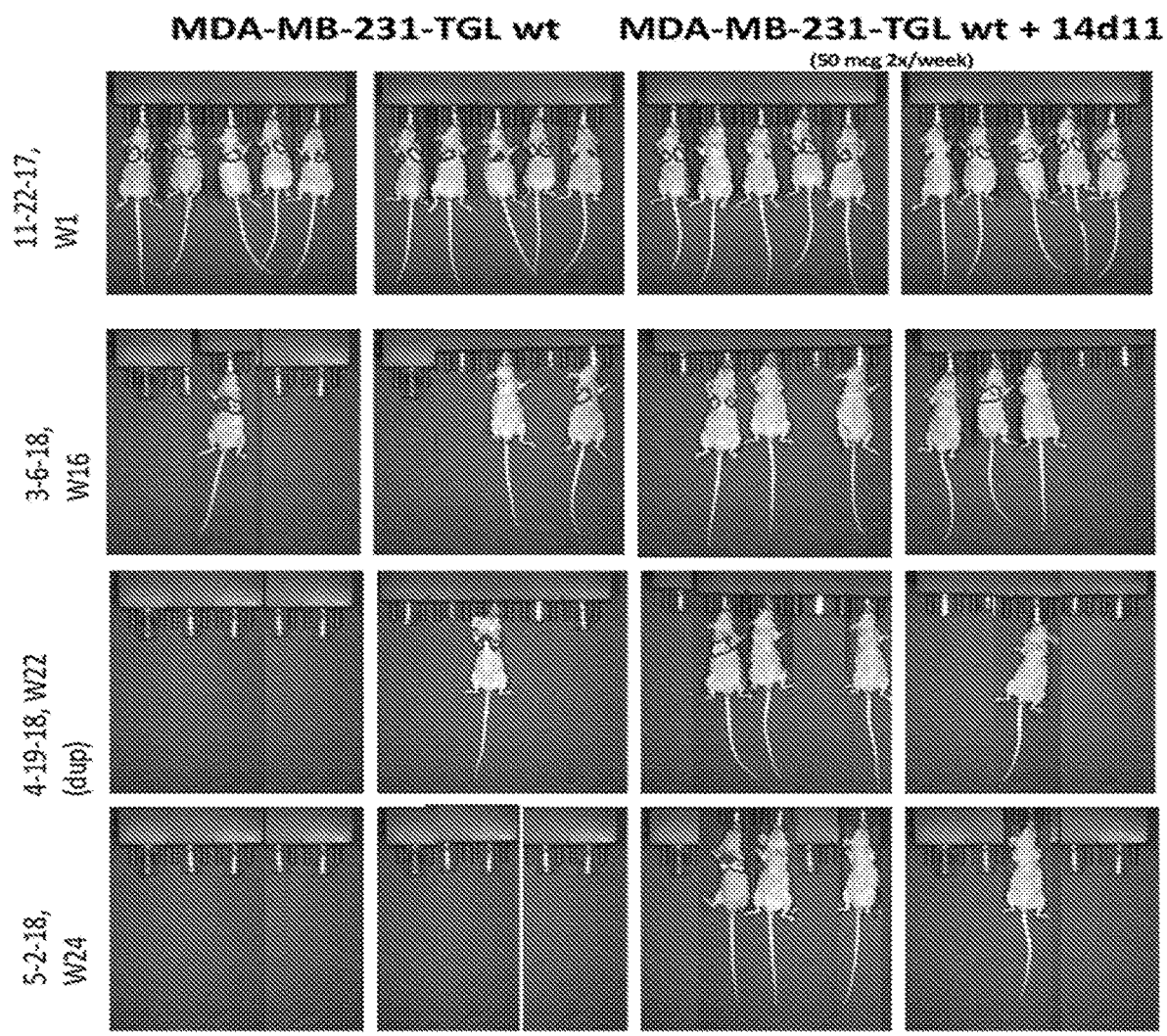
FIG. 14C illustrates the effects of treatment with the 14D11.2D2 antibody on tumor development in MDA-MB-231-TGL breast cancer cell injected mice.

Based on the above results, the effect of the 14D11.2D2 anti-LGALS3 antibody on metastasis was examined. As expected, administration of an anti-LGALS3 antibody recapitulated the effect of LGALS3 siRNA on lung metastasis. As shown in FIG. 14C, administration of the 14D11 antibody both increased survival and eliminated cancer metastases from about ⅓ of the mice. Taken together, these data support the use of anti-LGALS3 antibody therapy to inhibit LGALS3 function for the treatment of metastases and metastatic cancers.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

What is claimed is:

1. An antibody or an antigen-binding fragment thereof, wherein the antibody or antigen-binding fragment thereof comprises a heavy chain variable region (VH), wherein the antibody or antigen-binding fragment comprises:
   (a) a VH complementarity determining region (CDR) 1 comprising the amino acid sequence of SEQ ID NO: 5, a VH CDR2 comprising the amino acid sequence of SEQ ID NO: 6, and a VH CDR3 comprising the amino acid sequence of SEQ ID NO: 7, a VL CDR1 comprising the amino acid sequence of SEQ ID NO: 8, a VL CDR2 comprising the amino acid sequence of SEQ ID NO: 9, and a VL CDR3 comprising the amino acid sequence of SEQ ID NO: 10; or
   (b) a VH CDR1 comprising the amino acid sequence of SEQ ID NO: 11, a VH CDR2 comprising the amino acid sequence of SEQ ID NO: 12, and a VH CDR3 comprising the amino acid sequence of SEQ ID NO: 13, a VL CDR1 comprising the amino acid sequence of SEQ ID NO: 14, a VL CDR2 comprising the amino acid sequence of SEQ ID NO: 15, and a VL CDR3 comprising the amino acid sequence of SEQ ID NO: 16; or
   (c) a VH CDR1 comprising the amino acid sequence of SEQ ID NO: 17, a VH CDR2 comprising the amino acid sequence of SEQ ID NO: 18, and a VH CDR3 comprising the amino acid sequence of SEQ ID NO: 19, a VL CDR1 comprising the amino acid sequence of SEQ ID NO: 20, a VL CDR2 comprising the amino acid sequence of SEQ ID NO: 21, and a VL CDR3 comprising the amino acid sequence of SEQ ID NO: 22; and
   wherein the antibody or an antigen-binding fragment thereof immunospecifically binds to a Galectin-3 (LGALS3) carbohydrate binding domain (CBD), wherein the LGALS3 CBD comprises SEQ ID NO: 27.

2. The antibody or antigen-binding fragment thereof of claim 1, wherein the antibody or antigen-binding fragment thereof
   inhibits in vitro invasion of tumor cells in a Matrigel invasion assay;

inhibits binding of LGALS3 to a glycosylated cell surface protein, a glycosylated cell surface receptor, or a glycosylated growth factor receptor, inhibits binding of LGALS3 to glycosylated mucin-1 (MUC1), glycosylated mucin-4 (MUC4), glycosylated mucin-16 (MUC16), a disialoganglioside, GD2, epidermal growth factor receptor (EGFR), platelet-derived growth factor receptor (PDGFR), insulin-like growth factor receptor (IGFR), an integrin and CTLA4, or inhibits growth of a tumor that expresses a glycosylated form of MUC16.

3. The antibody or antigen-binding fragment thereof of claim 1, wherein the antibody is a monoclonal antibody or a humanized antibody.

4. The antibody or antigen-binding fragment thereof of claim 1, wherein the antibody or antigen-binding fragment thereof comprises a VL comprising the amino acid sequence of SEQ ID NO: 26 and/or a VH comprising the amino acid sequence of SEQ ID NO: 24.

5. The antibody or antigen-binding fragment thereof of claim 1, wherein the antibody comprises human-derived heavy and light chain constant regions, wherein the heavy chain constant region has an isotype selected from the group consisting of gamma 1, gamma 2, gamma 3, and gamma 4 or wherein the light chain constant region has an isotype selected from the group consisting of kappa and lambda.

6. The antibody or antigen-binding fragment thereof of claim 1, wherein the antibody comprises an immunoglobulin comprising two identical heavy chains and two identical light chains, or comprises an IgG.

7. An antibody conjugate comprising the antibody or antigen-binding fragment thereof of claim 1 conjugated to an agent.

8. The antibody or antigen-binding fragment thereof of claim 1, wherein the antibody or antigen-binding fragment thereof is a bispecific antibody.

9. The bispecific antibody of claim 8, wherein the bispecific antibody immunospecifically binds CD3.

10. The antibody or antigen-binding fragment thereof of claim 1, wherein the antigen-binding fragment thereof is a scFv.

11. A polynucleotide comprising nucleic acid sequences encoding the antibody or antigen binding fragment of claim 4.

12. An isolated cell or vector comprising the polynucleotide of claim 11 operably linked to a promoter.

13. An isolated cell comprising the vector of claim 12.

14. A pharmaceutical composition comprising: a therapeutically effective amount of the antibody or antigen-binding fragment thereof of claim 1 and a pharmaceutically acceptable carrier.

15. A method of treating cancer in a patient in need thereof, comprising administering to said patient the pharmaceutical composition of claim 14, wherein the cancer expresses glycosylated MUC16.

16. The method of claim 15, wherein the cancer is a metastatic cancer or a cancer of the ovary, lung, pancreas, breast, uterine, fallopian tube, or primary peritoneum.

17. The antibody or antigen-binding fragment thereof of claim 2, wherein the glycosylated MUC16 is N-glycosylated at Asn1800 or Asn1806.

18. The antibody of claim 6, wherein the immunoglobulin immunospecifically binds LGALS3, wherein the antibody is a bispecific antibody, and wherein each light chain of the immunoglobulin is conjugated via a peptide linker to a single chain variable fragment (scFv) that immunospecifically binds to CD3.

19. The bispecific antibody of claim 8, wherein the bispecific antibody is conjugated to an imaging agent or a cytotoxic agent.

20. The antigen-binding fragment thereof of claim 10, wherein the scFv is conjugated to an agent.

* * * * *